United States Patent
Noe et al.

(10) Patent No.: US 7,030,242 B2
(45) Date of Patent: Apr. 18, 2006

(54) SELECTIVE INHIBITION OF AGGRECANASE IN OSTEOARTHRITIS TREATMENT

(75) Inventors: Mark C. Noe, Mystic, CT (US); Michael A. Letavic, Mystic, CT (US); Louis S. Chupak, Old Saybrook, CT (US); Kim F. McClure, Mystic, CT (US)

(73) Assignees: Pfizer Inc, New York, NY (US); Pfizer Products Inc., Groton, CT (US)

( * ) Notice: Subject to any disclaimer, the term of this patent is extended or adjusted under 35 U.S.C. 154(b) by 20 days.

(21) Appl. No.: 11/120,376

(22) Filed: May 3, 2005

(65) Prior Publication Data
US 2005/0227997 A1    Oct. 13, 2005

Related U.S. Application Data
(62) Division of application No. 09/635,433, filed on Aug. 10, 2000, now abandoned.
(60) Provisional application No. 60/148,464, filed on Aug. 12, 1999.

(51) Int. Cl.
  C07D 295/26    (2006.01)
  A61K 31/495    (2006.01)
(52) U.S. Cl. ............................ 544/383; 514/255.01
(58) Field of Classification Search ........... 514/255.01; 544/383
See application file for complete search history.

(56) References Cited

U.S. PATENT DOCUMENTS

| | | | |
|---|---|---|---|
| 5,753,653 A | 5/1998 | Bender et al. | |
| 6,329,397 B1 * | 12/2001 | McClure et al. | 514/330 |
| 6,599,890 B1 | 7/2003 | McClure et al. | |

FOREIGN PATENT DOCUMENTS

| | | |
|---|---|---|
| EP | 606046 | 7/1994 |
| WO | WO 96/33172 | 10/1996 |
| WO | WO 98/08815 | 3/1998 |
| WO | WO 98/08825 | 3/1998 |
| WO | WO 98/34918 | 8/1998 |
| WO | WO 99/58528 | 11/1999 |
| WO | WO 99/58531 | 11/1999 |
| WO | WO 00/09485 | 2/2000 |
| WO | WO 00/09492 | 2/2000 |

* cited by examiner

Primary Examiner—Thomas C. McKenzie

(74) Attorney, Agent, or Firm—Eric J. Baude; Charles W. Ashbrook

(57) ABSTRACT

This invention relates to a method of treatment for osteoarthritis involving inhibitors of aggrecanase that demonstrate $IC_{50}s$ of less than 20 nM and demonstrate differential potency against matrix metalloproteinases (MMPs) and a disintegrin and metalloproteinases (ADAMs or reprolysins). This invention also relates to compounds, methods of treatment and composition of Formula I:

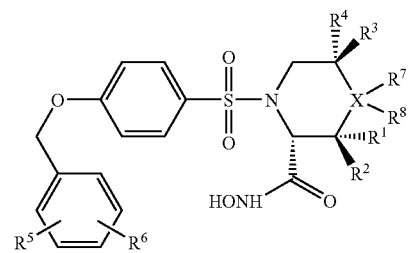

or a therapeutically acceptable salt thereof, wherein
  X is carbon or nitrogen;
  $R^1$ and $R^2$ are independently selected from the group consisting of hydrogen, hydroxy, and methyl, wherein at least one of $R^1$ and $R^2$ is methyl;
  $R^3$ and $R^4$ are independently selected from the group consisting of hydrogen, hydroxy, and methyl, or $R^3$ and $R^4$ may be taken together to form a carbonyl group; and
  $R^5$ and $R^6$ are independent substituents in the ortho, meta, or para positions and are independently selected from the group consisting of hydrogen, halogen, cyano, methyl, and ethyl;
with the provisos:
  when X is carbon, then $R^7$ and $R^8$ are both hydrogen and at least one of $R^1$, $R^2$, $R^3$, and $R^4$ is hydroxy;
  when X is carbon and $R^5$ is para-halo, then at least one of $R^6$, $R^3$, and $R^4$ is not hydrogen;
  when X is nitrogen, then $R^8$ is not present and $R^7$ is hydrogen or a group of the formula:

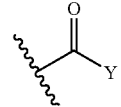

wherein, Y is —$CH_2$—$NH_2$ or —NH—$CH_3$; and
when X is nitrogen and $R^7$ is H, then $R^3$ and $R^4$ are taken together to form a carbonyl group.

3 Claims, No Drawings

SELECTIVE INHIBITION OF AGGRECANASE IN OSTEOARTHRITIS TREATMENT

CROSS REFERENCE

This application is a divisional of U.S. patent application Ser. No. 09/635,433, filed Aug. 10, 2000, now abandoned, and claims benefit of priority from U.S. provisional application No. 60/148,464, filed Aug. 12, 1999.

TECHNICAL FIELD

The current invention concerns carboxylic acid hydroxyamide derivatives that are highly potent inhibitors of aggrecanase proteolytic activity and that inhibit other enzymes implicated in joint disease, particularly matrix metalloproteinases (MMPs) and the a disintegrin and metalloproteinases (ADAMs or reprolysins). The current invention also relates to synthetic precursors to the carboxylic acid hydroxyamide inhibitors, to pharmaceutical compositions, and to methods of treatment, especially the treatment of osteoarthritis.

BACKGROUND OF THE INVENTION

Osteoarthritis is characterized by progressive enzymatic destruction of type II collagen and aggrecan, which are the two major components of cartilage matrix. Type II collagen is essential for cartilage tensile strength and its degradation causes progression of osteoarthritis.

Aggrecan is composed of a core protein of approximately 2400 amino acids. The molecule consists of several structural and functional domains (Falnnery et al., *Matrix Biology* 16, 1998, 507–511). Three domains are defined on the N-terminal side: (1) the G1, (2) the interglobular, and (3) the G2 domain. The aggrecan C-terminal side comprises two glycosaminoglycan rich domains. As shown in the aggrecan representation below, the G1 domain is separated from a second globular domain, G2, by about 150 amino acids, known as the interglobular domain. From the G2 domain to the C-terminus there is a long extended region consisting of two glycosaminoglycan-rich domains. The first is rich in keratan sulfate, whereas that which follows is rich in chondroitin sulfate.

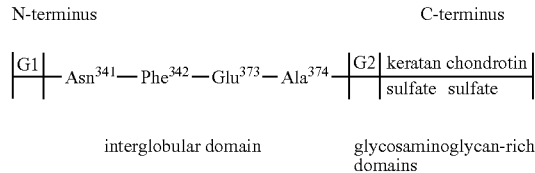

The G1 domain of aggrecan binds to long hyaluronic acid polymers, thereby forming multi molecular aggregates that effectively immobilize aggrecan within the collagen fibrillar meshwork. The glycosaminoglycan domains provide osmotic pressure, which enables cartilage to resist compression.

Current osteoarthritis therapies (e.g., non-steroidal anti-inflamatories or NSAIDs) have limited symptomatic benefit and have only modest, if any, effects on slowing cartilage destruction in osteoarthritic joints. NSAIDs, such as, acetaminophen, act by inhibiting the synthesis of cytokines, such as, prostaglandins that cause pain, and swelling. Thus, NSAIDs do not directly prevent cartilage destruction, whereas inhibitors of cartilage degrading enzymes will block cartilage collagen and aggrecan degradation thereby blocking or slowing the progression of osteoarthritis. Thus, inhibition of the enzymes should have a more direct and specific effect on cartilage breakdown than cytokine inhibition.

The loss of aggrecan contributes to the progression of osteoarthritis. In osteoarthritis and rheumatoid arthritis, aggrecan is one of the first cartilage matrix components to undergo measurable loss (Mankin et al., *J Bone Joint Surg.* 52A, 424–434 (1970)).

In human arthritis, aggrecan degradation is associated with amino acid cleavage within the interglobular domain, at either the $Asn^{341}$-$Phe^{342}$ or the $Glu^{373}$-$Ala^{374}$ site. In vitro studies have demonstrated that the aggrecan $Asn^{341}$-$Phe^{342}$ bond can be cleaved by several collagenases including collagenase-1 and collagenase-3 (Fonsang et al., *FEBS Lett.* 380: 17–20, 1996a), however, digestion of aggrecan with a number of these purified proteases has not resulted in cleavage at the $Glu^{373}$-$Ala^{374}$ site (Fonsang et al., *J. Biol. Chem.* 267, 19470–19074, (1992); Flannery et al *J. Biol. Chem.* 267, 1008–1014 (1992)).

Recently, an enzyme that demonstrated aggrecanase proteolytic activity—i.e., cleaves the $Glu^{373}$-$Ala^{374}$, but not the $Asn^{341}$-$Phe^{342}$ site of aggrecan—has been identified (Arner et al., PCT publication WO 99/05291; Arner et al., *J. Bio. Chem.* 274 (10) 6594–6601 (1999); and Tortorella et al., *Science* 284, 1664–1666 (1999)). The enzyme was designated aggrecan degrading metalloprotease (ADMP) or ADAMTS-4.

WO 99/05291 teaches that the zymogen form of the isolated and purified ADMP consist of a propeptide domain containing a furin cleavage site, a metalloprotease domain, an a disintegrin-like domain, and a thrombospondin homologous domain (i.e., region of the molecule containing one or more thrombospondin type 1 (TSP1) repeats).

ADAMTS-4 is classified within the a disintegrin and metalloproteinase (ADAM or reprolysin) subfamily of the metazincins (Rawlings et al., *Methods in Enzymology* 248, 183–228 (1995) and Stocker et al., *Protein Science* 4, 823–840 (1996)). ADAMs represent a new family of genes that show a significant sequence similarity to snake venom metalloproteinase and disintegrin (Hite et al., *Biochemistry* 31, 6203–6211 (1992); Wolfberg et al., *J. Cell Bio.* 131, 275–278 (1995)).

Some ADAMS cause the release of inflammatory cytokines and the levels of these harmful ADAMs are often increased in joint disease. For example, ADAM-17—also known as tumor necrosis factor-alpha converting enzyme (TACE)—is responsible for cleavage of cell bound tumor necrosis factor-alpha (TNF-α). TNF-α is involved in many auto-immune diseases (W. Friers, *FEBS letters* 285, 199 (1991)). There are two forms of TNF-α, a type II membrane protein of relative molecular mass 26 kD and a soluble 17 kD form generated from the cell bound TNF-αby specific TACE proteolytic cleavage. The 17 kD form of TNF-α is released by the cell and is associated with the deleterious side effects of TNF-α. Thus, inhibitors of TACE prevent the formation of soluble TNF-α and so obviate its toxic side effects.

On the other hand, there are instances where compounds that inhibit matrix degrading enzymes-such as, MMP-13 and aggrecanase—but do not have a strong TACE inhibitory action, are preferred.

Other ADAMs include ADAMTS-1 (Kuno et al., *J. Biol. Chem.* 272, 556–562 (1997) and Tang et al., FEBS Letters 445, 223, 1999), and ADAMs 10, 12, and 15 (Wu et al., *Biochem. Biophys. Res. Comm.* 235, 437–442 (1997)).

Collagen destruction by the MMP subfamily of the zinc metalloendopeptidases is characteristic of some joint diseases, such as, osteoarthritis. The MMP subfamily contains seventeen identified members (MMP-1, MMP-2, MMP-3, MMP-7, MMP-8, MMP-9, MMP-10, MMP-11, MMP-12, MMP-13, MMP-14, MMP-15, MMP-16, MMP-17, MMP-18, MMP-19, MMP-20). The MMPs are known to regulate the turn-over of extracellular matrix proteins and as such play important roles in normal physiological processes, such as, reproduction, development, and differentiation. But the MMPs are also expressed in many pathological situations in which abnormal connective tissue turnover is occurring.

Three matrix metalloproteinases that degrade type II collagen are known, MMP-1, MMP-8, and MMP-13, referred to herein as collagenase-1, -2, and -3, respectively.

Collagenase-1 (MMP-1) is expressed in a wide variety of connective tissues throughout the body (e.g., skin, cartilage, gingiva, meniscus, tendon, and ligament) (Mitchell et al., *J. Clin. Invest.* 97, 761–768 (1996) and Wolfe et al., *Arthritis Rheum.* 36, 1540–1547 (1993)).

Collagenase-2 (MMP-8) is expressed primarily by neutrophils, but levels of MMP-8 mRNA and protein are present in human cartilage. It has been suggested that this enzyme may participate in aggrecan degradation (Chubinskaya et al., *Lab. Invest.* 74, 232–240 (1993) and Cole et al., *J. Biol. Chem.* 271, 11023–11026 (1996)).

Collagenase-3 (MMP-13) (Freije et al., *J. Biol. Chem.* 269, 16766–16773 (1994) is found almost exclusively in cartilage. This enzyme has been shown to significantly degrade type II collagen and, in addition, increased amounts are present in human osteoarthritic cartilage (Mitchell et al., *J. Clin. Invest.* 97, 761–768 (1996)).

Matrix metalloproteinase and reprolysin inhibitors are well known in the literature. Specifically, European Patent Publication 606,046, published Jul. 13, 1994, refers to certain heterocyclic MMP inhibitors. U.S. Pat. No. 5,861,510, issued Jan. 19, 1999, refers to cyclic arylsulfonylamino hydroxamic acids that are useful as MMP inhibitors. PCT Publication WO 98/34918, published Aug. 13, 1998, refers to heterocyclic hydroxamic acids including certain dialkyl substituted compounds that are useful as MMP inhibitors. PCT publications WO 96/27583 and WO 98/07697, published Mar. 7, 1996 and Feb. 26, 1998, respectively, refer to arylsulfonyl hydroxamic acids. PCT publication WO 98/03516, published Jan. 29, 1998 refers to phosphinates with MMP activity. PCT publication 98/33768, published Aug. 6, 1998, refers to N-unsubstituted arylsulfonylamino hydroxamic acids. PCT Publication WO 98/08825, published Mar. 5, 1998, refers to certain MMP inhibitors. Each of the above referenced publications and applications is hereby incorporated by reference in its entirety.

Non-selective collagenase inhibitors, i.e., inhibitors of a broad range of collagenases, are known to block collagen destruction in vivo (Nixon et al., *Int. J. Tiss. React* 13, 237–243 (1991); Mitchell et al., Annals. New York Acad. Sci. 732, 395–397 (1994); and Mort et al., Matrix 13, 95–102 (1993)). See also, PCT publications WO 96/33172 and WO 96/27583 which teach hydroxamic acids that broadly inhibit MMPs and WO 98/58925 which teaches barbiturate type MMP inhibitors.

Selective Matrix metalloproteinase and reprolysin inhibitors are disclosed in EP 935963, published Aug. 18, 1999, and U.S. Non-Provisional Patent Application "TACE Inhibitors", filed Aug. 12, 1999, which refers to certain heterocyclic hydroxamic acid compounds with differential selectivity for MMP-13, MMP-1, TACE, and aggrecanase (both of which are incorporated by reference herein). See also U.S. Non-Provisional Patent Application "Pyrimidine 2,4,6-Trione Metalloprotease inhibitors", filed Aug. 12, 1999 (incorporated herein by reference).

Although non-selective collagenase inhibitors are potential therapeutic agents, they can cause systemic connective tissue toxicity. For example, an inhibitor of both collagenase-3 and collagenase-1, revealed significant dose-related connective tissue side effects (*Proceedings of ASCO,* 15, 490 (1996)). Such connective tissue toxicity significantly limits the therapeutic utility of non-selective MMP inhibitors. It has been proposed that the toxicity of non-selective collagenase inhibitors results from suppression of normal connective tissue collagen turnover by collagenase-1. Collagenase inhibitors without collagenase-1 activity should therefore, have no or reduced connective tissue toxicity.

Diseases in which high potency inhibition of aggrecanase should provide therapeutic benefit include: osteoarthritis, joint injury, reactive arthritis, acute pyrophosphate arthritis, psoriatic arthritis, and rheumatoid arthritis. Of course, high potency inhibiting compounds are desired because lower doses can be effective. Furthermore, since it is recognized that varied combinations and concentrations of pathological enzymes are expressed in different joint diseases, compounds that inhibit several of the inflammation related proteases in addition to aggrecanase, are desirable.

BRIEF SUMMARY Of INVENTION

The present inventors now have discovered compounds that are potent inhibitors of zinc metalloendopeptidases. Particularly, the compounds are potent and selective inhibitors of aggrecanase proteolytic activity; TACE; and matrix metalloproteinases-13 (MMP-13). In another embodiment, the compounds are potent and selective inhibitors of aggrecanase proteolytic activity and matrix metalloproteinases-13 (MMP-13) that do not significantly inhibit TACE. Preferably, the compounds do not significantly inhibit collagenase-1.

One embodiment of the invention relates to compounds of Formula I

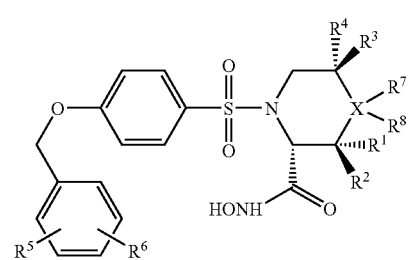

or a therapeutically acceptable salt thereof, wherein

X is carbon or nitrogen;

$R^1$ and $R^2$ are independently selected from the group consisting of hydrogen, hydroxy, and methyl, wherein at least one of $R^1$ and $R^2$ is methyl;

$R^3$ and $R^4$ are independently selected from the group consisting of hydrogen, hydroxy, and methyl, or $R^3$ and $R^4$ may be taken together to form a carbonyl group; and R⁵ and R⁶ are independent substituents in the ortho, meta, or para positions and are independently selected from the group consisting of hydrogen, halogen, cyano, methyl, and ethyl;

with the provisos:

when X is carbon, then R⁷ and R⁸ are both hydrogen and at least one of R¹, R², R³, and R⁴ is hydroxy;

when X is carbon and R⁵ is para-halo, then at least one of R⁶, R³, and R⁴ is not hydrogen;

when X is nitrogen, then R⁸ is not present and R⁷ is hydrogen or a group of the formula:

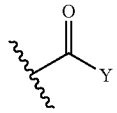

wherein, Y is —CH₂—NH₂ or —NH—CH₃; and when X is nitrogen and R⁷ is H, then R³ and R⁴ are taken together to form a carbonyl group.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The invention also relates to base addition salts of formula I. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (, potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

The subject invention also includes isotopically-labeled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as ²H, ³H, ¹³C, ¹⁴C, ¹⁵N, ¹⁸O, ¹⁷O, ³¹P, ³²P, ³⁵S, ¹⁸F, and ³⁶Cl, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as ³H and ¹⁴C are incorporated, are useful in drug and/or substrate tissue distribution assays. Tritiated, i.e., ³H, and carbon-14, i.e., ¹⁴C, isotopes are particularly preferred for their ease of preparation and delectability. Further, substitution with heavier isotopes such as deuterium, i.e., ²H, can afford certain therapeutic advantages resulting from greater metabolic stability, for example increased in vivo half-life or reduced dosage requirements and, hence, may be preferred in some circumstances. Isotopically labeled compounds of Formula I of this invention and prodrugs thereof can generally be prepared by carrying out the procedures disclosed in the Schemes and/or in the Examples and Preparations below, by substituting a readily available isotopically labeled reagent for a non-isotopically labeled reagent.

The compounds of formula I may have chiral centers and therefore exist in different enantiomeric forms. This invention relates to all optical isomers, diastereomers, atropisomers, stereoisomers and tautomers of the compounds of formula I, and mixtures thereof, and the synthetic intermediates described herein.

The heterocyclic ring of Formula I is numbered as follows:

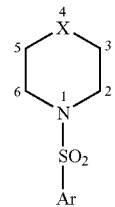

The term "alkyl", as used herein, unless otherwise indicated, includes saturated monovalent hydrocarbon radicals having straight, branched or cyclic moieties or combinations thereof.

The term "alkoxy", as used herein, includes O-alkyl groups wherein "alkyl" is defined above.

The term "aryl", as used herein, unless otherwise indicated, includes an organic radical derived from an aromatic hydrocarbon by removal of one hydrogen, such as phenyl or naphthyl, optionally substituted by 1 to 3 substituents independently selected from the group consisting of fluoro, chloro, cyano, nitro, trifluoromethyl, $(C_1-C_6)$alkoxy, $(C_6-C_{10})$aryloxy, trifluoromethoxy, difluoromethoxy, and $(C_1-C_6)$alkyl.

The term "heteroatom", as used herein, unless otherwise indicated, refers to N, S, or O.

The term "carbonyl", as used herein, unless otherwise indicated, refers to a radical of the general formula RCOR', wherein R and R' are independently alkyl, alkoxy, aryl, arylalkyl or arylalkyloxy, and the terms "alkyl" and "aryl" are as defined above. R or R' can also be —NRR'. Or R and R' can be taken together as —(CH₂)ₙ— to form a ring wherein n=3–5. In the cases where R and R' are taken together to form a ring, one or more divalent heteroatoms may be present within the ring.

A "small molecule", as used herein, refers to non-DNA, non-RNA, non polypeptide, and non-monoclonal antibody molecules with a molecular weight of under 2000 grams/mole. Preferred small molecules are carboxylic acid hydroxyamide derivatives and barbiturate derivatives. More preferred small molecules possess a hydroxamic acid group (—(C=O)(NH)OH), a heterocyclic group, a sulfonamide group, and/or an aryl group.

According to the present invention, one stereoisomer, (i.e., geometrical isomer, diastereomer, and enantiomer) may have favorable properties over another. Thus, when disclosing and claiming compounds of the invention, the stereoisomers in substantially stereo-pure form are disclosed and claimed as well. The terms geometrical isomer, diastereomer, and enantiomer as referred to herein, have the standard are recognized meanings (Cf., Hawley's condensed Chemical dictionary, 11th Ed.).

A preferred embodiment of the invention is compounds of Formula I that exhibit aggrecanase $IC_{50}$s of less than about 20 nM, preferably less than about 10 nM, as measured by an aggrecanase chondrocyte assay. More preferably the compounds further exhibit collagenase-1 $IC_{50}$s of greater than about 200 nM, even more preferably greater than about 1000 nM, as measured by a recombinant collagenase-1 assay. Most preferably, the Formula I compounds further exhibit collagenase-3 $IC_{50}$s of less than about 20 nM, preferably less than about 10 nM, as measured by a recombinant collagenase-3 assay.

In another preferred embodiment, the invention comprises compounds of Formula I that exhibit: aggrecanase $IC_{50}$s of less than about 20 nM; collagenase-1 $IC_{50}$s of greater than about 200 nM; collagenase-3 $IC_{50}$s of less than about 20 nM, and further exhibit TACE $IC_{50}$s of less than about 40 μM, preferably less than about 10 μM, as measured by a TACE whole blood assay.

In yet another embodiment, the invention comprises compounds of Formula I that exhibit: aggrecanase $IC_{50}$ of less than about 20 nM; collagenase-1 $IC_{50}$s of greater than about 200 nM; collagenase-3 $IC_{50}$s of less than about 20 nM, and further exhibit TACE $IC_{50}$s of greater than about 40 μM.

The present invention also concerns a method for treating a medical condition of the type that is characterized by the destruction of articular cartilage—preferably, joint injury, reactive arthritis, acute pyrophosphate arthritis (pseudogout), psoriatic arthritis, or juvenile rheumatoid arthritis, more preferably osteoarthritis, in a mammalian subject, preferably a human subject, which method comprises administering to the subject having said condition a therapeutically effective amount of a compound represented by Formula I. Preferably the compound of Formula I exhibits an aggrecanase $IC_{50}$ of less than about 20 nM, more preferably less than about 10 nM, as measured by an aggrecanase chondrocyte assay.

In a preferred version of this method of treatment, the compound also exhibits a collagenase-1 $IC_{50}$ of greater than about 200 nM, more preferably of greater than about 1000 nM, as measured by a recombinant collagenase-1 assay. And in an even more preferred variant of this embodiment, the compound of Formula I further exhibits a collagenase-3 $IC_{50}$ of less than about 20 nM, preferably less than about 10 nM, as measured by a recombinant collagenase-3 assay.

In another version of this treatment method, the compound of Formula I exhibits: an aggrecanase $IC_{50}$ of less than about 20 nM; a collagenase-1 $IC_{50}$ of greater than about 200 nM; and a collagenase-3 $IC_{50}$ of less than about 20 nM; and further, exhibits a TACE $IC_{50}$s of less than about 40 μM, more preferably less than about 10 μM, as measured by a TACE whole blood assay.

In yet another embodiment of this treatment method, the compound of Formula I exhibits: an aggrecanase $IC_{50}$ of less than about 20 nM; a collagenase-1 $IC_{50}$ of greater than about 200 nM; a collagenase-3 $IC_{50}$ of less than about 20 nM, and further exhibits a TACE $IC_{50}$ of greater than about 40 μM.

Yet another embodiment of the invention comprises a method for treating a medical condition of the type that is characterized by the destruction of articular cartilage—preferably, joint injury, reactive arthritis, acute pyrophosphate arthritis (pseudogout), psoriatic arthritis, or juvenile rheumatoid arthritis, more preferably osteoarthritis—in a mammalian subject, preferably a human subject, which method comprises administering to the subject having said condition a therapeutically effective amount of a compound selected from the group consisting of:

(2R,3R) 1-[4-(2,4-dichloro-benzyloxy)-benzenesulfonyl]-3-hydroxy-3-methyl-piperidine-2-carboxylic acid hydroxyamide;

(2R,5R) 1-[4-(2,4-dichloro-benzyloxy)-benzenesulfonyl]-5-hydroxy-3,3-dimethyl-piperidine-2-carboxylic acid hydroxyamide;

(2R,3S) 1-[4-(2-methyl-benzyloxy)-benzenesulfonyl]-4-aminoacetyl-3-methyl-piperazine-2-carboxylic acid hydroxyamide;

(2R,3S) 1-[4-(4-fluoro-2-methyl-benzyloxy)-benzenesulfonyl]-3-methyl-5-oxo-piperazine-2-carboxylic acid hydroxyamide;

(2R,3S) 4-[4-(2-ethyl-benzyloxy)-benzenesulfonyl]-3-methyl-4-carboxylic acid methylamide-piperazine-2-carboxylic acid hydroxyamide;

(2R,3R) 1-[4-(4-fluoro-2-methyl-benzyloxy)-benzenesulfonyl]-3-hydroxy-3-methyl-piperidine-2-carboxylic acid hydroxyamide;

(2R,5R) 1-[4-(2-chloro-4-fluoro-benzyloxy)-benzenesulfonyl]-5-hydroxy-3,3-dimethyl-piperidine-2-carboxylic acid hydroxyamide;

(2R,3S) 4-[4-(5-fluoro-2-methyl-benzyloxy)-benzenesulfonyl]-3-methyl-4-carboxylic acid methylamide-piperazine-2-carboxylic acid hydroxyamide;

(2R,3R) 1-[4-(2-chloro-4-fluoro-benzyloxy)-benzenesulfonyl]-3-hydroxy-3-methyl-piperidine-2-carboxylic acid hydroxyamide;

(2R,3R) 1-[4-(2-fluoro-4-chloro-benzyloxy)-benzenesulfonyl]-3-hydroxy-3-methylpiperidine-2-carboxylic acid hydroxyamide;

(2R,5R) 1-[4-(4-fluoro-benzyloxy)-benzenesulfonyl]-5-hydroxy-3,3-dimethyl-piperidine-2-carboxylic acid hydroxyamide;

(2R,3S) 1-[4-(2-methyl-5-fluoro-benzyloxy)-benzenesulfonyl]-3-methyl-5-oxo-piperazine-2-carboxylic acid hydroxyamide;

(2R,3S) 1-[4-(2-methyl-benzyloxy)-benzenesulfonyl]-3-hydroxy-3-methyl-piperidine-2-carboxylic acid hydroxyamide;

(2R,5R) 1-[4-(4-fluoro-2-methyl-benzyloxy)-benzenesulfonyl]-5-hydroxy-3,3-dimethyl-piperidine-2-carboxylic acid hydroxyamide;

(2R,5R) 1-[4-(2-methyl-3-fluoro-benzyloxy)-benzenesulfonyl]-5-hydroxy-3,3-dimethyl-piperidine-2-carboxylic acid hydroxyamide;

(2R,3R) 1-[4-(2-fluoro-benzyloxy)-benzenesulfonyl]-3-hydroxy-3-methyl-piperidine-2-carboxylic acid hydroxyamide;

(2R,3R) 1-[4-(2-chloro-benzyloxy)-benzenesulfonyl]-3-hydroxy-3-methyl-piperidine-2-carboxylic acid hydroxyamide;

(2R,3R) 1-[4-(2-methyl-3-fluorobenzyloxy)-benzenesulfonyl]-3-hydroxy-3-methylpiperidine-2-carboxylic acid hydroxyamide;

(2R,5R) 1-[4-(2-methyl-5-chloro-benzyloxy)-benzenesulfonyl]-5-hydroxy-3,3-dimethyl-piperidine-2-carboxylic acid hydroxyamide;

(2R,3R) 1-[4-(2-methyl-benzyloxy)-benzenesulfonyl]-3-hydroxy-3-methyl-piperidine-2-carboxylic acid hydroxyamide;

(2R,3R) 1-[4-(2,4-difluoro-benzyloxy)-benzenesulfonyl]-3-hydroxy-3-methyl-piperidine-2-carboxylic acid hydroxyamide;

(2R,5R) 1-[4-(2-fluoro-5-chloro-benzyloxy)-benzenesulfonyl]-5-hydroxy-3,3-dimethyl-piperidine-2-carboxylic acid hydroxyamide;

(2R,3R) 1-[4-(2-methyl-5-fluorobenzyloxy)-benzenesulfonyl]-3-hydroxy-3-methyl-piperidine-2-carboxylic acid hydroxyamide;

(2R,5R) 1-[4-(2-bromo-benzyloxy)-benzenesulfonyl]-5-hydroxy-3,3-dimethyl-piperidine-2-carboxylic acid hydroxyamide; and (2R,3S) 4-[4-(2,4-difluoro-benzyloxy)-benzenesulfonyl]-3-methyl-4-carboxylic acid methylamide-piperazine-2-carboxylic acid hydroxyamide.

Another embodiment of the invention relates to a method for treating a medical condition of the type that is characterized by the destruction of articular cartilage—preferably, joint injury, reactive arthritis, acute pyrophosphate arthritis (pseudogout), psoriatic arthritis, or juvenile rheumatoid arthritis, more preferably osteoarthritis—in a mammalian subject, preferably a human subject, which method comprises administering to the subject having said condition a therapeutically effective amount of a benzyloxy-aryl-sulfonyl-piperidine-carboxylic acid hydroxamide compound of the formula:

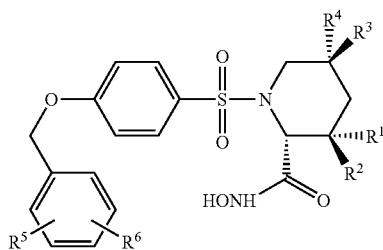

Ia or a therapeutically acceptable salt thereof, wherein
- $R^1$ and $R^2$ are independently selected from the group consisting of hydrogen, hydroxy, and methyl, wherein at least one of $R^1$ and $R^2$ is methyl;
- $R^3$ and $R^4$ are independently selected from the group consisting of hydrogen, hydroxy, and methyl;
- $R^5$ and $R^6$ are independent substituents in the ortho, meta, or para positions and are independently selected from the group consisting of hydrogen, halogen, cyano, methyl, and ethyl;
- and the compound exhibits an aggrecanase $IC_{50}$ of less than about 20 nM, said aggrecanase $IC_{50}$ measured by an aggrecanase chondrocyte assay;
- with the provisos:
  at least one of $R^1$, $R^2$, $R^3$, and $R^4$ is hydroxy; and
  when $R^5$ is para-halo, then at least one of $R^6$, $R^3$, and $R^4$ is not hydrogen.

As used herein, benzyloxy-aryl-sulfonyl-piperidine-carboxylic acid hydroxamide derivatives includes substituted derivatives and analogs. A preferred embodiment of the invention is benzyloxy-aryl-sulfonyl-piperidine-carboxylic acid hydroxamide derivatives, of the formula above, that exhibit aggrecanase $IC_{50}$s of less than about 10 nM. More preferably the benzyloxy-aryl-sulfonyl-piperidine-carboxylic acid hydroxamide compounds further exhibit collagenase-1 $IC_{50}$s of greater than about 200 nM, even more preferably greater than about 1000 nM, as measured by a recombinant collagenase-1 assay. Most preferably, the benzyloxy-arylsulfonyl-piperidine-carboxylic acid hydroxamide compounds further exhibit collagenase-3 $IC_{50}$s of less than about 20 nM, preferably less than about 10 nM, as measured by a recombinant collagenase-3 assay.

In another preferred embodiment, the benzyloxy-arylsulfonyl-piperidine-carboxylic acid hydroxamide compounds exhibit: collagenase-1 $IC_{50}$s of greater than about 200 nM; collagenase-3 $IC_{50}$s of less than about 20 nM, and further exhibit TACE $IC_{50}$s of less than about 40 μM, preferably less than about 10 μM, as measured by a TACE whole blood assay.

In yet another preferred embodiment, the benzyloxy-arylsulfonyl-piperidine-carboxylic acid hydroxamide compounds exhibit: collagenase-1 $IC_{50}$s of greater than about 200 nM; collagenase-3 $IC_{50}$s of less than about 20 nM, and further exhibit TACE $IC_{50}$s of greater than about 40 μM.

Still another embodiment of the invention concerns a method for treating a medical condition of the type that is characterized by the destruction of articular cartilage—preferably, joint injury, reactive arthritis, acute pyrophosphate arthritis (pseudogout), psoriatic arthritis, or juvenile rheumatoid arthritis, more preferably osteoarthritis—in a mammalian subject, preferably a human subject, which method comprises administering to the subject having said condition a therapeutically effective amount of a benzyloxy-aryl-sulfonyl-piperazine-carboxylic acid hydroxamide compound represented by the formula:

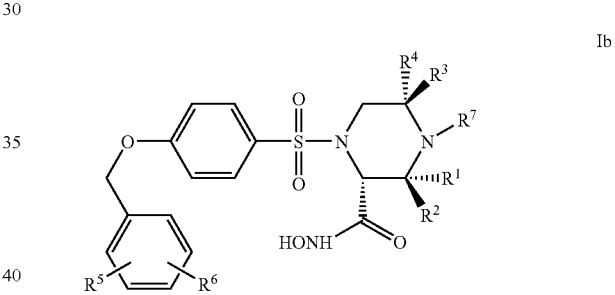

Ib or a therapeutically acceptable salt thereof, wherein
- $R^1$ and $R^2$ are independently selected from the group consisting of hydrogen, hydroxy, and methyl, wherein at least one of $R^1$ and $R^2$ is methyl;
- $R^3$ and $R^4$ are independently selected from the group consisting of hydrogen, hydroxy, and methyl, or $R^3$ and $R^4$ may be taken together to form a carbonyl group;
- $R^5$ and $R^6$ are independent substituents in the ortho, meta, or para positions and are independently selected from the group consisting of hydrogen, halogen, cyano, methyl, and ethyl; and
- $R^7$ is hydrogen or a group of the formula:

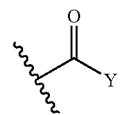

wherein, Y is —$CH_2$—$NH_2$ or —NH—$CH_3$; and
the compound exhibits an aggrecanase $IC_{50}$ of less than about 20 nM, said aggrecanase $IC_{50}$ measured by an aggrecanase chondrocyte assay;

with the proviso that when $R^7$ is hydrogen, then $R^3$ and $R^4$ are taken together to form a carbonyl group.

As used herein, benzyloxy-aryl-sulfonyl-piperiazine-carboxylic acid hydroxamide derivatives includes substituted derivatives and analogs. In a preferred embodiment of the invention, the benzyloxy-aryl-sulfonyl-piperazine-carboxylic acid hydroxamide compounds, of the above formula, exhibit an aggrecanase $IC_{50}$s of less than about 10 nM. More preferably the benzyloxy-aryl-sulfonyl-piperazine-carboxylic acid hydroxamide compounds further exhibit collagenase-1 $IC_{50}$s of greater than about 200 nM, even more preferably greater than about 1000 nM, as measured by a recombinant collagenase-1 assay. Most preferably, the benzyloxy-arylsulfonyl-piperazine-carboxylic acid hydroxamide compounds further exhibit collagenase-3 $IC_{50}$s of less than about 20 nM, more preferably less than about 10 nM, as measured by a recombinant collagenase-3 assay.

In another embodiment, the benzyloxy-aryl-sulfonyl-piperazine-carboxylic acid hydroxamide compounds exhibit: collagenase-1 $IC_{50}$s of greater than about 200 nM; collagenase-3 $IC_{50}$s of less than about 20 nM, and further exhibit TACE $IC_{50}$s of less than about 40 μM, preferably less than about 10 μM, as measured by a TACE whole blood assay.

In yet another preferred embodiment, the benzyloxy-arylsulfonyl-piperazine-carboxylic acid hydroxamide compounds exhibit: collagenase-1 $IC_{50}$s of greater than about 200 nM; collagenase-3 $IC_{50}$s of less than about 20 nM, and further exhibit TACE $IC_{50}$s of greater than about 40 μM.

In still another embodiment, the present invention relates to a method for treating a medical condition of the type that is characterized by the destruction of articular cartilage, preferably joint injury, reactive arthritis, acute pyrophosphate arthritis (pseudogout), psoriatic arthritis, osteoarthritis or juvenile rheumatoid arthritis, more preferably osteoarthritis, in a mammalian subject, preferably a human subject, which method comprises administering to the subject having said condition a therapeutically effective amount of a small molecule, wherein the small molecule exhibits an aggrecanase $IC_{50}$ of less than about 20 nM, preferably less than about 10 nM, as measured by an aggrecanase chondrocyte assay, most preferably a compound of formula I. A small molecule, as used herein, refers to non-DNA, non-RNA, non polypeptide, and non-monoclonal antibody molecules with a molecular weight of under 2000 grams/mole. Preferred small molecules are carboxylic acid hydroxyamide derivatives and barbiturate derivatives.

The present invention also relates to a method for treating a condition selected from the group consisting of inflammatory bowel disease, Crohn's disease, emphysema, acute respiratory distress syndrome, asthma, chronic obstructive pulmonary disease, Alzheimer's disease, organ transplant toxicity, cachexia, allergic reactions, allergic contact hypersensitivity, cancer (such as tumor invasion, tumor growth, tumor metastasis, solid tumor cancer, including colon cancer, breast cancer, lung cancer and prostrate cancer and hematopoietic malignancies including leukemias and lymphomas), tissue ulceration, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), congestive heart failure, myocardial infarction, stroke, cerebral ischemia, head trauma, spinal cord injury, neuro-degenerative disorders (acute and chronic), autoimmune disorders, Huntington's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, abnormal wound healing, burns, diabetes, corneal scarring, scleritis, AIDS, sepsis and septic shock in a mammal, including a human, comprising administering to said mammal an amount of a compound of formula I or a pharmaceutically acceptable salt thereof effective in treating such a condition.

Preferred carboxylic acid hydroxyamide derivatives contain a piperidine ring, such as, piperidine-2-carboxylic acid hydroxyamide derivatives; preferably, aryl-sulfonyl-piperidine-2-carboxylic acid hydroxyamide derivatives; and even more preferably, benzyloxy-aryl-sulfonyl-piperidine-2-carboxylic acid hydroxyamide derivatives.

Other preferred carboxylic acid hydroxyamide derivatives contain a piperazine ring, such as, piperazine-2-carboxylic acid hydroxyamide derivatives, more preferably aryl-sulfonyl-piperazine-2-carboxylic acid hydroxyamide derivatives, and most preferably benzyloxy-arylsulfonyl-piperazine-2-carboxylic acid hydroxyamide derivatives.

According to the above method of treatment with a small molecule, the small molecule preferably, also exhibits a collagenase-1 $IC_{50}$ of greater than about 200 nM, more preferably greater than about 1000 nM, as measured by a recombinant collagenase-1 assay; and even more preferably, the small molecule further exhibits a collagenase-3 $IC_{50}$ of less than about 20 nM, preferably less than about 10 nM, as measured by a recombinant collagenase-3 assay.

In another version of the above method of treatment with a small molecule, the small molecule exhibits: an aggrecanase $IC_{50}$ of less than about 20 nM; a collagenase-1 $IC_{50}$ of greater than about 200 nM; a collagenase-3 $IC_{50}$ of less than about 20 nM, and further, the small molecule exhibits a TACE $IC_{50}$ of less than about 40 μM, preferably less than about 10 μM, as measured by a TACE whole blood assay.

In yet another embodiment of the above method of treatment with a small molecule, the small molecule exhibits: an aggrecanase $IC_{50}$ of less than about 20 nM; a collagenase-1 $IC_{50}$ of greater than about 200 nM; a collagenase-3 $IC_{50}$ of less than about 20 nM, and further, the small molecule exhibits a TACE $IC_{50}$ of greater than about 40 μM.

The present invention also relates to a pharmaceutical composition for the treatment of a condition of the type characterized by the destruction of articular cartilage, preferably joint injury, reactive arthritis, acute pyrophosphate arthritis (pseudogout), psoriatic arthritis, osteoarthritis or juvenile rheumatoid arthritis, more preferably osteoarthritis—in a mammalian subject, preferably a human subject, comprising an amount of a compound of formula I or a pharmaceutically acceptable salt thereof effective in such treatments and a pharmaceutically acceptable carrier.

The present invention also relates to a pharmaceutical composition for the treatment of a condition selected from the group consisting of inflammatory bowel disease, Crohn's disease, emphysema, acute respiratory distress syndrome, asthma, chronic obstructive pulmonary disease, Alzheimer's disease, organ transplant toxicity, cachexia, allergic reactions, allergic contact hypersensitivity, cancer (such as tumor invasion, tumor growth, tumor metastasis, solid tumor cancer, including colon cancer, breast cancer, lung cancer and prostrate cancer and hematopoietic malignancies including leukemias and lymphomas), tissue ulceration, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), congestive heart failure, myocardial infarction, stroke, cerebral ischemia, head trauma, spinal cord injury, neuro-degenerative disorders (acute and chronic), autoimmune disorders, Huntington's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, abnormal wound healing, burns, diabetes, corneal scarring, scleritis, AIDS, sepsis and septic shock in a mammal, including a human, comprising an amount of a compound of formula I or a pharmaceutically acceptable salt thereof effective in such treatments and a pharmaceutically acceptable carrier.

The present invention also relates to a pharmaceutical composition for the treatment of diseases characterized by metalloproteinase activity (preferably MMP-13) and other diseases characterized by mammalian reprolysin activity (preferably TACE or aggrecanase activity) in a mammal, including a human, comprising an amount of a compound of formula I or a pharmaceutically acceptable salt thereof effective in such treatments and a pharmaceutically acceptable carrier.

The present invention also relates to a pharmaceutical composition for the inhibition of (a) matrix metalloproteinases or other metalloproteinases involved in matrix degradation, or (b) a mammalian reprolysin (such as aggrecanase or ADAM's TS-1, 10, 12, 15 and 17, most preferably ADAM-17) in a mammal, including a human, comprising an effective amount of a compound of formula I or a pharmaceutically acceptable salt thereof and a pharmaceutically acceptable carrier.

The invention also encompasses chemical intermediates useful for preparing the compounds of Formula I. One such intermediate is a compound of the formula XII:

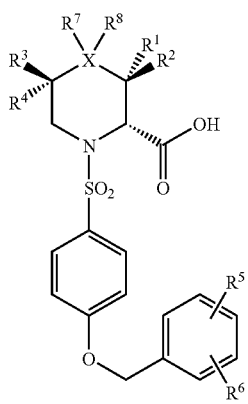

XII wherein, X is carbon and $R^7$ and $R^8$ are hydrogen, and $R^1$, $R^2$, $R^3$, and $R^4$ are selected from the group consisting of hydrogen, hydroxy, and methyl and $R^5$ and $R^6$ are independent substituents in the ortho, meta, or para positions and are independently selected from the group consisting of hydrogen, halogen, cyano, methyl, and ethyl.

Another such intermediate is compound XIII represented by the formula:

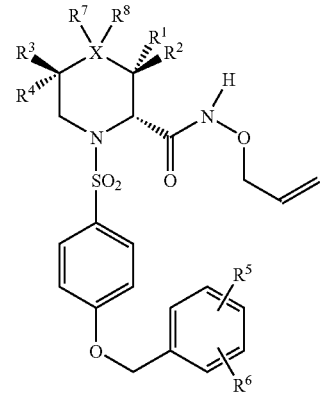

XIII wherein X is carbon, $R^7$ and $R^8$ are hydrogen, and $R^1$, $R^2$, $R^3$, and $R^4$ are selected from the group consisting of hydrogen, hydroxy, and methyl and $R^5$ and $R^6$ are independent substituents in the ortho, meta, or para positions and are independently selected from the group consisting of hydrogen, halogen, cyano, methyl, and ethyl.

Still another intermediate useful for the synthesis of compounds of Formula I is compound XIX represented by the formula:

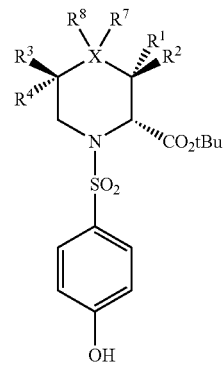

XIX wherein X is carbon, $R^7$ and $R^8$ are hydrogen, $R^1$, $R^2$, $R^3$, and $R^4$ are independently selected from the group consisting of hydrogen, hydroxy, and methyl.

Another intermediate is a compound XXVIII represented by the formula:

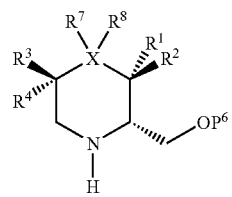

XXVIII wherein X is carbon and $R^7$ and $R^8$ are hydrogen, and $R^1$, $R^2$, $R^3$, and $R^4$ are independently selected from the group consisting of hydrogen, hydroxy, and methyl and $P^6$ is hydrogen or a silyl group. Preferably, one of $R^1$, $R^2$, $R^3$, and $R^4$ is hydroxy and one of $R^1$, $R^2$, $R^3$, and $R^4$ is alkyl, preferably methyl. Alternatively, one of $R^1$ and $R^4$ is hydroxy and one of $R^1$ and $R^4$ is alkyl, preferably methyl. In another embodiment of intermediate XXVIII, one of $R^2$ and $R^3$ is hydroxy and one of $R^2$ and $R^3$ is alkyl, preferably methyl. Alternatively, one of $R^3$ and $R^4$ is hydroxy and one of $R^3$ and $R^4$ is alkyl, preferably methyl. In another embodiment of intermediate XXVIII, one of $R^1$ and $R^2$ is alkyl, preferably methyl and one of $R^1$ and $R^2$ is hydroxy.

Yet another intermediate is a compound represented by the formula:

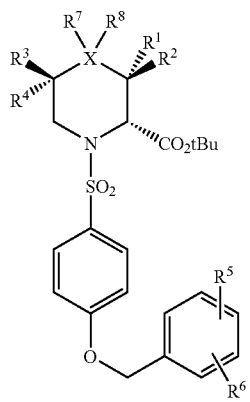

XX wherein X is carbon, $R^7$ and $R^8$ are hydrogen, $R^1$, $R^2$, $R^3$, and $R^4$ are independently selected from the group consisting of hydrogen, hydroxy, and methyl, and $R^5$ and $R^6$ are independent substituents in the ortho, meta, or para positions and are independently selected from the group consisting of hydrogen, halogen, cyano, methyl, and ethyl.

A further intermediate useful for the synthesis of compounds of Formula I is compound XXXV represented by the formula:

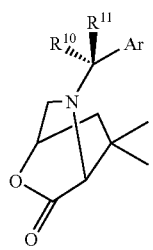

XXXV wherein Ar is phenyl or phenyl substituted by one or more groups and $R^{10}$ and $R^{11}$ are independently selected from the group consisting of hydrogen, aryl, and $(C_1-C_6)$alkyl. Preferably one of $R^{10}$ and $R^{11}$ is hydrogen and one of $R^{10}$ and $R^{11}$ is methyl, and Ar is phenyl.

Other useful intermediates are the two compounds represented by the formulas below:

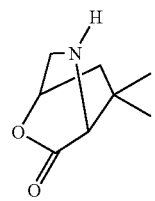

XXXVI

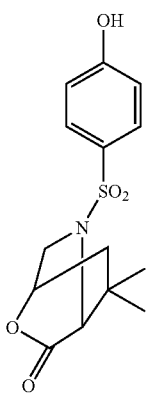

XXXVIII

A further intermediate useful for the synthesis of compounds of Formula I is compound XXXIX represented by the formula:

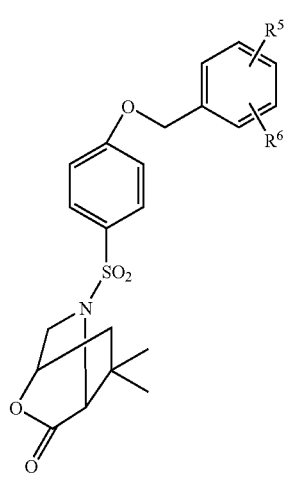

XXXIX wherein $R^5$ and $R^6$ are independent substituents in the ortho, meta, or para positions and are independently selected from the group consisting of hydrogen, halogen, cyano, methyl, and ethyl.

Other intermediates, useful for the preparation of the compounds of Formula I are described in the General Methods To Prepare Compounds Of Formula I Section.

All of the intermediates described herein, may be made in isotopically-labeled form, which intermediates are identical to those recited above, but for the fact that one or more atoms are replaced by an atom having an atomic mass or mass number different from the atomic mass or mass number usually found in nature. Examples of isotopes that can be incorporated into the intermediates of the invention include isotopes of hydrogen, carbon, nitrogen, oxygen, phosphorous, fluorine and chlorine, such as $^{2}$H, $^{3}$H, $^{13}$C, $^{14}$C, $^{15}$N, $^{18}$O, $^{17}$O, $^{31}$P, $^{32}$P, $^{35}$S, $^{18}$F, and $^{36}$Cl, respectively.

The synthetic intermediates of the present invention may also be related to prodrugs of the Formula I compounds. That is, the intermediates described herein may be substituted with other groups or protecting groups or their syntheses otherwise altered in a manner well known by those skilled in the art to arrive at the desired formula I prodrug.

One skilled in the art will also appreciate that when using the compounds of the invention in the treatment of a specific disease that the compounds of the invention may be adjunctively administered with various existing therapeutic agents used for that disease.

For the treatment of rheumatoid arthritis, the compounds of the invention may be combined with agents, such as, TNF-α inhibitors, such as, anti-TNF monoclonal antibodies (such as Remicade®) and TNF receptor immunoglobulin molecules (such as Enbrel®), low dose methotrexate, lefunimide, hydroxychloroquine, d-penicilamine, auranofin or parenteral oral gold.

The compounds of the invention can also be used with existing therapeutic agents for the treatment of osteoarthritis. Suitable compounds that can be used with the compounds of the invention include but are not limited to standard non-steroidal anti-inflammatory compounds, such as, piroxicam, diclofenac, propionic acids, such as, naproxen, flubiprofen, fenoprofen, ketoprofen, and ibuprofen; fenamates, such as, mefenamic acid, indomethacin, sulindac, apazone, pyrazolones, such as, phenylbutazone, salicylates, such as, aspirin; COX-2 inhibitors, such as, celecoxib, valdecoxib, paracoxib and rofecoxib; analgesics, LTD-4, LTB-4 and 5-LO inhibitors, p38 kinase inhibitors and intraarticular therapies, such as, corticosteroids and hyaluronic acids, such as, hyalgan and synvisc.

The compounds of the present invention may also be used in combination with anticancer agents, such as, endostatin and angiostatin or cytotoxic drugs, such as, adriamycin, daunomycin, cis-platinum, etoposide, taxol, taxotere, and alkaloids, such as, vincristine, and antimetabolites, such as, methotrexate.

The compounds of the present invention may also be used in combination with cardiovascular agents, such as, calcium channel blockers, lipid lowering agents, such as, statins, fibrates, beta-blockers, Ace inhibitors, Angiotensin-2 receptor antagonists and platelet aggregation inhibitors.

The compounds of the present invention may also be used in combination with CNS agents, such as, antidepressants (like sertraline), anti-Parkinsonian drugs (such as deprenyl, L-dopa, Requip, Mirapex, MAOB inhibitors, such as, selegiline and rasagiline; comP inhibitors, such as, Tasmar, A-2 inhibitors, dopamine reuptake inhibitors, NMDA antagonists, Nicotine agonists, NK-1 inhibitors, Dopamine agonists and inhibitors of neuronal nitric oxide synthase), and anti-Alzheimer's drugs, such as, donepezil, tacrine, COX-2 inhibitors, propentofylline or metryfonate.

The compounds of the present invention may also be used in combination with osteoporosis agents, such as, roloxifene, droloxifene, lasofoxifene or fosomax, and immunosuppressant agents, such as, FK-506 and rapamycin.

These and other features, aspects, and advantages of the present invention will become better understood with regard to the following detailed description, appended claims, and accompanying drawings.

DETAILED DESCRIPTION OF THE INVENTION

The following reaction Schemes illustrate the preparation of the compounds of the present invention. Unless otherwise specified, $R^{1}$, $R^{2}$, $R^{3}$, $R^{4}$, $R^{5}$, $R^{6}$, $R^{7}$, and $R^{8}$ in the reaction Schemes and in the discussion and examples that follow are defined as above.

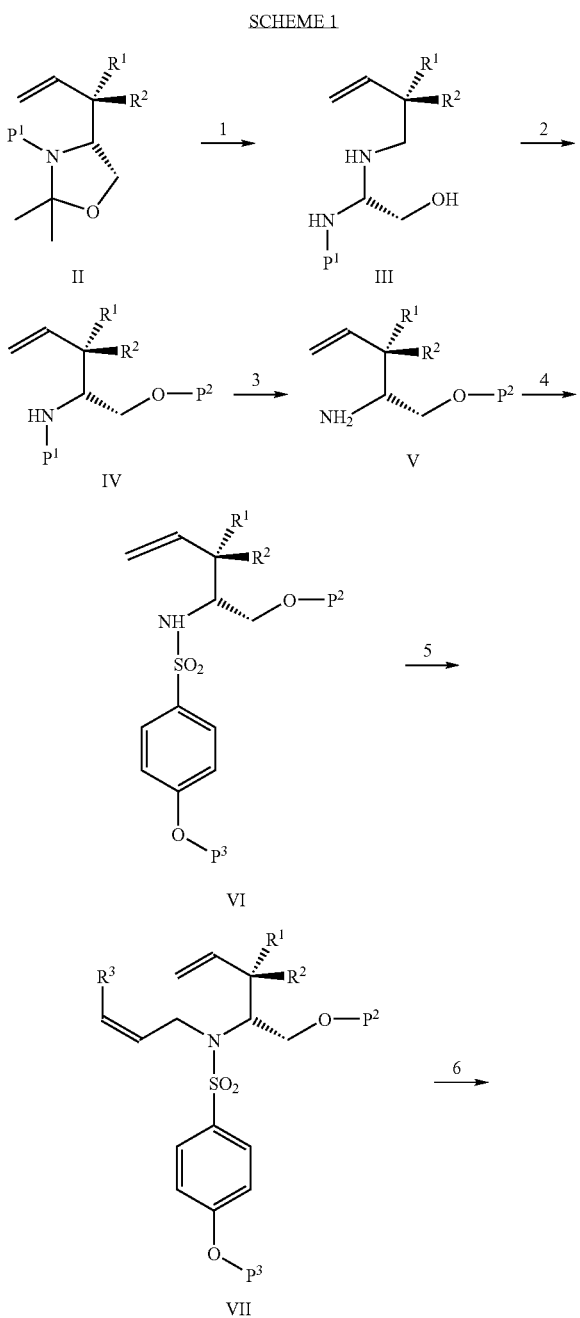

-continued
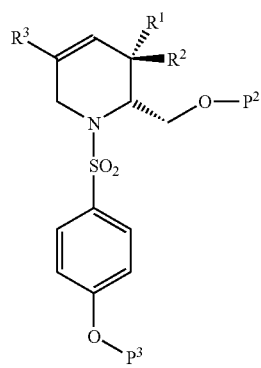
VIII
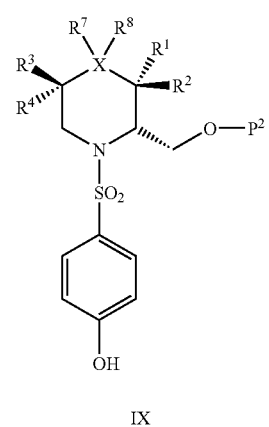
IX
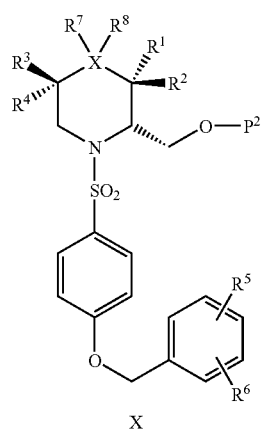
X
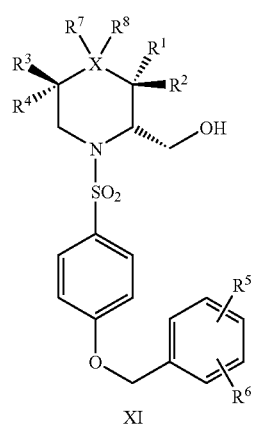
XI
-continued
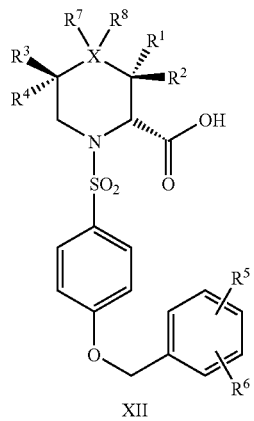
XII
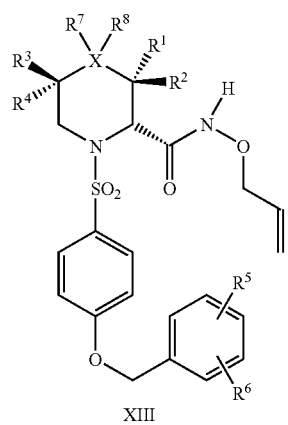
XIII
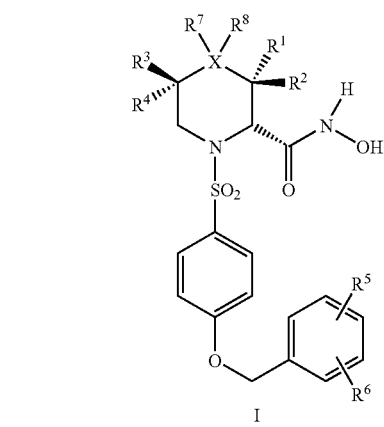
I

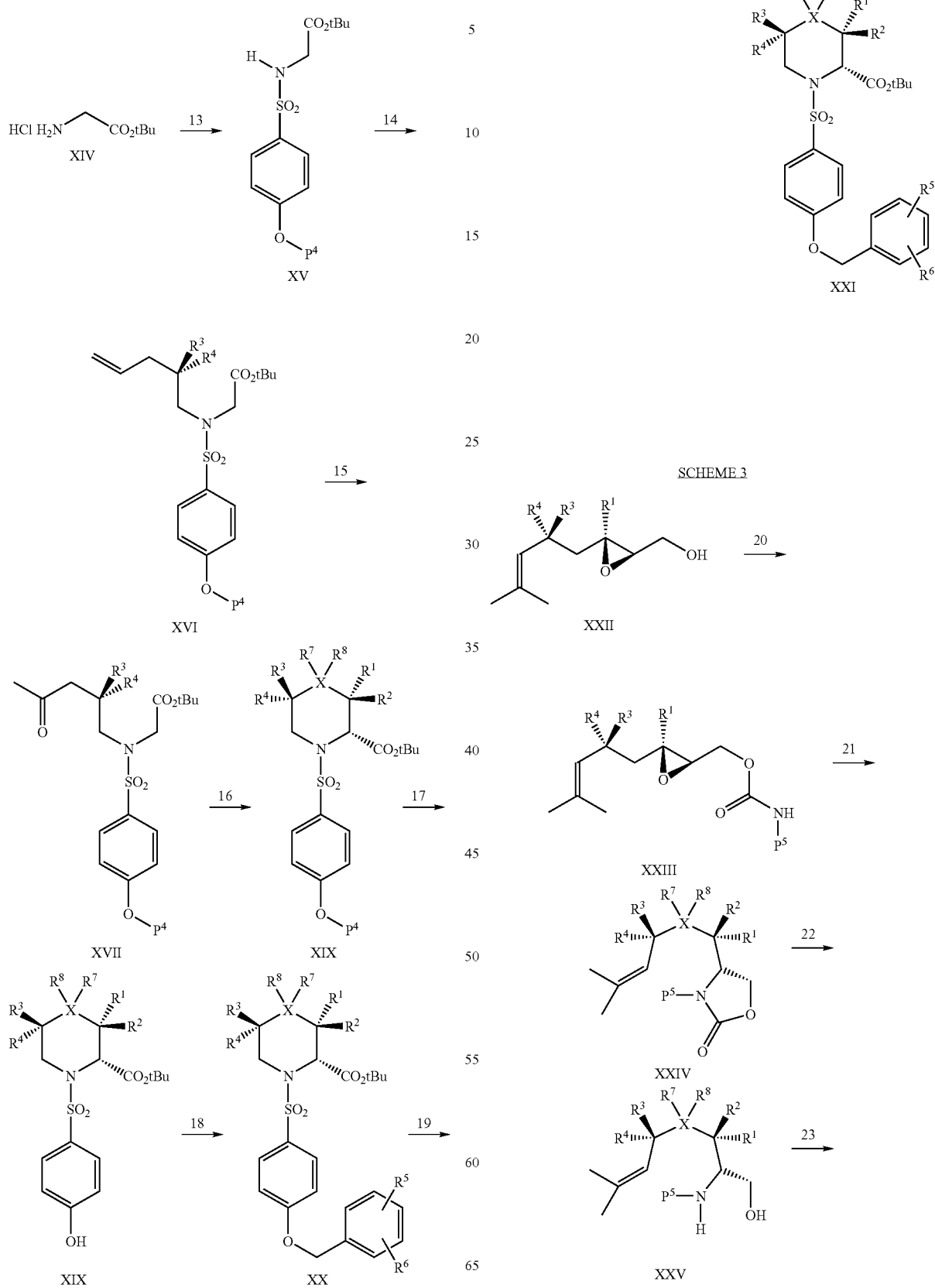

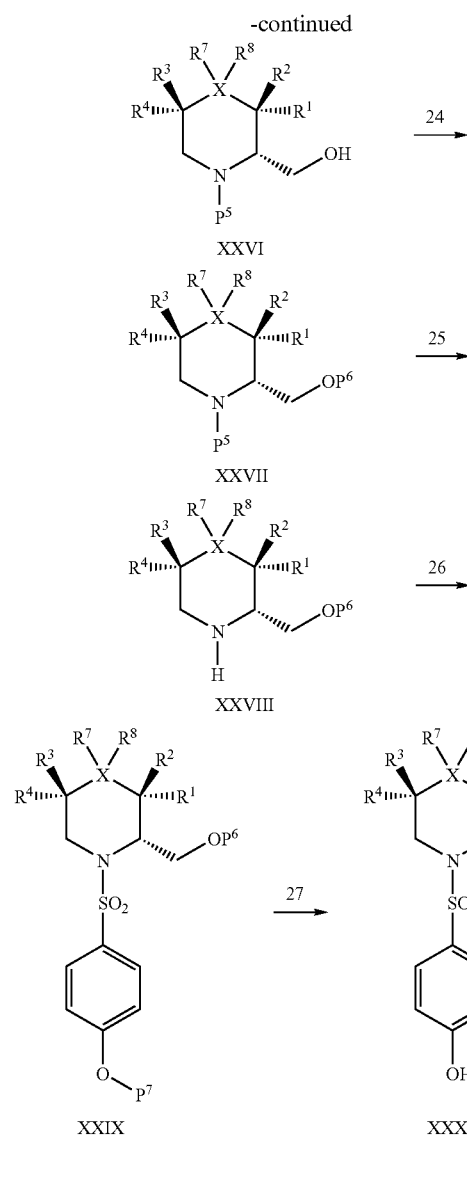
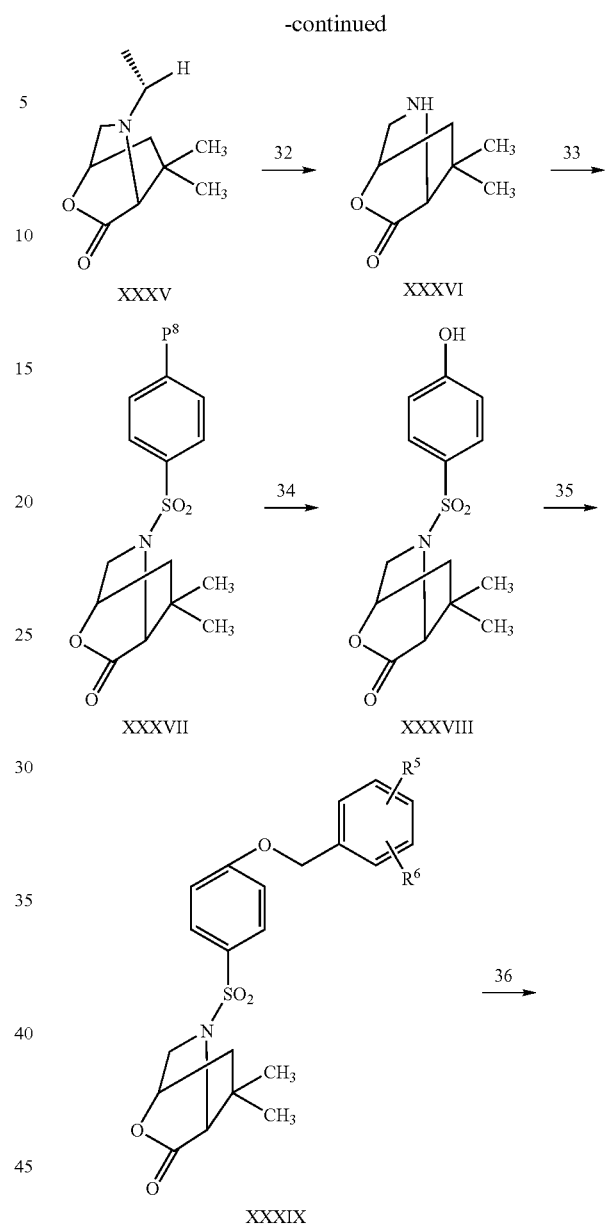
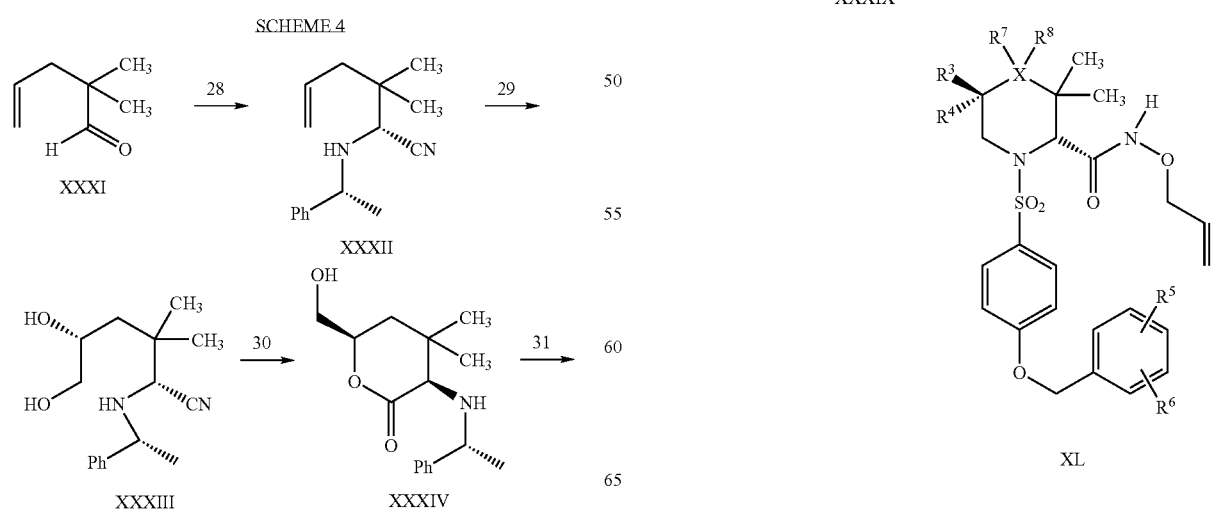

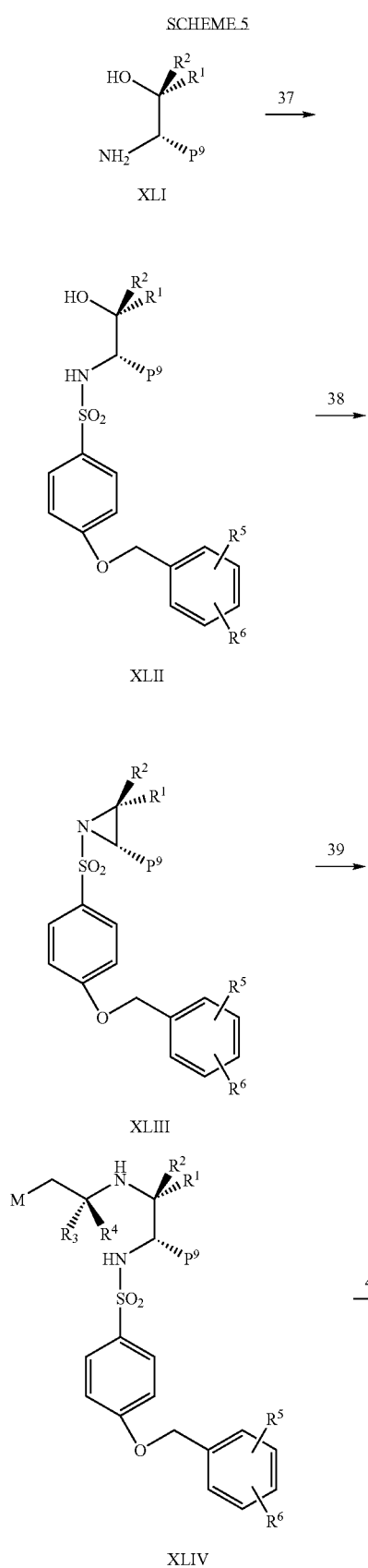
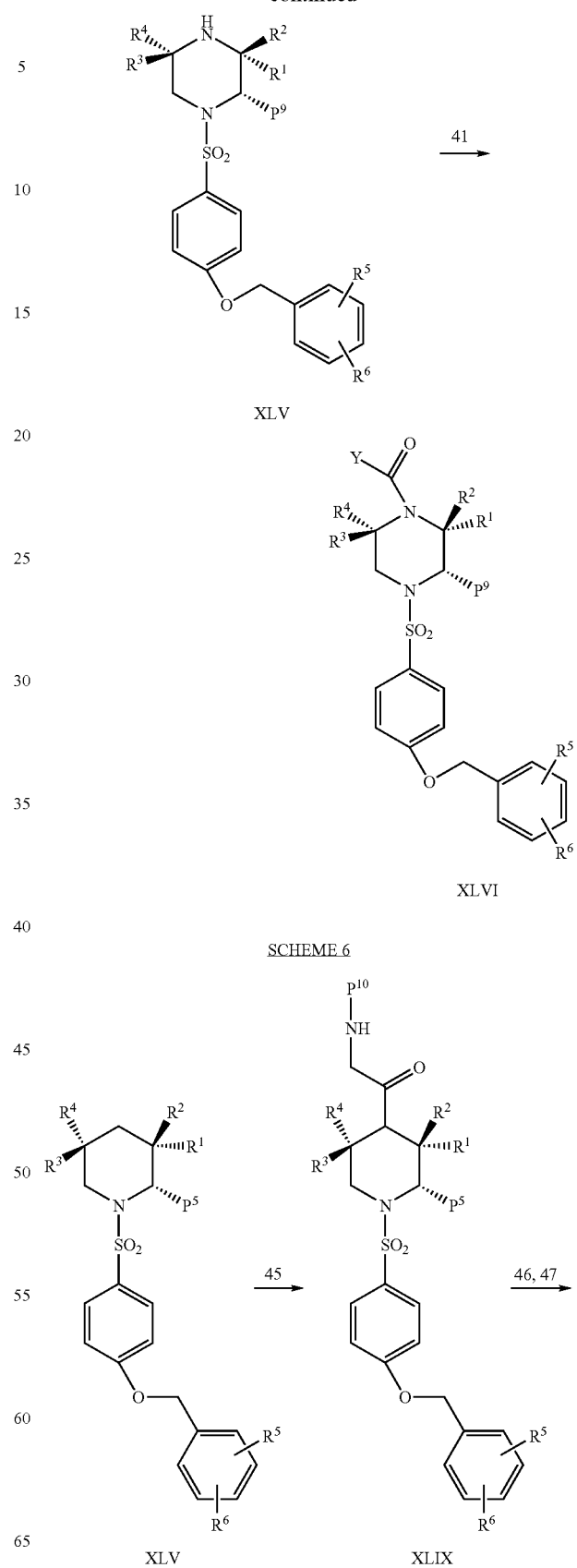

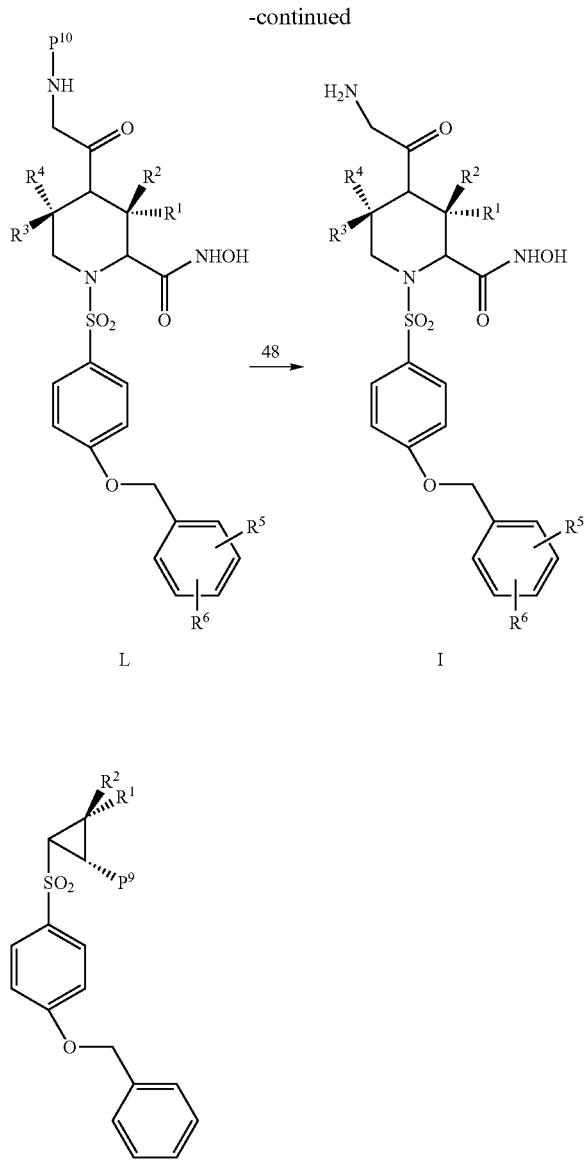

Scheme 1 discloses the general methodology to prepare compounds of Formula I, wherein X is carbon and $R^3$, $R^4$, $R^7$, and $R^8$ are each hydrogen, and $R^1$, $R^2$, $R^5$, and $R^6$ are as above.

One skilled in the art will understand that the compounds of Formula I possess chiral centers and the compounds of Formula II can be prepared in any desired stereoisomeric form or purity according to the method of Ageno, G. et al., V. *Tetrahedron*, 1995, 29, 8121 and references cited therein (incorporated herein by reference). Referring to Scheme 1, In Step 1, a compound of formula III, wherein $P^1$ is a protecting group, preferably an alkyloxy carbonyl group, most preferably butyloxycarbonyl, may be prepared by treating a compound of formula II, wherein $P^1$ is as defined above, with a suitably strong acid, such as, a sulfonic acid, preferably p-toluenesulfonic acid in an alcoholic solvent, such as, methanol at a temperature of about 0° C. to 50° C., preferably at a temperature of about 20° C. to about 25° C., preferably about 23° C., for a period of time sufficient to effect conversion.

According to Step 2 of Scheme 1, a compound of formula IV, wherein $P^2$ is a protecting group, preferably a silyl group substituted with aryl or alkyl groups, most preferably tert-butyldiphenyl silane, may be prepared by treating a compound of formula III with a silylating agent, preferably tert-butyldiphenylsilyl chloride (TBDPS-CI) in the presence of an amine, preferably imidazole, in a polar aprotic solvent, preferably dimethylformamide at a temperature of about 0° C. to about 50° C., preferably at a temperature of about 20° C. to about 25° C., preferably about 23° C., for a period of time sufficient to effect consumption of a compound of formula III.

As shown in Step 3, a compound of formula V may be prepared by treatment of a compound of formula IV with a suitable acid, for example when $P^1$ is t-butyloxy carbonyl, trifluoroacetic acid is used in a suitable solvent, such as an aprotic solvent, preferably methylene chloride at a temperature of about 0° C. to about 20° C. to about 25° C., preferably about 23° C. for about 1 to about 6 hours.

According to Step 4, a compound of formula VI, wherein $P^3$ is a protecting group, preferably methylene aryl, most preferably benzyl, may be prepared by treatment of a compound of formula V with about 2 to about 2.5 equivalents of a benzyloxyarylsulfonyl halide. The benzyloxy sulfonyl halide is preferably according to the formula below.

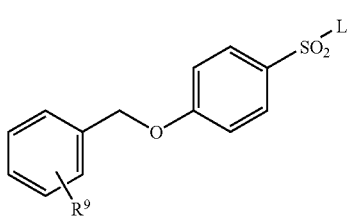

wherein group L is a halide selected from chloro and bromo and $R^9$ is H or methyl, in a polar solvent, preferably dimethylformamide at about −10° C. to about 23° C. for about 1 to about 12 hours.

Such benzyloxyarylsulfonyl halides are commercially available or can be made by methods well known to one of ordinary skill in the art, e.g., PCT publication WO 98/07697.

As is readily apparent to one of skill in the art, in Step 4, the benzyloxyaryl halide can also be according to the formula:

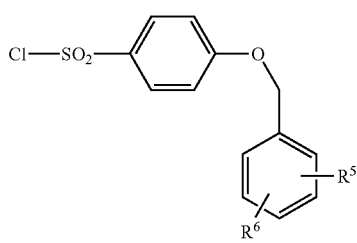

wherein $R^5$ and $R^6$ are as above. As one of skill in the art would recognize, use of this intermediate, wherein the $R^5$ and $R^6$ groups are as desired in the final product, obviates Steps 7 and 8.

As shown in Step 5, a compound of formula VII may be prepared by treatment of a compound of formula VI with a suitable allylic halide, preferably allyl bromide, in the presence of a suitably strong base, such as, a carbonate base, preferably cesium carbonate, in a polar solvent, preferably an aprotic solvent, most preferably dimethylformamide at a temperature of about 0° C. to about 100° C., preferably at a temperature of about 20° C. to about 25° C., preferably about 23° C. for a period of time necessary to effect complete conversion. If necessary, a metal halide salt, such as an iodide salt, preferably potassium iodide, may be added.

According to Step 6, a compound of formula VIII may be prepared by treatment of a compound of formula VII with a catalytic amount of a ruthenium catalyst, preferably bis (tricyclohexylphosphine)benzylidine ruthenium (IV) dichloride in a nonpolar solvent, such as methylene chloride, in the presence of a stoichiometric amount of diallylether at a temperature of about 23° C. to about 80° C., most preferably about 50° C. for about 4 to about 24 hours.

According to Step 7, a compound of formula IX may be prepared by deprotection of a compound of formula VIII. When $P^3$ is methylene aryl, deprotection is preferably accomplished with hydrogen gas at a pressure between ambient and about 80 psi, in the presence of a catalyst, such as palladium on charcoal, in a polar solvent, preferably methanol or ethanol, at a temperature of about 20° C. to about 25° C., preferably about 23° C. for a period of time necessary to effect conversion.

According to Step 8 of Scheme 1, a compound of formula X may be prepared by treatment of a compound of formula IX with an appropriately substituted benzylhalide according to the formula:

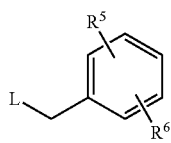

wherein, $R^5$ and $R^6$ are as above, L is a leaving group, preferably Cl or Br, in the presence of a suitably strong base, such as a carbonate base, preferably cesium carbonate, in a polar solvent, preferably an aprotic solvent, most preferably dimethylformamide at a temperature of about 0° C. to about 100° C., preferably about 23° C.

As shown in Step 9, a compound of formula X is converted to a compound of formula XI by removal of protecting group $P^2$. When $P^2$ is a silyl group, deprotection is preferably accomplished with an activated fluoride source, such as a tetraalkylammonium fluoride, preferably tetrabutylammonium fluoride (1–3 equivalents) in a polar aprotic solvent, preferably tetrahydrofuran at a temperature of about 0° C. to about 25° C., preferably about 23° C. for about 1 to about 6 hours.

According to Step 10, a compound of formula XII may be prepared by treatment of a compound of formula XI with a catalytic amount of chromium trioxide and a stoichiometric amount of periodic acid as described by Zhao, M. et al., *Tetrahedron Lett.* 1998, 39, 5323.

According to Step 11, a compound of formula XIII, wherein X is carbon and $R^3$, $R^4$, $R^7$, and $R^8$ are each hydrogen, may be prepared by treating a compound of formula XII with a hydroxylamine ether, preferably O-allylhydroxylamine, in the presence of a coupling agent, preferably a carbodiimide, most preferably 1-(3-dimethylaminopropyl)-3-ethylcarbodiimide hydrochloride (EDC) or 1-hydroxybenzotriazole hydrate (HOBT) in an inert solvent, such as tetrahydrofuran or methylene chloride, preferably tetrahydrofuran at about 0° C. to about 40° C., preferably about 25° C. for about 2 to about 48 hours.

Finally in Step 12 of Scheme 1, a compound of Formula I, wherein X is carbon and $R^3$, $R^4$, $R^7$, and $R^8$ are each hydrogen, may be prepared by treating a compound of formula XIII with a reducing agent, such as triethylammonium formate and a catalytic amount of a palladium [0] salt, preferably palladium tetrakistriphenylphosphine in a polar solvent, preferably 20% water in acetonitrile, at about 20° C. to about 110° C., preferably about 80° C. for about 15 to about 90 minutes.

Scheme 2 describes a preparation method for a compound of the formula XXI— wherein X is carbon, $R^3$, $R^4$, $R^7$, and $R^8$ are hydrogen, one of $R^1$ and $R^2$ is hydroxy, one of $R^1$ and $R^2$ is methyl, and $R^5$, and $R^6$ are as above. A compound of formula XXI can be converted into a compound of Formula I, wherein X is carbon, $R^3$, $R^4$, $R^7$, and $R^8$ are hydrogen, one of $R^1$ and $R^2$ is hydroxy, one of $R^1$ and $R^2$ is methyl, and $R^5$ and $R^6$ are as above by treatment of a compound XXI according to Steps 11 and 12 of Scheme 1.

This methodology is more expedient than that of Scheme I, however, this methodology is not suitable for preparation of (2R,3R)-Formula I compounds wherein $R^2$ is hydroxy, $R^1$ is methyl, and one of $R^5$ or $R^6$ is alkyl.

Referring to Scheme 2, compound a compound of formula XV, wherein the protecting group, $P^4$, is preferably methylene aryl, most preferably benzyl substituted with $R^9$, wherein $R^9$ hydrogen or methyl—is prepared, according to Step 13, by treatment of glycine tert butyl ester hydrochloride salt (XIV) with a benzyloxyaryl halide. Preferably the benzyloxyaryl halide is according to the Formula:

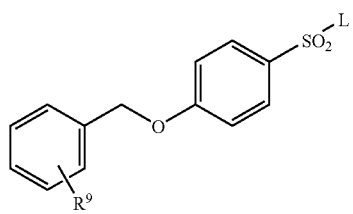

which compounds are commercially available or can be made by methods well known to one of ordinary skill in the art, e.g., PCT publication WO 98/07697 (incorporated herein by reference)—and a base in the presence of a solvent. Group L is a halide selected from chloro and bromo and $R^9$ is H or methyl. Suitable bases include trialkylamine or pyridine and suitable solvents include N,N-dimethylformamide or dichloromethane. The aforesaid reaction is run for a period of time of from about 0.5 to about 20 hours, preferably of from about 1 to about 3 hours, at a temperature of from about 0° C. to about 50° C.

As is readily apparent to one of skill in the art, in Step 13, the benzyloxyaryl halide can also be according to the formula:

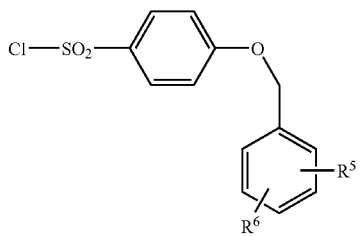

wherein $R^5$ and $R^6$ are as above. As one of skill in the art would recognize, use of this intermediate, wherein the $R^5$ and $R^6$ groups are as desired in the final product, obviates Steps 17 and 18.

According to Step 14, a compound of formula XVI may be prepared by treatment of a compound of formula XV with the appropriate alkylene halide, preferably 5-bromo-1-pentene, in the presence of a suitable base and solvent. The base is preferably a metal carbonate, such as, cesium carbonate. Also, a metal halide salt, such as an iodide, preferably potassium iodide, can be included in the reaction mixture. The solvent is preferably a polar aprotic solvent, such as, dimethylformamide and the reaction temperature is between about 23° C. and about the boiling point of the solvent, preferably about 50° C. to about 70° C. for a reaction time of about 2 to about 48 hours.

According to Step 15, a compound of formula XVII may be prepared by reaction of a compound of formula XVI under Wacker oxidation conditions. Thus, a compound of formula XVI is treated with a suitable oxidant, such as oxygen gas, in the presence of a stoichiometric amount of a copper salt, preferably cuprous chloride and a palladium catalyst, such as a palladium II catalyst, preferably palladium (II) chloride, in a suitable solvent, such as a polar solvent, most preferably a mixture of dimethylformamide and water at a temperature of between about 0° C. and about 80° C., preferably about 23° C. for about 2 to about 48 hours.

According to Step 16, a compound of formula XVIII. wherein one of $R^1$ and $R^2$ is methyl, may be prepared from a compound of formula XVII by reaction with a suitable base such as a sodium or potassium alkoxide or a lithium, sodium or potassium dialkylamide, preferably potassium tert-butoxide. Preferably, the aforesaid reaction is run in the presence of a solvent, such as, a dialkyl ether, toluene, alcohols (such as, those corresponding to the alkoxide base), or tetrahydrofuran, preferably tetrahydrofuran. The aforesaid reaction is run at a temperature of from −78° C. to about the boiling point of the solvent, preferably at about 0° C. to about 23° C., for a period of from about 30 minutes to about 24 hours.

As outlined in Step 17 and 18, one $(R^5, R^6)$-benzyl group can replace another $(R^5, R^6)$-benzyl group so as to facilitate the preparation of additional analogs. In Step 17, a compound of formula XIX may be prepared by deprotection of a compound of formula XVIII. When $P^4$ is methylene aryl, deprotection is preferably accomplished by treating XVIII with hydrogen gas at a pressure between ambient and about 80 psi in the presence of a catalyst, such as palladium on charcoal, in a polar solvent, such as methanol or ethanol, preferably a 1:1 mixture of methanol and ethyl acetate, at a temperature of about 20° C. to about 25° C., preferably about 23° C. for a period of time necessary to effect complete reaction (e.g., about 2 hours).

By the method outlined in Step 18 of Scheme 2, a compound of formula XX may be prepared by treatment of a compound of formula XIX with the appropriately substituted benzylhalide according to formula:

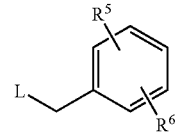

wherein L is preferably Cl or Br, in the presence of a suitably strong base, such as a carbonate base, preferably cesium carbonate, in a polar solvent, preferably an aprotic solvent, most preferably dimethylformamide at a temperature of about 0° C. to about 100° C. As shown in Step 19, a compound of formula XXI is prepared from a compound of formula XX by reaction with a suitable acid, such as trifluoroacetic acid, in a suitable solvent, such as a chlorinated hydrocarbon, preferably methylene chloride at a temperature of from about −20° C. to about the boiling point of the solvent, preferably about 0° C. to about 23° C. for a period of from about 30 minutes to about 4 hours.

Compounds XXI may then be converted into the compounds of Formula 1—wherein X is carbon, $R^3$, $R^4$, $R^7$, and $R^8$ are hydrogen, and one $R^1$ and $R^2$ is hydroxy and one of $R^1$ and $R^2$ is methyl and, $R^5$, and $R^6$ are as above according to Steps 11 and 12 of Scheme I.

Scheme 3 illustrates an alternate method for the preparation of a compound of formula XXX, wherein X is carbon, $R^3$, $R^4$, $R^7$, and $R^8$ are hydrogen, and one of $R^1$ and $R^2$ is hydroxy (otherwise $R^1$ and $R^2$ are as defined above). The protecting group, $P^6$, is preferably a tetra-substituted silane group, most preferably tertbutyldiphenyl silane. A compound of formula XXX can be converted into a compound of Formula I, wherein X is carbon, $R^3$, $R^4$, $R^7$, and $R^8$ are hydrogen, $R^2$ is hydroxy and $R^1$, $R^5$, and $R^6$ are as above via treatment of compound XXX according to Steps 8 through 12 of Scheme 1.

Referring to Scheme 3, the cis-epoxide XXII may be prepared, in either stereoisomeric form or as the racemate, according to the method of Sharpless et al. *J. Amer. Chem Soc.*, 1987, 109, 5765.

In Step 20, a compound of formula XXIII, wherein $P^5$ is a protecting group, preferably methylene aryl, most preferably benzyl, may be prepared by treating the compound of formula XXII with an isocyanate, such as an alkyl or aryl isocyanate, preferably benzyl isocyanate, in an inert solvent, such as methylene chloride, in the presence of a tertiary amine base, such as a trialkylamine base, preferably triethylamine, between about 0° C. and about 50° C., preferably about 23° C. for a period of time sufficient to effect complete conversion, typically about 2 to about 24 hours.

In Step 21, a compound of formula XXIV, wherein $R^2$ is hydroxy, may be prepared by treatment of a compound of formula XXIII with a suitably strong base, such as a hydride base or an alkoxide base, preferably sodium hydride in a suitable solvent, such as an aprotic solvent, preferably tetrahydrofuran at a temperature of about 0° C. to about 20° C. to about 25° C. for about 2 to about 24 hours.

In Step 22 of Scheme 3, a compound of formula XXV may be prepared by treatment of a compound of formula XXIV with a suitably strong base, such as a hydroxide base, preferably potassium hydroxide, in a polar solvent, such as a mixture of an alcohol and water, preferably a mixture of ethanol and water, at a temperature of between about 50° C. and about the boiling point of the mixture, preferably about 120° C. for about 4 to about 24 hours.

In Step 23 of Scheme 3, a compound of formula XXVI may be prepared by treatment of a compound of formula XXV with a suitable oxidant, such as ozone, in a suitable solvent, preferably a mixture of methanol, and methylene chloride, containing an equivalent of a suitably strong acid, such as sulfuric or hydrochloric acid, preferable hydrochloric acid, at a temperature of between about 0° C. about −80° C., preferably about −78° C., for about 5 to about 60 minutes. The mixture is then treated with a large excess of a suitable reducing agent, such as an alkyl sulfide, preferably methyl sulfide, and is warmed to about 0° C. over a period of time necessary to effect complete reduction of the ozonide. After concentration and extractive isolation, the material is treated with a suitable reducing agent, such as a borohydride, preferably sodium triacetoxyborohydride, in a suitable solvent, such as a polar solvent, preferably dichloromethane, at a temperature between about 0° C. and about the solvent's boiling point, preferably about 23° C. for about 1 to about 24 hours.

In Step 24 of Scheme 3, a compound of formula XXVII, wherein the protecting group, $P^6$, is preferably a silyl group, more preferably tert-butyldimethylsilyl, may be prepared by treatment of a compound of formula XXVI with an appropriate silylating agent and an amine base, preferably imidazole, in a polar aprotic solvent, preferably dimethylformamide, at a temperature between about 0° C. and about 40° C., preferably about 23° C. for about 1 to about 24 hours.

In Step 25 of Scheme 3, a compound of formula XXVIII may be prepared by removal of protecting group $P^5$ from a compound of formula XXVII. If $P^5$ is methylene aryl, then a compound of formula XXVII is preferably deprotected with hydrogen gas at a pressure between about ambient pressure and about 80 psi in the presence of a catalyst, such as palladium on charcoal, in a polar solvent, preferably methanol or ethanol at a temperature of about 20° C. to about 25° C., preferably about 23° C. for a period of time necessary to effect conversion.

In Step 26 of Scheme 3, a compound of formula XXIX, wherein $P^7$ is a protecting group, preferably a methylenearyl group, most preferably a benzyl group or methyl benzyl group, may be prepared by treatment of a compound of formula XXVIII with a benzyloxyaryl halide. Preferably the benzyloxy aryl halide is according to the Formula:

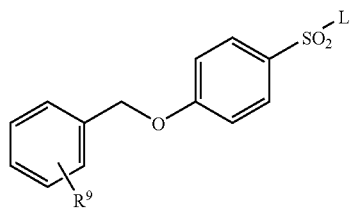

which compounds are commercially available or can be made by methods well known to one of ordinary skill in the art, e.g., PCT publication WO 98/07697 and a base in the presence of a solvent. Group L is a halide selected from chloro and bromo and $R^9$ is H or methyl. Suitable bases include trialkylamine or a pyridine base. Suitable solvents include N,N-dimethylformamide or dichloromethane. The aforesaid reaction is run for a period of time from about 0.5 to about 20 hours, preferably from about 1 to about 3 hours, at a temperature from about 0° C. to about 50° C.

As is readily apparent to one of skill in the art, in Step 26, the benzyloxyaryl halide can also be according to the formula:

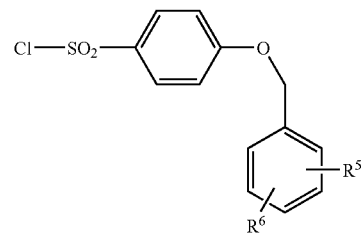

wherein $R^5$ and $R^6$ are as above. As one of skill in the art would recognize, use of this intermediate, wherein the $R^5$ and $R^6$ groups are as desired in the final product, obviates Steps 27 and a subsequent benzylation step.

In Step 27 of Scheme 3, a compound of formula XXX, which is similar in structure to intermediate IX, may be prepared by removal of the protecting group $P^7$ from a compound of formula XXIX. When $P^7$ is methylene aryl, deprotection is preferably accomplished by treating XXX with hydrogen gas at a pressure between ambient and about 80 psi in the presence of a catalyst, such as palladium on charcoal, in a polar solvent, preferably methanol or ethanol at a temperature of about 0° C. to about 25° C., preferably about 23° C. for a period of time necessary to effect conversion.

Compounds of formula XXX may be converted into compounds of Formula I, wherein X is carbon, $R^3$, $R^4$, $R^7$, and $R^8$ are hydrogen, and one of $R^1$ and $R^2$ is hydroxy (otherwise $R^1$ and $R^2$ are as defined above), and $R^5$ and $R^6$ are as above—by the general methods outlined in Scheme 1 (i.e., Steps 8–12).

Scheme 4 refers to the preparation of 3,3-dimethyl compounds of formula XL, wherein X is carbon; $R^7$, and $R^8$ are hydrogen; $R^1$ and $R^2$ are methyl; one of $R^3$ and $R^4$ is hydroxy (otherwise $R^3$ and $R^4$ have the meanings as above); and $R^5$ and $R^6$ are as above. A compound of formula XL can be converted into a compound of Formula I, wherein X is carbon; $R^3$, $R^7$, and $R^8$ are hydrogen; $R^1$ and $R^2$ are methyl; $R^4$ is hydroxy; and $R^5$ and $R^6$ are as above via treatment of compound of formula XL according to Step 12 of Scheme 1.

Referring to Scheme 4, Step 28, a compound of formula XXXII may be prepared from a compound of formula XXXI (commercially available from, for example, Aldrich Chemical Corporation) by reaction with a suitable benzylic amine of suitable (R)- or (S)-configuration at the benzylic center, preferably (R)- or (S)-α-methylbenzylamine, in the presence of a stoichiometric amount of a cyanide salt, preferably potassium cyanide, in a polar solvent, such as an alcoholic solvent, preferably methanol, at a temperature of about 0° C. to about 40° C., preferably about 0° C. to about 23° C. for about 4 to about 48 hours. Optically pure XXXII is obtained by crystallization.

According to Scheme 4, Step 29, a compound of formula XXXIII may be prepared by reaction of a compound of formula XXXII with a catalytic amount of osmium tetroxide or potassium osmate in the presence of a stoichiometric oxidant, such as potassium ferricyanide in the presence of a suitably strong base, such as potassium carbonate in a polar protic solvent, such as a 1:1 mixture of tert-butylalcohol-water. If desired, a catalytic amount of a cinchona alkaloid ligand, may be used to provide enhanced stereoselectivity (ca. 80% de). For example, (DHQD)$_2$PYR ligand (hydroquinidine 2,5-diphenyl-4,6-pyrimidinediyl diether, Aldrich Chemical Corporation) can be used to prepare the 5(R)-hydroxy-Formula I compounds. These so-called "Sharpless Asymmetric Dihydroxylation" techniques are familiar to those skilled in the art (e.g., Kolb, H. C. et al. Chem. Rev. 1994, 2483, incorporated herein by reference).

According to Scheme 4, Step 30, a compound of formula XXXIV may be prepared by treatment of a compound of formula XXXIII with a suitably strong acid, such as hydrochloric acid, in a polar protic solvent, such as water, at a temperature of about 23° C. to about the boiling point of the solvent, preferably about 100° C. for about 4 to about 12 hours.

As shown in Step 31, a compound of formula XXXV may be prepared by treatment of a compound of formula XXXIV with a compound of the Formula:

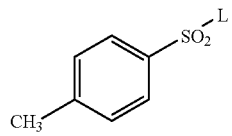

and a base in the presence of a solvent. Group L is a halide selected from chloro and bromo. Suitable bases include a trialkylamine or a pyridine base. Suitable solvents include dichloromethane. The aforesaid reaction is run for a period of time of from about 12 to about 48 hours, preferably about 46 hours, at a temperature of from about 0° C. to 50° C. Compound XXXV is isolated in optically pure form by recrystallization.

According to Step 32, a compound of formula XXXVI may be prepared by reaction of a compound of formula XXXV with hydrogen gas at a pressure between ambient and about 80 psi in a suitable solvent, such as an alcoholic solvent, preferably methanol, in the presence of a palladium catalyst, such as palladium on charcoal or palladium (II) hydroxide on charcoal (so called Pearlman's catalyst), preferably palladium on charcoal at a temperature of about 23° C. to about 50° C., preferably about 23° C. for about 4 to about 24 hours.

In Step 33 of Scheme 4, a compound of formula XXXVII, wherein P$^8$ is a protecting group, preferably a methylenearyl group, most preferably a benzyl group or methyl benzyl group, are preferably prepared by treatment of a compound of formula XXXVI with a benzyloxyaryl halide. Preferably the benzyloxyaryl halide is according to the Formula:

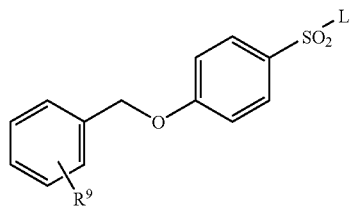

which compounds are commercially available or can be made by methods well known to one of ordinary skill in the art, e.g., PCT publication WO 98/07697, and a base in the presence of a solvent. Group L is a halide selected from chloro and bromo and R$^9$ is H or methyl. Suitable solvents include N,N-dimethylformamide or dichloromethane. The aforesaid reaction is run for a period of time of from about 0.5 to about 20 hours, preferably of from about 1 to about 3 hours, at a temperature of from about 0° C. to 50° C.

As is readily apparent to one of skill in the art, in Step 33, the benzyloxyaryl halide can also be according to the formula:

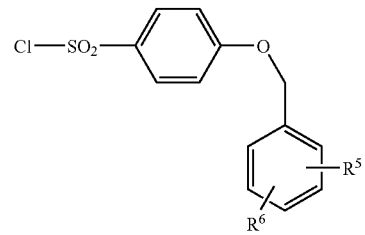

wherein R$^5$ and R$^6$ are as above. As one of skill in the art would recognize, use of this intermediate, wherein the R$^5$ and R$^6$ groups are as desired in the final product, obviates Steps 34 and 25.

According to Step 34, a compound of formula XXXVIII may be prepared by removal of P$^8$ from a compound of formula XXXVII. When P$^8$ is methylene aryl, deprotection is preferably accomplished by treatment of a compound of formula XXXVII with hydrogen gas at a pressure between ambient and about 80 psi in the presence of a catalyst, such as palladium on charcoal, in a polar solvent, preferably methanol or ethanol at a temperature of about 20° C. to about 25° C., preferably about 23° C. for a period of time necessary to effect complete reaction.

As shown in Step 35, a compound of formula XXXIX may be prepared by treatment of a compound of formula XXXVIII with the appropriately substituted benzylhalide according to formula:

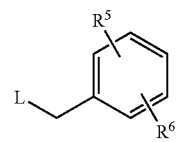

wherein R$^5$ and R$^6$ are as above and L is preferably Cl or Br, in the presence of a suitably strong base, such as a carbonate base, preferably potassium carbonate, in a polar solvent, preferably an aprotic solvent, most preferably dimethylformamide or acetonitrile at a temperature of about 0° C. to about 100° C., preferably about 23° C. to about 50° C.

Finally, a compound of formula XL can be prepared from a compound of formula XXXIX by reaction with a suitably protected hydroxylamine, preferably O-allylhydroxylamine in the presence of a trialkyl aluminum compound, such as trimethylaluminum in a nonpolar aprotic solvent, such as a hydrocarbon solvent, preferably toluene at a temperature between about 50 EC and about the boiling point of the solvent, preferably about 85° C. for about 30 minutes to about 4 hours. A compound of formula XL can be converted into a compound of Formula I—wherein X is carbon; R$^7$, and R$^8$ are hydrogen; R$^1$ and R$^2$ are methyl; one of R$^3$ and $R^4$ is hydroxy (otherwise $R^3$ and $R^4$ are as defined above); and $R^5$ and $R^6$ are as above—via treatment of compound of formula XL according to Step 12 of Scheme 1.

Scheme 5 describes preparation of compounds of Formula I compounds, wherein X is nitrogen, $R^8$ is not present, and $R^7$ is a group of the formula:

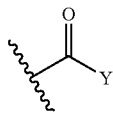

wherein, Y is —NHCH$_3$, and $R^1$, $R^2$, $R^3$, $R^4$, $R^5$, and $R^6$ have the meanings as defined above.

Protected amino acids of formula XLI, wherein $P^9$ is a protecting group—such as, carbonyl methoxy, carbonyl ethoxy, carbonyl t-butoxy, carbonyl benzyloxy, carbonyl trialkylsilyl, more preferably trioxabicyclooctane, most preferably 4-methyl-2,6,7-trioxa-bicyclo[2.2.2]octyl group (commonly referred to as OBO)—are commercially available or can be prepared by known methods, such as the procedures described in: Preparation 2, by Williams in "Synthesis of Optically Active α-Amino Acids", Baldwin, J. E., Ed., Pergamon Press, Oxford, 1989; Coppola and Schuster in "Asymmetric Synthesis. Construction of Chiral Molecules Using Amino Acids", John Wiley & Son; New York, 1987; Corey, E. J., Raju, N., *Tetrahedron Lett.,* 1983, 5571; or Blaskovich, M. A., Lajoie, G. A., *Tetrahedron Lett,* 1993, 3837 and references cited therein, all of which are incorporated herein by reference.

As outlined in Step 37 of Scheme 5, a compound of formula XLII, wherein $R^5$ and $R^6$ are as defined above, may be prepared by reacting a protected amino acid of formula XLI, wherein $P^9$ is a protecting group, preferably carbonyl methoxy, carbonyl ethoxy, carbonyl t-butoxy, carbonyl benzyloxy, carbonyl trialkylsilyl, more preferably trioxabicyclooctane, most preferably 4-methyl-2,6,7-trioxa-bicyclo [2.2.2]octyl group (commonly referred to as OBO), with a sulfonyl chloride of the Formula:

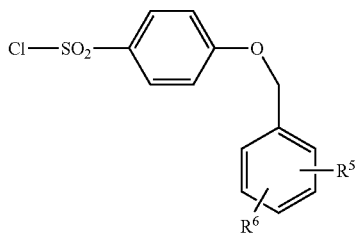

wherein $R^5$ and $R^6$ are as above, in the presence of a base and an inert solvent. Suitable solvents include methylene chloride, tetrahydrofuran, N,N-dimethylformamide, a 1,4-dioxane and water mixture, or an ethyl acetate and water mixture. Suitable bases include triethylamine, diisopropylethylamine, or an alkali earth carbonate or hydroxide. Methylene chloride is the preferred solvent and diisopropylethylamine is the preferred base. The reaction is stirred at a temperature between about 0° C. to about 25° C., preferably at about 0° C., for a time period between about 10 minutes to about 1 day, preferably about 12 hours.

According to Step 38 of Scheme 5, a compound of formula XLIII containing an aziridine ring is prepared from a compound of formula XLII by hydroxyl group activation, followed by intramolecular cyclization. Preferably, this activation is achieved by the conversion of the alcohol to the corresponding sulfonate ester (methyl sulfonate commonly known as mesyl is preferred), or by a complex generated by mixing a trialkylphosphine and a dialkyl azodicarboxylate (preferably triphenylphosphine and diethyl azodicarboxylate are preferred) in a suitable solvent such as tetrahydrofuran. In the former sulfonate case, the aziridine ring is preferably formed by subsequent treatment with a base such as diisopropylethylamine or potassium tert-butoxide. In the latter case, the preferred sequence involves the addition of a compound of formula XLII to a pre-formed complex of the trialkylphosphine and a dialkyl azodicarboxylate. The reaction is stirred at a temperature between about 0° C. to about 25° C., preferably at about 0° C. for a period of time between about 10 minutes to about 4 hours, followed by a period of about 16 hours at about 23° C.

Step 39 refers to the preparation of a compound of formula XLIV by reaction of a compound of formula XLIII with a compound of formula:

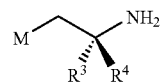

wherein M is halo or hydroxy and $R^3$ and $R^4$ have the meanings as defined above. Preferably, the reaction is run in a suitable solvent such as chloroform, methylene chloride, tetrahydrofuran, methanol, or benzene (methanol is preferred). In some instances a Lewis acid may be included, e.g., zinc chloride, magnesium chloride, or borontrifluoride etherate (borontrifluoride etherate is preferred). The reaction is stirred at a temperature between about 0° C. to about the solvent's boiling point, preferably in methanol at about 60° C., for a time period between about 1 hour to about 4 days, preferably about 2 days.

As outlined in Step 40 of Scheme 5, a compound of formula XLV, is prepared from a compound of formula XLIV by intramolecular ring cyclization methods specific to the nature of the M group. That is, in cases where M is chloro or bromo, the ring can form spontaneously or upon treatment with a suitable base such as diisopropylethylamine or an alkali earth carbonate. Preferably this ring closure is conducted in a solvent such as tetrahydrofuran, benzene, chloroform, or N,N-dimethylformamide (tetrahydrofuran is preferred). The reaction is preferably stirred at a temperature of about 20° C. to about 25° C., preferably about 23° C. to about the solvent's boiling point for a period of time of from about 30 minutes to about 24 hours (about 12 hours is preferred). In cases where M is hydroxy, the hydroxyl group is preferably activated by a complex generated by mixing a trialkylphosphine and a dialkyl azodicarboxylate (triphenylphosphine and dimethyl azodicarboxylate are preferred) in a suitable solvent such as tetrahydrofuran. The preferred sequence involves the addition of XLIV to a the pre-formed complex of the trialkylphosphine and a dialkyl azodicarboxylate. The reaction is stirred at a temperature between about 0° C. to about 25° C., preferably at about 0° C. for a period of time between about 10 minutes to about 4 hours, followed by a period of about 16 hours at about 23° C.

According to Step 41 of Scheme 5, a compound of formula XLVI, wherein the piperazine ring is 4-substituted is prepared by reaction of a compound of formula XLV with the appropriate isocyanate or carbamoyl chloride.

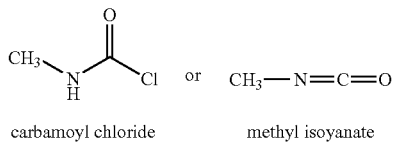

carbamoyl chloride    methyl isoyanate

For compounds of Formula I, wherein Y is NH—CH$_3$, the preferred acylating agent reagent, for reaction with XLV, is methyl isocyanate, but the appropriate carbamoyl chlorides can also be used as acylating agents. When methyl isocyanate is the acylating agent, the methyl isocyanate is added to a cooled dichloromethane solution of XLV, then allowed to stir at a temperature of about 20° C. to about 25° C., preferably about 23° C., followed by work up.

On the other hand, when the acylating agent is a carbamoyl chloride, preferably methyl carbamoyl chloride, a compound of formula XLVI is prepared by standard addition of the appropriate carbamoyl chloride to a solution of a compound of formula XLV in chloroform or methylene chloride, at about 20 to about 25° C., preferably about 23° C., followed by a period of stirring (generally about 1 to about 2 hours).

According to Step 42 of Scheme 5, a compound of formula XLVII can be prepared from a compound of formula XLVI by removal of the protective group P$^9$ to form the carboxylic acid. In the case where the protecting group P$^9$ is carbonyl t-butoxy, this conversion is accomplished with a suitably strong acid such as hydrochloric acid or trifluoroacetic acid (trifluoroacetic acid is preferred). Preferably this reaction is conducted in a solvent such as ethyl acetate, 1,4-dioxane, or methylene chloride (methylene chloride is preferred). In cases where the protecting group P$^9$ is carbonyl methoxy or carbonyl ethoxy, conversion is achieved by saponification with a suitable source of hydroxide such as sodium or lithium hydroxide (lithium hydroxide is preferred). Preferably the saponification is conducted with stirring, in an aqueous solvent mixture such as tetrahydrofuran-methanol-water or 1,4-dioxane-methanol-water at a temperature between about 0° C. to near the boiling point of the solvent system (about 60° C. is preferred). In cases where the protecting group P$^9$ is carbonyl trialkylsilyl, the silyl group can be removed by treatment with dilute aqueous acid such as dilute hydrochloric acid, in aqueous methanol or by heating in methanol at reflux. In cases where the protecting group P$^9$ is carbonyl benzyloxy, conversion is achieved by hydrogenolysis of the benzyl group. The hydrogenolysis is carried out in a suitable solvent such as ethanol, methanol, or ethyl acetate under an atmosphere of hydrogen, in the presence of a catalyst such a 10% palladium on carbon. In cases where the protecting group P$^9$ is a trioxabicyclooctane, conversion is achieved by the action of a suitable acid such as trifluoroacetic acid or hydrochloric acid in aqueous dichloromethane or dichloroethane at a temperature of from between about 0° C. to about the boiling point of the solvent (trifluoroacetic acid in dichloromethane at about 23° C. is preferred) for a period of between about 30 minutes and about 8 hours (less than 1 hour is preferred). This reaction is followed by treatment with an appropriate base such as sodium or lithium hydroxide or cesium carbonate in aqueous mixtures of tetrahydrofuran or an alcoholic solvent such as methanol with stirring at a temperature of about 0° C. to about the boiling point of the solvent (cesium carbonate in methanol-water at about 40° C. to about 60° C. is preferred). Generally, reactions involving the removal of protecting group P$^9$ are run for periods of time between about 30 minutes to about 8 hours, preferably about 4 hours. Unless otherwise mentioned, the aforesaid reactions are performed at a temperature of from about 0° C. to about 25° C., preferably about 23° C.

Finally, in Step 43 of Scheme 5, The 4-substituted piperazine carboxylic hydroxamides of Formula I, wherein Y is NH—CH$_3$, are prepared from a compound of formula XLVII by activation of the carboxylic acid moiety followed by treatment with a hydroxylamine or a protected hydroxylamine that is then deprotected to form the hydroxamic acid. Activation of XLVII carboxyl group is achieved through the action of a suitable activating agent such as dialkyl carbodiimides, benzotriazol-1-yloxy-tris(dialkylamino)-phosphonium salts, or oxalyl chloride in the presence of a catalytic amount of N,N-dimethylformamide. Preferably the activating agent is benzotriazol-1-yloxy-tris(dimethylamino)phosphonium hexafluorophosphate. Generally, the hydroxylamine or protected hydroxylamine is generated in situ from the corresponding salt, such as hydroxylamine hydrochloride, in the presence of an amine base such as triethylamine, or diisopropylethylamine. Suitable protected hydroxylamines include O-tert-butylhydroxylamine, O-allylhydroxylamine, O-tert-butyldimethylsilylhydroxylamine, O-trimethylsilylethylhydroxylamine, O-benzylhydroxylamine, or N,O-bis trimethylsilylhydroxylamine. Where O-benzylhydroxylamine is used, the deprotection is accomplished by hydrogenolysis (5% palladium on barium sulfate is the preferred catalyst). On the other hand, where O-tert-butylhydroxylamine or O-trimethylsilylethylhydroxylamine is used deprotection is achieved by treatment with a strong acid such as trifluoroacetic acid. And when O-allylhydroxylamine is employed, the allyl group is removed either by treatment with ammonium formate in the presence of a catalytic amount of tetrakis(triphenylphosphine)palladium (0) in aqueous acetonitrile at about 60° C. or by treatment with piperidine in the presence of a catalytic amount of allylpalladium chloride dimer and diphenylphosphinoethane in tetrahydrofuran at about 23° C. In the case where N,O-bis-trimethylsilylhydroxylamine is used (preferably generated in situ from trimethylsilylchloride and hydroxylamine hydrochloride in pyridine at about 0° C.), the silyl protective groups are removed by treatment with dilute aqueous acid such as 1 N hydrochloric acid. Suitable solvents for the aforesaid activation and hydroxylamine reaction include methylene chloride, N,N-dimethylformamide, or tetrahydrofuran, preferably methylene chloride. The aforesaid activation and hydroxylamine reactions are run at temperatures between about 0° C. to about 60° C. (about 23° C. is preferred) for periods of time between about 1 hour and about 20 hours (about 4 hours is preferred).

If desired, general intermediate of the formula XLVIII may be prepared.

XLVIII

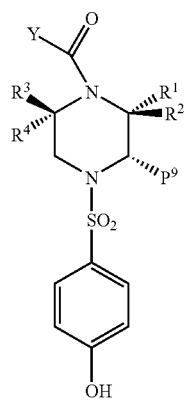

A compound of formula XLVIII may be prepared by treatment of a compound of formula XLVI with hydrogen gas at a pressure between ambient and about 80 psi in the presence of a catalyst, such as palladium on charcoal, in a polar solvent, preferably methanol or ethanol at a temperature of about 20 to about 25° C., preferably about 23° C. for a period of time necessary to effect conversion. The compound of formula XLVIII can be converted to compounds of formula I according to the methods of Steps 42 and 43.

Scheme 6 describes preparation of compounds of Formula I compounds wherein X is nitrogen, $R^8$ is not present, and $R^7$ is a group of the formula:

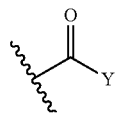

wherein, Y is $CH_2$—$NH_2$ and $R^1$, $R^2$, $R^3$, $R^4$, $R^5$, and $R^6$ have the meanings as defined above.

Referring to Scheme 6, in Step 45, a compound of formula XLIX may be prepared by standard coupling of a protected amino acid, wherein $P^{10}$ represents the protecting group—preferably a butyloxycarbonyl protected aminoacid, wherein $P^{10}$ is preferably butyloxycarbonyl—with a compound of formula XLV (as prepared in Scheme 5). The reaction is accomplished by addition of 1-hydroxybenzotriazole hydrate; an amine, preferably diisopropylamine; a carbodiimide coupling agent, such as dicyclohexylcarbodiimide, preferably 1-(3-dimethylaminopropyl)-3-ethylcarbodiimide hydrochloride; and the appropriate N-protected aminoacid, preferably N-t-butoxycarbonylglycine, to a solution of a compound of formula XLV in chloroform or methylene chloride, at about 20° C. to about 25° C., preferably about 23° C., followed by a period of stirring (generally about 1 to about 2 hours). A compound of formula XLIX may then be converted to a compound of formula L according to Steps 46 and 47. The procedures of Steps 46 and 47 correspond to the procedures of Steps 42 and 43, of Scheme 5, described above.

According to Step 48, a compound of formula L may be deprotected to the corresponding Formula I compound. When the protection group, $P^{10}$, is butyloxycarbonyl, deprotection may be accomplished by treatment with a dichloromethane solution of trifluoroacetic acid to afford the trifluoroacetic acid salt. In the final step the trifluoroacetic acid salt can be converted to the Formula I compound by standard neutralization procedures, such as treatment with aqueous sodium bicarbonate.

Scheme 7 refers to the preparation of a compound of the formula LIV that can be converted to a compound of Formula I, wherein X is nitrogen; $R^8$ is not present; $R^7$ is hydrogen; $R^3$ and $R^4$ are taken together to form a carbonyl group; and $R^1$, $R^2$, $R^5$, and $R^6$ have the meanings as defined above according to Steps 42 and 43 of Scheme 5.

Referring to Scheme 7, a compound of the formula XLIII may be prepared according to the methodology disclosed in Scheme 5. As shown in Step 49, a compound of formula Li may be prepared from a compound of formula XLIII (as prepared in Scheme 5) by treatment with ammonia or an alkyl amine. The protecting group, $P^9$ (as defined in Scheme 5), is selected such that attack on the aziridine occurs preferentially on the $R_1,R_2$-bearing carbon atom. Preferably, $P^9$ is an ortho ester protecting group, such as a 4-methyl-2,6,7-trioxa-bicyclo[2.2.2]octyl group (commonly referred to as OBO). According to Step 49, XLIII is treated with the appropriate alkylamine or ammonia in the presence of a polar solvent, such as an alcoholic solvent, preferably methanol, in a sealed vessel at a temperature between about 0° C. and about 80° C., preferably about 50° C. for a period of about 1 to about 24 hours, preferably about 15 hours.

As shown in Step 50, a compound of formula LII may be prepared from a compound of formula LI by treatment with an appropriate acylating agent, such as benzylchloroformate, in a polar solvent, such as a mixture of dioxane and water, preferably a 2:1 mixture of 1,4-dioxane and water, in the presence of a suitable base, such as an amine or hydroxide base, preferably triethylamine, at a temperature between about the freezing point of the solvent and about 40° C., preferably about 0° C. for about 1 to about 12 hours, preferably about 3 hours.

According to Step 51, a compound of formula LIII may be prepared from a compound of formula LII by treatment with the appropriate alkylating agent, such as an α-haloaceticacid ester, preferably methyl bromoacetate in a polar aprotic solvent, such as dimethylformamide, in the presence of a suitable base, such as a carbonate base, preferably cesium carbonate, at a temperature between about 20° C. and about 50° C., preferably about 23° C.

Finally in Scheme 7, Step 52, a compound of formula LIV is prepared by treatment of a compound of formula LIII with a catalytic amount of a palladium catalyst, preferably 10% palladium on charcoal, in the presence of a stoichiometric amount of a tertiary amine base, such as triethylamine, in a polar solvent, such as an alcoholic solvent, preferably ethanol, under positive pressure of hydrogen gas, preferably atmospheric pressure, for about 0.5 to about 6 hours, preferably about 2 hours at a temperature of about 20° C. to about 25° C., preferably about 23° C. After isolation by filtration and concentration of the filtrate, the material is dissolved in a polar solvent mixture, preferably a mixture of toluene and methanol, and stirred at about 50° C. to about the boiling point of the solvent, preferably at reflux (about 120° C.) for about 1 to about 6 hours, more preferably about 1.5 hours then concentrated to afford the product.

A compound of formula LIV can be converted into a compound Formula I, wherein X is nitrogen; $R^8$ is not present; $R^7$ is hydrogen; $R^3$ and $R^4$ are taken together to form a carbonyl group; and $R^1$, $R^2$, $R^5$, and $R^6$ have the meanings as defined above by treating LIV under the conditions of Steps 42 and 43 of Scheme 5.

Preparation of acid and base addition salts is well known in the art. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The invention also relates to base addition salts of formula I. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

The ability of the compounds of formula I or their therapeutically acceptable salts to inhibit aggrecanase, collagenase-1, collagenase-3, and TACE and, consequently, demonstrate their effectiveness for treating diseases involving these enzymes is shown by the following in vitro assay tests. The $IC_{50}$s for aggrecanase proteolytic activity were determined with an aggrecanase chondrocyte assay; the collagenase-1 $IC_{50}$s were measured with a recombinant collagenase-1 assay; the collagenase-3 $IC_{50}$s were determined with a recombinant collagenase-3 assay; and the TACE $IC_{50}$s were determined with a TACE whole blood assay. Note that the TACE whole blood assay, in general, gives values about 1000 fold greater than the recombinant collagenase assays. Thus, a compound with a TACE $IC_{50}$ of 1000 nM (i.e., 1 µM) is approximately equipotent to a collagenase $IC_{50}$ of 1 nM. These assays are defined below in the Biological Assay Section.

Biological Assays Used in The Invention

Inhibition of Human Collagenase-1 (Recombinant Collagenase-1 Assay)

This assay is used in the invention to measure the potency ($IC_{50}$s) of compounds for collagenase-1.

Human recombinant collagenase-1 is activated with trypsin. The amount of trypsin is optimized for each lot of collagenase-1, but a typical reaction uses the following ratio: 5 mg trypsin per 100 mg of collagenase. The trypsin and collagenase are incubated at about 20° C. to about 25° C., preferably about 23° C. for about 10 minutes then a five fold excess (50 mg/10 mg trypsin) of soybean trypsin inhibitor is added.

Stock solutions (10 mM) of inhibitors are made up in dimethylsulfoxide and then diluted using the following scheme:

10 mM------>120 µM------>12 µM------>1.2 µM------>0.12 µM

Twenty-five microliters of each concentration is then added in triplicate to appropriate wells of a 96 well microfluor plate. The final concentration of inhibitor will be a 1:4 dilution after addition of enzyme and substrate. Positive controls (enzyme, no inhibitor) are set up in wells D7–D12 and negative controls (no enzyme, no inhibitors) are set in wells D1–D6.

Collagenase-1 is diluted to 240 ng/ml and 25 ml is then added to appropriate wells of the microfluor plate. Final concentration of collagenase in the assay is 60 ng/ml.

Substrate (DNP-Pro-Cha-Gly-Cys(Me)-His-Ala-Lys (NMA)-$NH_2$) is made as a 5 mM stock in dimethylsulfoxide and then diluted to 20 µM in assay buffer. The assay is initiated by the addition of 501 µl substrate per well of the microfluor plate to give a final concentration of 10 µM.

Fluorescence readings (360 nM excitation, 460 nm emission) are taken at time 0 and then at about 20 minute intervals. The assay is conducted at a temperature of about 20 to about 25° C., preferably about 23° C. with a typical assay time of about 3 hours.

Fluorescence versus time is then plotted for both the blank and collagenase containing samples (data from triplicate determinations is averaged). A time point that provides a good signal (at least five fold over the blank) and that is on a linear part of the curve (usually around 120 minutes) is chosen to determine $IC_{50}$ values. The zero time is used as a blank for each compound at each concentration and these values are subtracted from the 120 minute data. Data is plotted as inhibitor concentration versus % control (inhibitor fluorescence divided by fluorescence of collagenase alone ×100). $IC_{50}$s are determined from the concentration of inhibitor that gives a signal that is 50% of the control.

If $IC_{50}$s are reported to be less than 0.03 mM, then the inhibitors are assayed at concentrations of 0.3 µM, 0.03 µM, and 0.003 µM.

Using this assay, the following data was obtained for the hydroxamic derivative below.

| Compound | Collagenase-1 $IC_{50}$ | Standard deviation |
|---|---|---|
| (structure shown) | 3 nM | 2.00 |

Inhibition of Human Collagenase-3 (Recombinant Collagenase-3 Assay)

This assay is used in the invention to measure the potency ($IC_{50}$s) of compounds for collagenase-3.

Human recombinant collagenase-3 is activated with 2 mM APMA (p-aminophenyl mercuric acetate) for about 2.0 hours, at about 37° C. and is diluted to about 240 ng/ml in assay buffer (50 mM Tris, pH 7.5, 200 mM sodium chloride, 5 mM calcium chloride, 20 mM zinc chloride, 0.02% BRIJ-35). Twenty-five micro-liters of diluted enzyme is added per well of a 96 well microfluor plate. The enzyme is then diluted in a 1:4 ratio by inhibitor addition and substrate to give a final concentration in the assay of 60 ng/ml.

Stock solutions (10 mM) of inhibitors are made up in dimethylsulfoxide and then diluted in assay buffer as per the inhibitor dilution scheme for inhibition of human collagenase-1: Twenty-five microliters of each concentration is added in triplicate to the microfluor plate.

The final concentrations in the assay are 30 µM, 3 µM, 0.3 µM, and 0.03 µM.

Substrate (Dnp-Pro-Cha-Gly-Cys(Me)-His-Ala-Lys (NMA)-$NH_2$) is prepared as for inhibition of human collagenase (collagenase-1) and 50 ml is added to each well to give a final assay concentration of 10 µM. Fluorescence readings (360 nm excitation; 450 nm emission) are taken at time 0 and about every 5 minutes for about 1 hour.

Positive controls and negative controls are set up in triplicate as outlined in the collagenase-1 assay. $IC_{50}$'s are determined as per inhibition of human collagenase (collagenase-1). If $IC_{50}$'s are reported to be less than 0.03 mM, inhibitors are then assayed at final concentrations of 0.3 µM, 0.03 µM, 0.003 µM and 0.0003 µM.

All of the compounds that were tested had IC$_{50}$ of less than 30 nM. Preferred compounds of the invention had IC$_{50}$ of less than about 10 nM.

Using this assay, the following data was obtained for the hydroxamic derivative below.

| Compound | Collagenase-3 IC$_{50}$ | Standard deviation |
|---|---|---|
| [structure with CH$_3$O-phenyl, hydroxamic acid, isobutyl, NH-CH$_3$ amide] | 1 nM | 0.68 |

Aggrecanase Chondrocyte Assay

This assay is used in the invention to measure the potency (IC$_{50}$s) of compounds for aggrecanase.

Primary porcine chondrocytes from articular joint cartilage are isolated by sequential trypsin and collagenase digestion followed by collagenase digestion overnight and are plated at 2×10$^5$ cells per well into 48 well plates with 5 µCi/ml $^{35}$S (1000 Ci/mmol) sulphur in type I collagen coated plates. Cells are allowed to incorporate label into their proteoglycan matrix (approximately 1 week) at 37° C., under an atmosphere of 5% CO$_2$.

The night before initiating the assay, chondrocyte monolayers are washed two times in DMEM/1% PSF/G and then allowed to incubate in fresh DMEM/1% FBS overnight.

The following morning chondrocytes are washed once in DMEM/1% PSF/G. The final wash is allowed to sit on the plates in the incubator while making dilutions. Media and dilutions can be made as described in the Table I below.

TABLE 1

| Control Media | DMEM alone (control media) |
|---|---|
| IL-1 Media | DMEM + IL-1 (5 ng/ml) |
| Drug Dilutions | Make all compounds stocks at 10 mM in DMSO. Make a 100 µM stock of each compound in DMEM in 96 well plate. Store in freezer overnight. The next day perform serial dilutions in DMEM with IL-1 to 5 µM, 500 nM, and 50 nM. Aspirate final wash from wells and add 50 µl of compound from above dilutions to 450 µl of IL-1 media in appropriate wells of the 48 well plates. Final compound concentrations equal 500 nM, 50 nM, and 5 nM. All samples completed in triplicate with Control and IL-1 alone samples on each plate. |

Plates are labeled and only the interior 24 wells of the plate are used. On one of the plates, several columns are designated as IL-1 (no drug) and Control (no IL-1, no drug). These control columns are periodically counted to monitor 35S-proteoglycan release. Control and IL-1 media are added to wells (450 µl) followed by compound (50 µl) so as to initiate the assay. Plates are incubated at 37° C., with a 5% CO$_2$ atmosphere.

At 40–50% release (when CPM from IL-1 media is 4–5 times control media) as assessed by liquid scintillation counting (LSC) of media samples, the assay is terminated (about 9 to about 12 hours). Media is removed from all wells and placed in scintillation tubes. Scintillate is added and radioactive counts are acquired (LSC). To solubilize cell layers, 500 µL of papain digestion buffer (0.2 M Tris, pH 7.0, 5 mM EDTA, 5 mM DTT, and 1 mg/ml papain) is added to each well. Plates with digestion solution are incubated at 60° C. overnight. The cell layer is removed from the plates the next day and placed in scintillation tubes. Scintillate is then added, and samples counted (LSC).

The percent of released counts from the total present in each well is determined. Averages of the triplicates are made with control background subtracted from each well. The percent of compound inhibition is based on IL-1 samples as 0% inhibition (100% of total counts).

Using this assay, the following data was obtained for the hydroxamic derivative below.

| Compound | Aggrecanase IC$_{50}$ | Standard deviation |
|---|---|---|
| [structure with phenethyl, cyclohexylmethyl, sulfonamide-phenyl, hydroxamic acid] | 53.5 nM | 0.61 |

Inhibition of Soluble TNF-α Production (TACE Whole Blood Assay)

This assay is used in the invention to measure the potency ($IC_{50}$s) of compounds for TACE.

The ability of the compounds or the therapeutically acceptable salts thereof to inhibit the cellular release of TNF-α and, consequently, demonstrate their effectiveness for treating diseases involving the disregulation of soluble TNF-α is shown by the following in vitro assay:

Human mononuclear cells are isolated from anti-coagulated human blood using a one-step Ficoll-hypaque separation technique. (2) The mononuclear cells are washed three times in Hanks balanced salt solution (HBSS) with divalent cations and re-suspended to a density of $2 \times 10^6$/ml in HBSS containing 1% BSA. Differential counts are determined using the Abbott Cell Dyn 3500 analyzer indicated that monocytes ranged from 17 to 24% of the total cells in these preparations.

180 μL of the cell suspension was aliquoted into flat bottom 96 well plates (Costar). Additions of compounds and LPS (100 ng/ml final concentration) gives a final volume of 200 μL. All conditions are performed in triplicate. After about a four hour incubation at about 37° C. in an humidified $CO_2$ incubator, plates are removed and centrifuged (about 10 minutes at approximately 250×g) and the supernatants removed and assayed for TNF-α using the R&D ELISA Kit.

Using this assay, the following data was obtained for the hydroxamic derivative below.

| Compound | TACE $IC_{50}$ | Standard deviation |
|---|---|---|
| (structure shown) | 3 μM | 10 |

Table 2 below lists some examples of the compounds identified and synthesized according to the above-described assays and synthetic methodology.

TABLE 2

| Structure | Name | Agg | MMP-13 | MMP-1 | TACE |
|---|---|---|---|---|---|
| (structure) | (2R,3R) 1-[4-(2,4-dichloro-benzyloxy)-benzenesulfonyl]-3-hydroxy-3-methyl-piperidine-2-carboxylic acid hydroxyamide | ++ | ++ | − | + |
| (structure) | (2R,5R) 1-[4-(2,4-dichloro-benzyloxy)-benzenesulfonyl]-5-hydroxy-3,3-dimethyl-piperidine-2-carboxylic acid hydroxyamide | ++ | ++ | − | m |
| (structure) | (2R,3S) 1-[4-(2-methyl-benzyloxy)-benzenesulfonyl]-4-aminoacetyl-3-methyl-piperazine-2-carboxylic acid hydroxyamide | ++ | m | −− | ++ |

TABLE 2-continued

| Structure | Name | Agg | MMP-13 | MMP-1 | TACE |
|---|---|---|---|---|---|
| 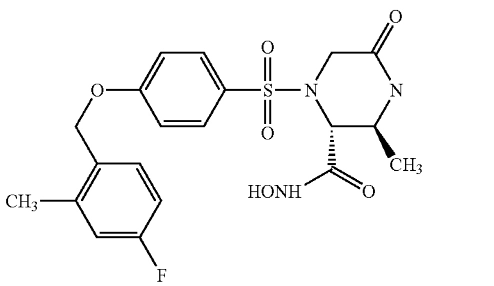 | (2R,3S) 1-[4-(4-fluoro-2-methyl-benzyloxy)-benzenesulfonyl]-3-methyl-5-oxo-piperazine-2-carboxylic acid hydroxyamide | ++ | + | -- | ++ |
| 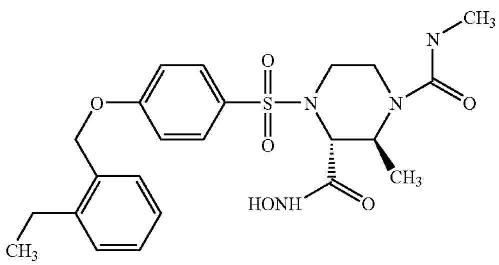 | (2R,3S) 4-[4-(2-ethyl-benzyloxy)-benzenesulfonyl]-3-methyl-4-carboxylic acid methylamide-piperazine-2-carboxylic acid hydroxyamide | ++ | m | -- | ++ |
| 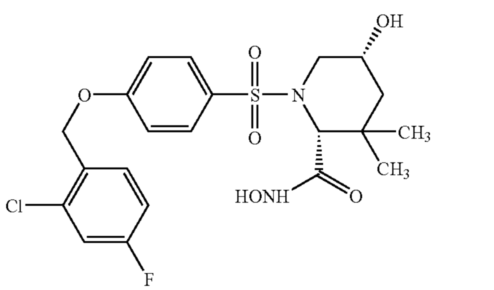 | (2R,5R) 1-[4-(2-chloro-4-fluoro-benzyloxy)-benzenesulfonyl]-5-hydroxy-3,3-dimethyl-piperidine-2-carboxylic acid hydroxyamide | ++ | ++ | - | + |
| 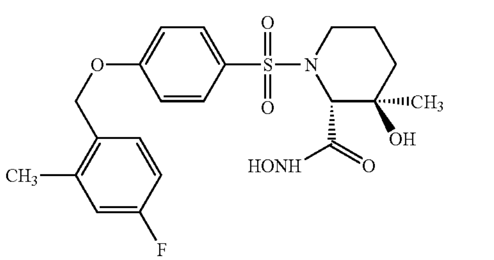 | (2R,3R) 1-[4-(4-fluoro-2-methyl-benzyloxy)-benzenesulfonyl]-3-hydroxy-3-methyl-piperidine-2-carboxylic acid hydroxyamide | ++ | ++ | - | ++ |
| 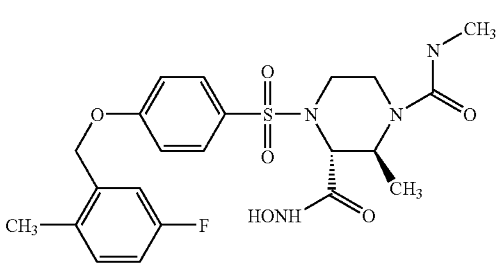 | (2R,3S) 4-[4-(5-fluoro-2-methyl-benzyloxy)-benzenesulfonyl]-3-methyl-4-carboxylic acid methylamide-piperazine-2-carboxylic acid hydroxyamide | ++ | ++ | -- | ++ |

TABLE 2-continued

| Structure | Name | Agg | MMP-13 | MMP-1 | TACE |
|---|---|---|---|---|---|
| 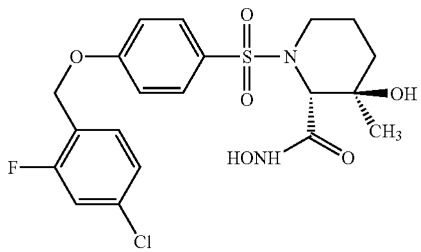 | (2R,3R) 1-[4-(2-fluoro-4-chloro-benzyloxy)-benzenesulfonyl]-3-hydroxy-3-methyl-piperidine-2-carboxylic acid hydroxyamide | ++ | ++ | m | − |
| 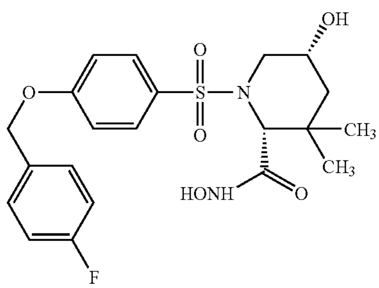 | (2R,5R) 1-[4-(4-fluoro-benzyloxy)-benzenesulfonyl]-5-hydroxy-3,3-dimethyl-piperidine-2-carboxylic acid hydroxyamide | ++ | ++ | m | + |
| 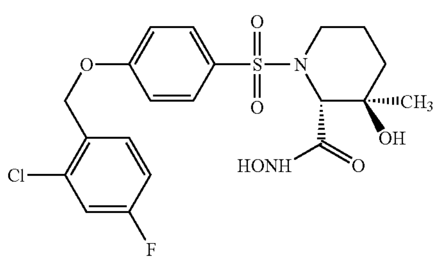 | (2R,3R) 1-[4-(2-chloro-4-fluoro-benzyloxy)-benzenesulfonyl]-3-hydroxy-3-methyl-piperidine-2-carboxylic acid hydroxyamide | ++ | ++ | − | + |
| 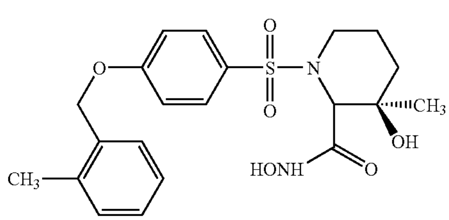 | (2R,3R) 1-[4-(2-methyl-benzyloxy)-benzenesulfonyl]-3-hydroxy-3-methyl-piperidine-2-carboxylic acid hydroxyamide | ++ | ++ | − | ++ |
| 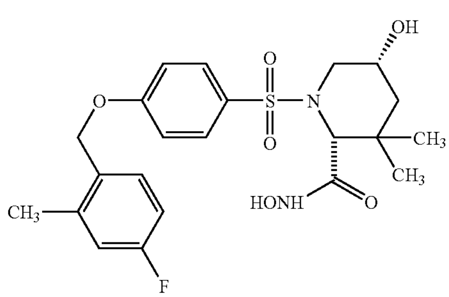 | (2R,5R) 1-[4-(4-fluoro-2-methyl-benzyloxy)-benzenesulfonyl]-5-hydroxy-3,3-dimethyl-piperidine-2-carboxylic acid hydroxyamide | ++ | ++ | − | ++ |

TABLE 2-continued

| Structure | Name | Agg | MMP-13 | MMP-1 | TACE |
|---|---|---|---|---|---|
| 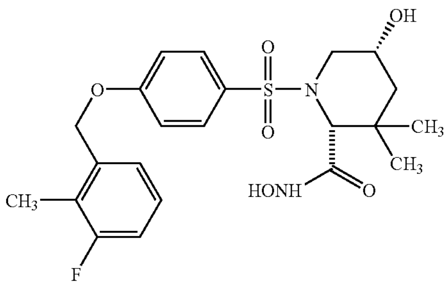 | (2R,5R) 1-[4-(2-methyl-3-fluoro-benzyloxy)-benzenesulfonyl]-5-hydroxy-3,3-dimethyl-piperidine-2-carboxylic acid hydroxyamide | ++ | ++ | − | ++ |
| 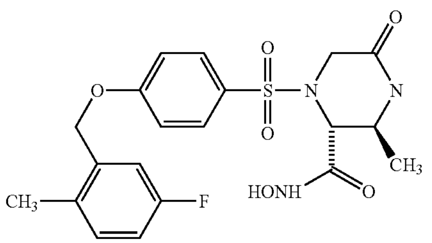 | (2R,3S) 1-[4-(2-methyl-5-fluoro-benzyloxy)-benzenesulfonyl]-3-methyl-5-oxo-piperazine-2-carboxylic acid hydroxyamide | ++ | + | −− | ++ |
| 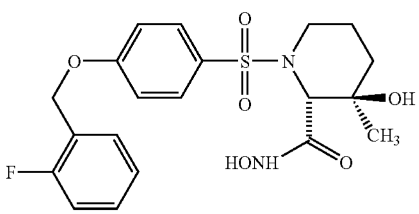 | (2R,3R) 1-[4-(2-fluoro-benzyloxy)-benzenesulfonyl]-3-hydroxy-3-methyl-piperidine-2-carboxylic acid hydroxyamide | + | ++ | m | m |
| 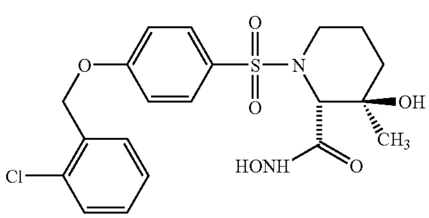 | (2R,3R) 1-[4-(2-chloro-benzyloxy)-benzenesulfonyl]-3-hydroxy-3-methyl-piperidine-2-carboxylic acid hydroxyamide | ++ | ++ | − | ++ |
| 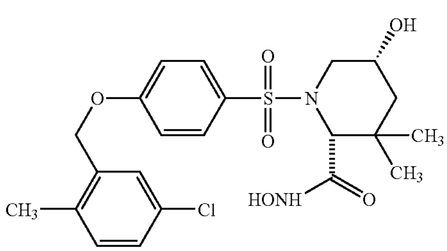 | (2R,5R) 1-[4-(2-methyl-5-chloro-benzyloxy)-benzenesulfonyl]-5-hydroxy-3,3-dimethyl-piperidine-2-carboxylic acid hydroxyamide | + | m | −− | + |
| 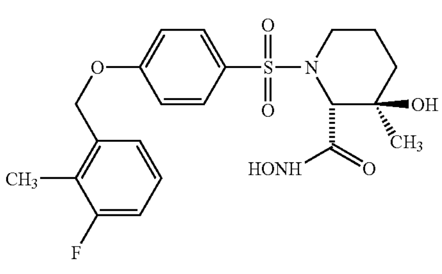 | (2R,3R) 1-[4-(2-methyl-3-fluorobenzyloxy)-benzenesulfonyl]-3-hydroxy-3-methyl-piperidine-2-carboxylic acid hydroxyamide | + | ++ | −− | ++ |

TABLE 2-continued

| Structure | Name | Agg | MMP-13 | MMP-1 | TACE |
|---|---|---|---|---|---|
| 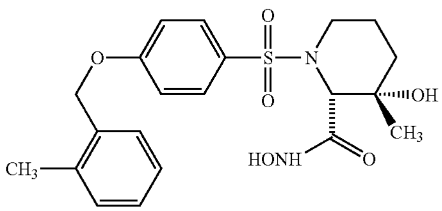 | (2R,3S) 1-[4-(2-methyl-benzyloxy)-benzenesulfonyl]-3-hydroxy-3-methyl-piperidine-2-carboxylic acid hydroxyamide | + | ++ | − | ++ |
| 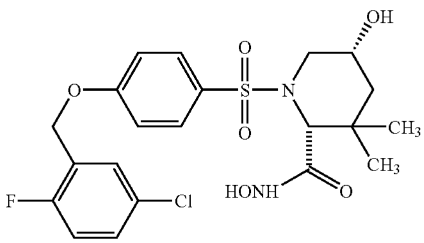 | (2R,5R) 1-[4-(2-fluoro-5-chloro-benzyloxy)-benzenesulfonyl]-5-hydroxy-3,3-dimethyl-piperidine-2-carboxylic acid hydroxyamide | + | ++ | − | + |
| 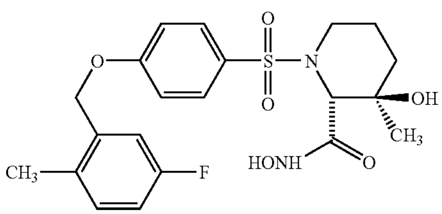 | (2R,3R) 1-[4-(2-methyl-5-fluorobenzyloxy)-benzenesulfonyl]-3-hydroxy-3-methyl-piperidine-2-carboxylic acid hydroxyamide | + | ++ | − | ++ |
| 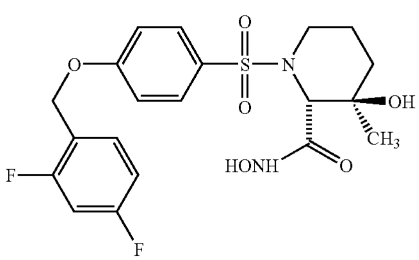 | (2R,3R) 1-[4-(2,4-difluoro-benzyloxy)-benzenesulfonyl]-3-hydroxy-3-methyl-piperidine-2-carboxylic acid hydroxyamide | + | ++ | − | + |
| 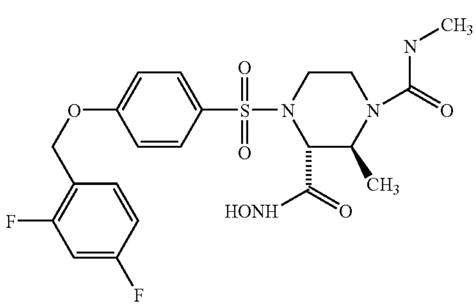 | (2R,3S) 4-[4-(2,4-difluoro-benzyloxy)-benzenesulfonyl]-3-methyl-4-carboxylic acid methylamide-piperazine-2-carboxylic acid hydroxyamide | + | ++ | − | + |
| 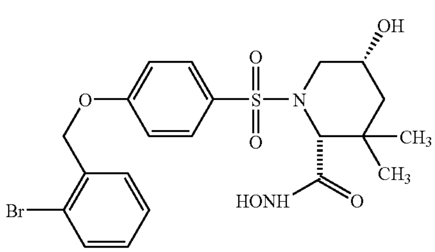 | (2R,5R) 1-[4-(2-bromo-benzyloxy)-benzenesulfonyl]-5-hydroxy-3,3-dimethyl-piperidine-2-carboxylic acid hydroxyamide | + | ++ | − | ++ |

++Indicates that the compound has an $IC_{50}<10$ nM for aggrecanase, MMP-13, or MMP-1, while for TACE, ++corresponds to an $IC_{50}<10$ μM.

+Indicates that the compound has a $IC_{50}$ value within the range of 10 nM<$IC_{50}$<20 nM for aggrecanase, MMP-13, or MMP-1, while for TACE, +Indicates that the compound has a $IC_{50}$ value within the range of 10 μM<$IC_{50}$<20 μM.

m Indicates that the compound has a $IC_{50}$ value within the range of 200 nM>$IC_{50}$>20 nM for aggrecanase, MMP-13, or MMP-1, while for TACE, m Indicates that the compound has a $IC_{50}$ value within the range of 20 μM<$IC_{50}$<40 μM for TACE)

−Indicates that the compound has a $IC_{50}$ value within the range of 1000 nM>$IC_{50}$>200 nM for aggrecanase, MMP-13, or MMP-1, while for TACE,—Indicates that the compound has a $IC_{50}$>40 μM.

−−Indicates that the compound has an $IC_{50}$>1000 nM for aggrecanase, MMP-13, or MMP-1.

Agg is aggrecanase.

One of ordinary skill in the art will appreciate that the compounds of the invention are useful in treating a diverse array of diseases in mammals such as humans, especially diseases characterized by joint inflammation and the destruction of articular cartilage, such as: osteoarthritis, joint injury, reactive arthritis, acute pyrophosphate arthritis, psoriatic arthritis, and rheumatoid arthritis.

For administration to mammals, including humans a variety of conventional routes may be used including oral, parenteral, intravenous, intramuscular, subcutaneous, buccal, anal, and topical. In general, the compounds of the invention (hereinafter also known as the active compounds) will be administered at dosages to achieve maximum inhibition of collagenase-3 and aggrecanase without significant side effects, particularly side effects resulting from systemic inhibition of collagenase-1.

Preferably the active compound will be administered orally or parenterally. Of course, some variation in dosage will necessarily occur depending on the condition of the subject being treated. The person responsible for administration will determine the appropriate dose for the individual subject.

The active compounds can be administered in a wide variety of different dosage forms, in general, the therapeutically effective compounds of this invention are present in such dosage forms at dosage levels between about 0.1 and 25 mg/kg body weight of the subject per day, preferably of from about 0.3 to 5 mg/kg. But some variation in dosage will necessarily occur depending on the condition of the subject to be treated. The person responsible for administration will determine the appropriate dose for the individual subject.

For oral administration, tablets containing various excipients, such as, microcrystalline cellulose, sodium citrate, calcium carbonate, dicalcium phosphate, and glycine may be employed along with various disintegrants, such as, starch (preferably corn, potato, or tapioca starch), alginic acid, and certain complex silicates, together with granulation binders like polyvinylpyrrolidone, sucrose, gelatin, and acacia. Additionally, lubricating agents, such as, magnesium stearate, sodium lauryl sulfate, and talc are often very useful for tableting purposes. Solid compositions of a similar type may also be employed as fillers in gelatin capsules; preferred materials also include lactose or milk sugar as well as high molecular polyethylene glycols. When aqueous suspensions or elixirs are desired for oral administration, the active ingredient may be combined with various sweetening or flavoring agents, coloring matter or dyes, and, if so desired, emulsifying or suspending agents together with diluents, such as, water, ethanol, propylene glycol, glycerin, and various combinations thereof.

For parenteral administration (intramuscular, intraperitoneal, subcutaneous, and intravenous use) a sterile injectable solution of the active ingredient is usually prepared. Solutions of a therapeutic compound of the present invention in either sesame or peanut oil in aqueous propylene glycol may be employed. The aqueous solutions should be suitably adjusted and buffered. These aqueous solutions are suitable for intraarticular, intramuscular, and subcutaneous injection purposes. The preparation of these solutions under sterile conditions is readily accomplished by standard pharmaceutical techniques well known to those skilled in the art. In the case of animals, compounds can be administered intramuscularly or subcutaneously in a singly dose or up to 3 divided doses.

The active compounds may also be formulated in rectal compositions, such as, suppositories or retention enemas, e.g., containing conventional suppository bases, such as, cocoa butter or other glycerides.

For intranasal administration, or administration by inhalation, the active compounds may be administered by a standard dropper. Also, the active compounds can be conveniently delivered in the form of a solution or suspension from a pump spray container that is squeezed or pumped by the patient or as an aerosol spray from a pressurized container or nebulizer, with the use of a suitable propellant, e.g., dichlorodifluoromethane, trichlorofluoromethane, dichlorotetrafluoroethane, carbon dioxide, or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base, such as, lactose or starch.

Although the present invention has been described in considerable detail with reference to certain preferred embodiments, other embodiments are possible. Therefore, the spirit and scope of the appended claims should not be limited to the description of the preferred embodiments contained herein.

EXAMPLES

General Methods to Prepare Compounds Of Formula I

Unless otherwise specified, the starting materials were purchased from Aldrich Chemical Corporation. Isolation and purification was accomplished by well known methods, such as, chromatography, crystallization, and distillation. All products were characterized by conventional methods such $^1$H NMR and mass spectroscopy. The enantiomeric excesses, where determined, were obtained by chiral phase HPLC. All the compounds of Formula I, prepared according to the schemes below, had optical purities of at least 85% enantiomeric excess (ee).

The compounds of the invention may have one or more chiral centers. Therefore, one may selectively prepare the diastereomers or enantiomers. For example, by use of chiral starting materials or catalysts. Also, since the compounds of the invention may exist as mixtures of diastereomers or enantiomers, the individual stereoisomers may be separated and isolated in optically pure form, by well known methods, such as, chiral chromatography (e.g., chiral phase gas or liquid phase chromatography), selective crystallization, or use of chiral salt complexes.

Example 1

Preparation of a Compound of Formula I, Wherein X is Carbon, $R^3$, $R^4$, $R^7$, and $R^8$ are Each Hydrogen, and $R^1$, $R^2$, $R^5$, and $R^6$ are as Above, According to General Scheme 1

Example of a Preparation of a Compound of Formula III, Step 1, Scheme 1 (2-Hydroxy-1-hydroxymethyl-2-methyl-but-3-enyl)-carbamic acid tert-butyl ester To a solution of 4-(1-hydroxy-1-methyl-allyl)-2,2-dimethyl-oxazolidine-3-carboxylic acid tert-butyl ester (compound of formula II, 3.3 g, 12.1 mmol, prepared as in Ageno, G.; Banfi, L.; Cascio, G.; Guanti, G.; Manghisi, E.; Riva, R.; Rocca, V. *Tetrahedron*, 1995, 29, 8121) in 100 ml of methanol was added p-toluenesulfonic acid monohydrate (0.215 g, 1.1 mmol). After stirring for about 30 minutes at a temperature of about 20° C. to about 25° C., the mixture was diluted with saturated aqueous sodium bicarbonate and was concentrated in vacuo. The residue was diluted with water and was extracted 3 times into ethyl acetate. The combined organic layers were dried over sodium sulfate, filtered and concentrated in vacuo to afford 2.8 g of (2-Hydroxy-1-hydroxymethyl-2-methyl-but-3-enyl)-carbamic acid tert-butyl ester (compound of formula III) as a colorless syrup.

Example of a Preparation of a Compound of Formula VI, Steps 2,3, and 4, Scheme 1 4-Benzyloxy-N-[1-(tert-butyl-diphenyl-silanyloxymethyl)-2-hydroxy-2-methyl-but-3-enyl]-benzenesulfonamide To a solution of (2-hydroxy-1-hydroxymethyl-2-methyl-but-3-enyl)-carbamic acid tert-butyl ester (compound of formula III, 3 g, 13 mmol) in 13 ml of anhydrous dimethylformamide was added imidazole (1.63 g, 24 mmol) and tert-butyl diphenylchlorosilane (3.4 ml, 3.6 g, 13 mmol). After stirring at a temperature of about 20° C. to about 25° C. for about 24 hours, the mixture was diluted with ethyl acetate, washed twice with water, twice with brine, dried over sodium sulfate, filtered and concentrated to afford the compound of structure IV.

The residue was dissolved in 20 ml of methylene chloride and was treated with 10 ml of trifluoroacetic acid at about 0° C. After stirring for about 1.5 hours, the mixture was concentrated to afford a compound of formula V.

The compound of formula V was dissolved in 65 ml of methylene chloride and was treated with triethylamine (7.4 ml, 52 mmol) and 4-benzyloxy-benzenesulfonyl chloride (3.7 g, 13 mmol). After stirring for about 24 hours at a temperature of about 20° C. to about 25° C., the mixture was diluted with ethyl acetate, washed twice with 1M hydrochloric acid, twice with saturated aqueous sodium bicarbonate, twice with brine, dried over sodium sulfate and concentrated in vacuo. Purification using a Flash 40 system (silica gel cartridge, eluting with 20% ethyl acetate in hexane) afforded 3.5 g of 4-benzyloxy-N-[1-(tertbutyl-diphenyl-silanyloxymethyl)2-hydroxy-2-methyl-but-3-enyl]-benzenesulfonamide (compound of formula VI) as a colorless syrup.

Example of a Preparation of a Compound of Formula VIII, Step 5, Scheme 1 N-Allyl-4-benzyloxy-N-[1-(tert-butyl-diphenyl-silanyloxymethyl)-2-hydroxy-2-methyl-but-3-enyl]-benzenesulfonamide To a solution of 4-benzyloxy-N-[1-(tert-butyl-diphenyl-silanyloxymethyl)-2-hydroxy-2-methyl-but-3-enyl]-benzenesulfonamide (compound of formula VI, 1.6 g, 2.6 mmol) in 5 ml of dimethylformamide was added cesium carbonate (1.7 g, 5.2 mmol) and allyl bromide (0.63 g, 5.2 mmol). After stirring at a temperature of about 20 to about 25° C. for about 24 hours, an additional 0.4 g of cesium carbonate and 0.2 ml of allyl bromide was added, and the mixture was stirred at a temperature of about 20° C. to about 25° C. for about 24 hours. The mixture was diluted with ethyl acetate, washed 4 times with water, dried over sodium sulfate, filtered and concentrated in vacuo to afford 1.75 g of N-allyl-4-benzyloxy-N-[1-(tert-butyl-diphenyl-silanyloxymethyl)-2-hydroxy-2-methyl-but-3-enyl]-benzenesulfonamide (compound of formula VII) as a colorless syrup.

Example of a Preparation of a Compound of Formula VIII, Step 6, Scheme 1 1-(4-Benzyloxy-benzenesulfonyl)-2-(tert-butyl-diphenyl-silanyloxymethyl)-3-methyl-1,2,3,6-tetrahydro-pyridin-3-ol A mixture of N-allyl-4-benzyloxy-N-[1-(tert-butyl-diphenyl-silanyloxymethyl)-2-hydroxy-2-methyl-but-3-enyl]-benzenesulfonamide (compound of formula VII, 4.0 g, 6.1 mmol), diallyl ether (0.82 ml, 0.66 g, 6.7 mmol), bis (tricyclohexylphosphine)benzylidine ruthenium (IV) dichloride (0.34 g, 0.4 mmol) and methylene chloride (116 ml) was stirred at reflux for about 3 hours. The mixture was concentrated in vacuo then purified using a Flash 40 system (silica gel cartridge, eluting with 10% ethyl acetate in hexane) to afford 2.8 g of 1-(4-benzyloxy-benzenesulfonyl)-2-(tert-butyldiphenyl-silanyloxymethyl)-3-methyl-1,2,3,6-tetrahydro-pyridin-3-ol (compound of formula VIII) as a colorless solid.

Example of a Preparation of a Compound of Formula IX, Step 7, Scheme 1 2-(tert-Butyl-diphenyl-silanyloxymethyl)-1-(4-hydroxy-benzenesulfonyl)-3-methyl-piperidin-3-ol A mixture of 1-(4-benzyloxy-benzenesulfonyl)-2-(tert-butyl-diphenyl-silanyloxymethyl)-3-methyl-1,2,3,6-tetrahydro-pyridin-3-ol (compound of formula VIII, 0.40 g, 0.64 mmol), 10% palladium on charcoal (0.1 g) and 30 ml of methanol was stirred for about 16 hours under about 1 atmosphere of hydrogen gas. The mixture was filtered through a pad of Celite®. Concentration of the filtrate afforded 0.35 g of 2-(tert-butyl-diphenyl-silanyloxymethyl)-1-(4-hydroxy-benzenesulfonyl)-3-methyl-piperidin-3-ol (compound of formula IX) as a colorless solid.

General Procedure for the Preparation of a Compound of Formula XII, Steps 8 and 9, Scheme 1]

A mixture of 2-(tert-butyl-diphenyl-silanyloxymethyl)-1-(4-hydroxy-benzenesulfonyl)-3-methyl-piperidin-3-ol (compound of formula IX, 0.35 g, 0.64 mmol), the appropriate benzyl halide (0.77 mmol), cesium carbonate (0.42 g, 1.28 mmol) and dimethylformamide (1.3 ml) was stirred at a temperature of about 20° C. to about 25° C. for about 24 hours. The mixture was diluted with ethyl acetate, washed with 1M hydrochloric acid, saturated aqueous sodium bicarbonate, dried over sodium sulfate, filtered and concentrated to give a compound of formula X.

The compound of formula X was taken up in 4 ml of tetrahydrofuran and was treated with 1 ml of 1M tetrabutylammonium fluoride in tetrahydrofuran. After stirring for about 6 hours at a temperature of about 20° C. to about 25° C., the mixture was diluted with ethyl acetate, washed twice with water, dried over sodium sulfate, filtered and concentrated in vacuo. Purification of the residue by silica gel chromatography afforded a compound of formula XI as a colorless syrup.

General Procedure for the Preparation of a Compound of Formula XII, Step 10, Scheme 1

A stock solution of periodic acid and chromium trioxide in acetonitrile was prepared as follows: 1.14 g of periodic acid and 5 mg of chromium (VI) oxide was dissolved in 11.4 ml of 0.75% water-acetonitrile. To a solution of a compound of formula XI (0.16 g, 0.38 mmol) in 1.88 ml of acetonitrile was added 2.14 ml of the periodic acid/chromic acid solution at about 0° C. After stirring for about 5 to about 20 minutes, the mixture was diluted with ethyl acetate, washed once with water and twice with brine, dried over sodium sulfate, filtered and concentrated, affording a compound of formula XII as a colorless syrup.

General Procedure for the Preparation of Formula I, Wherein X is Carbon, and $R^3$, $R^4$, $R^7$, and $R^8$ are Each Hydrogen, and $R^1$, $R^2$, $R^5$, and $R^6$ are as Above, Steps 11 and 12, Scheme 1

To a solution of a carboxylic acid of formula XII (0.62 mmol) in methylene chloride (3.1 ml) was added 1-hydroxybenzotriazole hydrate (0.13 g, 0.94 mmol), diisopropylethylamine (0.22 ml, 0.16 g, 1.24 mmol), O-allylhydroxylamine (0.10 g, 0.94 mmol) and 1-(3-dimethylaminopropyl)3-ethylcarbodiimide hydrochloride (0.18 g, 0.94 mmol). After stirring for about 24 hours at a temperature of about 20 to about 25° C., the mixture was diluted with ethyl acetate, washed once with 1M hydrochloric acid, twice with saturated sodium bicarbonate solution and once with brine, dried over anhydrous sodium sulfate, filtered and concentrated in vacuo to give a compound of formula XIII.

The residue was dissolved 6 ml of 20% water in acetonitrile and was treated with 2.5 g of 5:2 formic acid-triethyamine and 80 mg of tetrakis(triphenylphosphine)palladium(0). After being shaken at about 85° C. to about 95° C. for about 1 hour, the mixture was cooled to about 20° C. to about 25° C., diluted with ether and extracted 4 times into 1M Sodium hydroxide. The combined aqueous layers were washed 4 times with ether, acidified to pH<3 with 6M hydrochloric acid and were extracted 3 times into ethyl acetate. The combined ethyl acetate extracts were dried over sodium sulfate, filtered and concentrated in vacuo to afford the corresponding Formula I [(2R,3R) 1-[4-(4-benzyloxy)-benzenesulfonyl]-3-hydroxy-3-methyl-piperidine-2-carboxylic acid hydroxyamide] compound, wherein the identity of the benzyl halide, used above, defines the substituents $R^5$ and $R^6$, as an optically pure, colorless solid after trituration from methylene chloride-hexane or isopropyl ether-hexane.

Example of a Preparation of a Formula I Compound, Wherein X is Carbon, and $R^3$, $R^4$, $R^7$, and $R^8$ are each hydrogen, $R^1$ is hydroxy, $R^2$ is methyl, $R^5$ is hydrogen, and $R^6$ is methyl according to Steps 8–11, Scheme 1 3-Hydroxy-3-methyl-1-[4-(2-methyl-benzyloxy)-benzenesulfonyl]-piperidine-2-carboxylic acid hydroxyamide Following the above general procedure of Steps 8 and 9 for the alkylation and desilylation of 2-(tert-butyl-diphenyl-silanyloxymethyl)-1-(4-hydroxy-benzenesulfonyl)-3-methyl-piperidin-3-ol, compound of formula IX (0.40 g, 0.74 mmol) was alkylated with 2-methylbenzyl bromide to afford 310 mg of 2-hydroxymethyl-3-methyl-1-[4-(2-methyl-benzyloxy)-benzenesulfonyl]-piperidin-3-ol (compound of formula XI) as a colorless syrup.

This material treated according to the general procedure of Step 10, to give 0.31 g of 3-hydroxy-3-methyl-1-[4-(2-methyl-benzyloxy)-benzenesulfonyl]-piperidine-2-carboxylic acid (compound of formula XII) as a colorless syrup.

This carboxylic acid of formula XII was converted to the corresponding Formula I hydroxamic acid following the general procedure of Steps 11 and 12, affording 150 mg of 3-hydroxy-3-methyl-1-[4-(2-methyl-benzyloxy)-benzenesulfonyl]-piperidine-2-carboxylic acid hydroxyamide (compound of Formula I) as a colorless solid.

Example 2

Preparation of a Compound of Formula I, According to General Scheme 2, Wherein X is Carbon, $R^3$, $R^4$, $R^7$, and $R^8$ are Hydrogen, $R^1$ is Hydroxy, and $R^2$, $R^5$, and $R^6$ are as Above Example of a Preparation of a Compound of Formula XV, Step 13, Scheme 2 [4-Benzyloxybenzenesulfonylamino]-acetic acid tert-butyl ester To a mixture of glycine tert butyl ester hydrochloride salt (compound of formula XIV, 50 g, 300 mmol) and dimethylformamide (400 ml) at about 0° C. was added triethylamine (127 ml, 885 mmol) and 4-benzyloxybenzenesulfonyl chloride (102 g, 357 mmol). After stirring for about 1 hour, the mixture was warmed to a temperature of about 20° C. to about 25° C., and stirred for about an additional 12 hours. The mixture was diluted with 1M hydrochloric acid, extracted twice with ethyl acetate, and the combined organic layers were dried over sodium sulfate, filtered and concentrated in vacuo. Trituration of the residue with ether-hexane afforded 91 g of [4-Benzyloxybenzenesulfonylamino]-acetic acid tert-butyl ester (compound of formula XV) as a colorless solid.

Example of a Preparation of a Compound of Formula XVI, Step 14, Scheme 2 [(4-Benzyloxy-benzenesulfonyl)-pent-4-enyl-amino]-acetic acid tert-butyl ester To a mixture of [4-Benzyloxybenzenesulfonylamino]-acetic acid tert-butyl ester (compound of formula XV, 91 g, 240 mmol), cesium carbonate (86 g, 264 mmol) and dimethylformamide (240 ml) was added 4-bromopentene (39 g, 264 mmol) and potassium iodide (39 g). After stirring at about 23° C. for about 24 hours, the mixture was heated to about 55° C. After stirring for about 4 hours, the mixture was treated with additional 4-bromopentene (3.94 g, 26.4 mmol) and cesium carbonate (8.61 g, 26.4 mmol) and was stirred at about 65° C. for about 12 hours. The mixture was cooled to about 23° C., diluted with water and was extracted with ethyl acetate. The organic phase was washed 3 times with water, dried over sodium sulfate, filtered and concentrated in vacuo to afford 89 g of [(4-benzyloxy-benzenesulfonyl)-pent-4-enyl-amino]-acetic acid tert-butyl ester (compound of formula XVI) as a colorless syrup.

Example of a Preparation of a Compound of Formula XVII, Step 15, Scheme 2 [(4-Benzyloxy-benzenesulfonyl)-(4-oxo-pentyl)-amino]-acetic acid tert-butyl ester A mixture of [(4-benzyloxy-benzenesulfonyl)-pent-4-enyl-amino]-acetic acid tert-butyl ester (compound of formula XVI, 89 g, 200 mmol), cuprous chloride (19.8 g, 200 mmol), palladium (II) chloride (6.9 g, 39 mmol), dimethylformamide (541 ml) and water (293 ml) was treated with oxygen gas under vigorous stirring. After about 24 hours, an additional 4 g of cuprous chloride and 2 g of palladium (II) chloride were added, and stirring was continued for 2 days. The mixture was diluted with 1M hydrochloric acid, extracted 3 times with ethyl acetate, and the organic phase was washed 5 times with water, dried over sodium sulfate, filtered and concentrated, giving 83 g of [(4-benzyloxy-benzenesulfonyl)-(4-oxo-pentyl)-amino]-acetic acid tert-butyl ester (compound of formula XVII) as a colorless syrup.

Example of a Preparation of a Compound of Formula XVIII, Step 16, Scheme 2 1-[4-benzyloxy)-benzenesulfonyl-3-hydroxy-3-methyl-piperidine-2-carboxylic acid tert-butyl ester To a solution [(4-benzyloxy-benzenesulfonyl)-(4-oxo-pentyl)-amino]-acetic acid tert-butyl ester (compound of formula XVII, 25 g, 56 mmol) in 200 ml of tetrahydrofuran was added potassium tert-butoxide (24 ml of a 1M solution in tetrahydrofuran, 24 mmol). After stirring for about 24 hours at a temperature of about 20° C. to about 25° C., the mixture was diluted with water, acidified with 1M hydrochloric acid and extracted 3 times into ethyl acetate. The combined organic layers were dried over sodium sulfate, filtered and concentrated in vacuo. The stereoisomers were separated by preparative HPLC on a Chiralpak AD column® eluting with 2-propanol-hexane, affording approximately 4 g of each stereoisomer of 1-[4-benzyloxy)-benzenesulfonyl]-3-hydroxy-3-methyl-piperidine-2-carboxylic acid tert-butyl ester (compound of formula XVIII) as a colorless oil.

Example of a Preparation of a Compound of Formula XIX, Step 17, Scheme 2 3-Hydroxy-1-(4-hydroxy-benzenesulfonyl)-3-methyl-piperidine-2-carboxylic acid tert-butyl ester A mixture of 1-[4-benzyloxy)-benzenesulfonyl]-3-hydroxy-3-methyl-piperidine-2-carboxylic acid tert-butyl ester (compound of formula XVIII, 2.4 g), methanol (100 ml), ethyl acetate (100 ml) and 10% Palladium on carbon (0.47 g) was shaken under about 50 psi of hydrogen gas for about 24 hours. The mixture was filtered through a pad of Celite® and was concentrated in vacuo to afford 3-Hydroxy-1-(4-hydroxy-benzenesulfonyl)-3-methyl-piperidine-2-carboxylic acid tert-butyl ester (compound of formula XIX) as a colorless solid.

General Procedure for the Preparation of a Compound of Formula XII, Wherein X is Carbon, $R^3$, $R^4$, $R^7$, and $R^8$ are Hydrogen, $R^1$ is Hydroxy, and $R^2$, $R^5$, and $R^6$ are as Defined Above, Steps 18 and 19, Scheme 2

A mixture of 3-hydroxy-1-(4-hydroxy-benzenesulfonyl)-3-methyl-piperidine-2-carboxylic acid tert-butyl ester (XIX, 0.20 g, 0.54 mmol), the appropriate alkyl halide (0.81 mmol), cesium carbonate (0.35 g, 1.1 mmol) and dimethylformamide (1 ml) was stirred at about 23° C. for about 24 hours. The mixture was diluted with ethyl acetate, washed 5 times with water, dried over sodium sulfate, filtered and concentrated. Trituration of the residue from isopropyl ether-hexane afforded the corresponding 3-hydroxy-1-(4-arylmethoxy-benzenesulfonyl)-3-methyl-piperidine-2-carboxylic acid tert-butyl ester (compound of formula XX) as a colorless solid.

This material was dissolved in 2 ml of a 1:1 (v/v) solution of trifluoroacetic acid in methylene chloride and was stirred for about 2 hours at about 23° C. Concentration of the mixture afforded the corresponding 3-hydroxy-1-(4-arylmethoxy-benzenesulfonyl)-3-methyl-piperidine-2-carboxylic acid (compound of formula XII), as a colorless solid. This material may then be converted to the corresponding Formula I hydroxamic acid according to the methods described in Steps 11 and 12 of Scheme 1 outlined in Example 1.

Example 3

Preparation of a Compound of Formula I, According to General Scheme 4, Wherein X is Carbon; $R^3$, $R^7$, and $R^8$ are Hydrogen; $R^1$ and $R^2$ are Methyl; $R^4$ is Hydroxy; and $R^5$ and $R^6$ are as Above

Example of a Preparation of a Compound of Formula XXXII, Step 28, Scheme 4 (2R)-3,3-Dimethyl-2-(1-(R)phenyl-ethylamino)-hex-5-enenitrile To a solution of R-α-methylbenzylamine hydrochloride (14 g, 89 mmol) and potassium cyanide (5.8 g, 89 mmol) in 90 ml of methanol at about 0° C. was added a solution of 2,2-dimethyl-4-pentenal (compound of formula XXXI, 10 g, 89 mmol) in 10 ml of methanol. The resultant mixture was warmed to a temperature of about 20° C. to about 25° C. and was stirred for about 48 hours. The mixture was filtered, and the filtrate was concentrated in vacuo. Crystallization from 3:1 methanol-water afforded 10.7 g of R,R-3,3-dimethyl-2-(1-phenyl-ethylamino)-hex-5-enenitrile (compound of formula XXXII) as a colorless solid.

Example of a Preparation of a Compound of Formula XXXIII, Step 29, Scheme 4 R, R, R-5,6-Dihydroxy-3,3-dimethyl-2-(1-phenyl-ethylamino)-hexanenitrile To a solution of R,R-3,3-dimethyl-2-(1-phenyl-ethylamino)-hex-5-enenitrile (compound of formula XXXII, 14 g, 51 mmol) in 640 ml of 1:1 tert-butyl alcohol:water was added potassium ferricyanide (50 g, 152 mmol), potassium carbonate (21 g, 152 mmol and hydroquinidine-9-phenanthryl ether (0.25 g, 0.5 mmol). The mixture was cooled to about 4° C., and potassium osmate dihydrate (0.18 g, 0.5 mmol) was added. After stirring vigorously for about 16 hours, an additional 0.13 g of potassium osmate dihydrate and 0.25 g of hydroquinidine-9-phenanthryl ether were added. The mixture was stirred for about 48 hours and was treated with sodium sulfite, extracted 3 times with ethyl acetate, and the combined organic extracts were dried over sodium sulfate, filtered and concentrated. Filtration of the residue through a pad of silica gel eluting first with 10% ethyl acetate in hexane, followed by 33% ethyl acetate in hexane afforded 11.5 g of R,R,R-5,6-dihydroxy-3,3-dimethyl-2-(1-phenyl-ethylamino)-hexanenitrile (compound of formula XXXIII) as a colorless syrup.

Example of a Preparation of a Compound of Formula XXXIV, Step 30, Scheme 4 (3R,6R)-6-Hydroxymethyl-4,4-dimethyl-3-(1-phenyl-ethylamino)-tetrahydro-pyran-2-one A mixture of R, R, R-5,6-dihydroxy-3,3-dimethyl-2-(1-phenyl-ethylamino)-hexanenitrile (compound of formula XXXIII, 11.5 g) and 163 ml of concentrated aqueous hydrochloric acid (ca. 12 M) was heated to reflux for about 1.5 hours. The mixture was cooled to a temperature of about 20° C. to about 25° C. and was concentrated. The residue was taken up in water, washed twice with ethyl acetate, and the aqueous layer was basified with solid Sodium hydroxide at about 0° C. The aqueous mixture was extracted 3 times into ethyl acetate, and the combined organic layers were dried over sodium sulfate, filtered and concentrated giving 9.3 g of (3R,6R)-6-hydroxymethyl-4,4-dimethyl-3-(1-phenyl-ethylamino)-tetrahydro-pyran-2-one (compound of formula XXXIV) as a colorless syrup.

Example of a Preparation of a Compound of Formula XXXV, Step 31, Scheme 4 (1R,4R)-8,8-Dimethyl-5-(1-phenyl-ethyl)-2-oxa-5-aza-bicyclo[2.2.2]octan-3-one To a solution of (3R,6R)-6-hydroxymethyl-4,4-dimethyl-3-(1-phenyl-ethylamino)-tetrahydro-pyran-2-one (compound of formula XXXIV, 1.42 g, 5.14 mmol) in 45 ml of methylene chloride was added triethylamine (1.1 ml, 7.9 mmol) and p-toluenesulfonyl chloride (1.2 g, 6.2 mmol) at about 0° C. The mixture was warmed to a temperature of about 20° C. to about 25° C. and was stirred for about 46 hours. The mixture was washed twice with water, and the aqueous layers were extracted with methylene chloride. The combined organic layers were dried over $MgSO_4$, filtered and concentrated. Purification of the residue by filtration through a pad of silica gel eluting first with hexane followed by 20% ethyl acetate in hexane afforded 0.4 g of (1R,4R)-8,8-dimethyl-5-(1-phenyl-ethyl)-2-oxa-5-aza-bicyclo[2.2.2]octan-3-one (compound of formula XXXV) as a colorless solid after recrystallization from methanol-water.

Example of a Preparation of a Compound of Formula XXXVI, Step 32, Scheme 4 (1R,4R)-8,8-Dimethyl-2-oxa-5-aza-bicyclo[2.2.2]octan-3-one To a small Parr shaker bottle was added of (1R,4R)-8,8-Dimethyl-5-(1-phenyl-ethyl)-2-oxa-5-aza-bicyclo[2.2.2]octan-3-one (compound of formula XXXV, 1.04 g, 4.01 mmol), methanol (50 ml) and 0.12 g of 10% Palladium on charcoal. The mixture was shaken under about 50 psi of hydrogen for about 19 hours. The mixture was filtered and concentrated, affording 0.59 g of (1R,4R)-8,8-dimethyl-2-oxa-5-aza-bicyclo[2.2.2]octan-3-one (compound of formula XXXVI) as a filmy solid.

Example of a Preparation of a Compound of Formula XXXVII, Step 33, Scheme 4 (1R,4R)-5-(4-Benzyloxy-benzenesulfonyl)-8,8-dimethyl-2-oxa-5-aza-bicyclo[2.2.2]octan-3-one A solution of (1R,4R)-8,8-dimethyl-2-oxa-5-aza-bicyclo[2.2.2]octan-3-one (compound of formula XXXVI, 10 mmol) and dimethylformamide (20 ml) at about 0° C. was treated with triethylamine (10–20 mmol) and 4-benzyloxy-benzenesulfonyl chloride (15 mmol). After stirring for about 1 hours, the mixture is warmed to a temperature of about 20° C. to about 25° C. and stirred for about an additional 12 hours. The mixture is diluted with 1M hydrochloric acid, extracted twice with ethyl acetate, and the combined organic layers are dried over sodium sulfate, filtered and concentrated in vacuo to give (1R,4R)-5-(4-benzyloxy-benzenesulfonyl)-8,8-dimethyl-2-oxa-5-aza-bicyclo[2.2.2]octan-3-one as a colorless syrup.

Example of a Preparation of a Compound of Formula XXXVIII, Step 34, Scheme 4 (1R,4R)-5-(4-Hydroxy-benzenesulfonyl)-8,8-dimethyl-2-oxa-5-aza-bicyclo[2.2.2]octan-3-one A mixture of (1R,4R)-5-(4-benzyloxy-benzenesulfonyl)-8,8-dimethyl-2-oxa-5-aza-bicyclo[2.2.2]octan-3-one (compound of formula XXXVII, 3.7 g, 9.3 mmol), 10% palladium on charcoal (0.8 g) and 470 ml of 1:1 ethyl acetate-methanol was stirred for about 1.5 hours under about 50 psi of hydrogen gas. The mixture was filtered through a pad of Celite®. Concentration of the filtrate afforded 2.4 g (1R,4R)-5-(4-hydroxy-benzenesulfonyl)-8,8-dimethyl-2-oxa-5-aza-bicyclo[2.2.2]octan-3-one (compound of formula XXXVIII) as a colorless solid.

General Procedure for the Preparation of a Compound of Formula XXXIX, Step 35, Scheme 4

A mixture of (1R,4R)-5-(4-hydroxy-benzenesulfonyl)-8,8-dimethyl-2-oxa-5-aza-bicyclo[2.2.2]octan-3-one (compound of formula XXXVIII, 0.15 g, 0.48 mmol), the appropriate alkyl halide (0.97 mmol), potassium carbonate (0.13 g, 0.97 mmol) and dimethylformamide (1 ml) was shaken at about 50° C. for about 24 hours. The mixture was diluted with ethyl acetate, washed 4 times with water, dried over sodium sulfate, filtered and concentrated. Trituration of the residue from isopropyl ether-hexane afforded the corresponding (1R,4R)-5-(4-arylmethoxy-benzenesulfonyl)- 8,8-dimethyl-2-oxa-5-aza-bicyclo[2.2.2]octan-3-one (compound of formula XXXIX) as a colorless solid.

General Procedure for the Preparation of a Compound of Formula XL, Wherein X is Carbon; $R^3$, $R^7$, and $R^8$ are hydrogen; $R^1$ and $R^2$ are methyl; $R^4$ is Hydroxy; and $R^5$ and $R^6$ are as above then conversion to the corresponding compound of Formula I, Steps 36 of Scheme 4 and then Reaction of XL Under the Conditions of Step 12 of Scheme 1

A stock solution of allylhydroxylamine-trimethylaluminum complex was prepared as follows: To a suspension of O-allylhydroxylamine hydrochloride (1.6 g, 11.3 mmol) in 24 ml of toluene at about 0° C. was added trimethylaluminum (5.7 ml of a 2M solution in toluene, 11.3 mmol). The resulting mixture was warmed to about 20° C. to about 25° C. and stirred until homogeneous (about 1 to about 4 hours). A lactone of formula XXXIX prepared as detailed above (0.4 mmol) was treated with 4 ml of the above prepared solution and was shaken at about 85° C. to about 95° C. for about 30 minutes. The mixture was cooled to about 20° C. to about 25° C., diluted with ethyl acetate and was washed once with 1M hydrochloric acid, once with saturated sodium bicarbonate solution, dried over anhydrous sodium sulfate, filtered and concentrated in vacuo to give a compound of formula XL.

A compound of formula XL may be converted into a Formula I compound by using Step 12 of Scheme 1. That is, the residue was dissolved 4 ml of 20% water in acetonitrile and was treated with 1.6 g of 5:2 formic acid-triethylamine and 44 mg of tetrakis(triphenylphosphine)palladium(0). After being shaken at about 85 to about 95° C. for about 1 hour, the mixture was cooled to about 20° C. to about 25° C., diluted with ether and extracted 3 times into 1M Sodium hydroxide. The combined aqueous layers were washed with ether, acidified to a pH of less than 3 with 1M hydrochloric acid and were extracted 3 times into ethyl acetate. The combined ethyl acetate extracts were dried over sodium sulfate, filtered and concentrated in vacuo to afford the desired product as a colorless solid after trituration from methylene chloride-hexane or isopropyl ether-hexane to give the corresponding Formula I compound.

Example of a Preparation of a Compound of Formula I, Wherein X is Carbon; $R^3$, $R^7$, and $R^8$ are Hydrogen; $R^1$ and $R^2$ are Methyl; $R^4$ is Hydroxy; $R^5$ is Fluoro, and $R^6$ is Trifluoromethyl by Treating a Compound of the Formula XXXVIII According to Steps 35, 36, of Scheme 4 and then Reaction of XL Under the Conditions of Step 12 of Scheme 1 (2R,5R)-1-[4-(5-Fluoro-2-trifluoromethyl-benzyloxy)-benzenesulfonyl]-5-hydroxy-3,3-dimethyl-piperidine-2-carboxylic acid hydroxyamide, Compound of Formula I Following the above general procedure for the alkylation of (1R,4R)-5-(4-hydroxy-benzenesulfonyl)-8,8-dimethyl-2-oxa-5-aza-bicyclo[2.2.2]octan-3-one (compound of formula XXXVIII, 0.15 g, 0.48 mmol) using 2-trifluoromethyl-5-fluorobenzyl bromide as the alkyl bromide afforded 170 mg of (1R,4R)-5-[4-(5-fluoro-2-trifluoromethyl-benzyloxy)-benzenesulfonyl]-8,8 -dimethyl-2-oxa-5-aza-bicyclo[2.2.2]octan-3-one (compound of formula XXXIX). This lactone was converted to the corresponding hydroxamic acid following the general procedure of Steps 36 and 12 described above, affording 67 mg of the Formula I compound (2R, 5R)-1-[4-(5-fluoro-2-trifluoromethyl-benzyloxy)-benzenesulfonyl]-5-hydroxy-3,3-dimethyl-piperidine-2-carboxylic acid hydroxyamide (colorless solid).

Example 4

Preparation of a Compound of Formula I, Wherein X is Nitrogen, $R^8$ is Not Present, and $R^7$ is a Group of the Formula

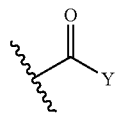

According to General Scheme 5, Wherein, Y is NH—CH$_3$, and $R^1$, $R^2$, $R^3$, $R^4$, $R^5$, and $R^6$, Have the Meanings as Defined Above Example of a Preparation of a Compound of Formula XLI of Scheme 5
2-Benzyloxycarbonylamino-3-hydroxy-butyric acid To a solution of D-threonine (50.7 g, 0.426 mol) in water (800 ml) at about 0° C. was added benzyl chloroformate (66 ml, 0.462 mol) dropwise over about 15 minutes. The reaction was allowed to warm to about 23° C. and was stirred at that temperature for about 18 hours. The reaction was cooled with ice and acidified with concentrated hydrochloric acid, extracted with ether (3 times) and the organic layers were concentrated to give 110.9 g of 2-benzyloxycarbonylamino-3-hydroxy-butyric acid as a colorless oil.

2-Benzyloxycarbonylamino-3-hydroxy-butyric acid, cesium salt

2-Benzyloxycarbonylamino-3-hydroxy-butyric acid (110.9 g, 0.438 mol) was diluted with water (800 ml) and cesium carbonate (72.8 g, 0.224 mol) was added slowly in portions over about 15 minutes. The reaction was stirred at about 23° C. for about 30 minutes and was then concentrated in vacuo and dried on a vacuum pump for about 18 hours to give 155.5 g of 2-benzyloxycarbonylamino-3-hydroxy-butyric acid, cesium salt as a white solid.

3-Bromomethyl-3-methyl-oxetane

To a dichloromethane (600 ml) solution of (3-Methyl-oxetan-3-yl)-methanol (50 g, 0.4896 mol, prepared as in Corey, E. J., Raju, N., *Tetrahedron Lett.*, 1983, 5571) at about 0° C. was added carbon tetrabromide (165.35 g, 0.4986 mol) followed by the addition of triphenyl phosphine (179 g, 0.683 mol) slowly in portions over about 20 minutes. The reaction was allowed to warm to about 23° C. and was stirred at that temperature for about 1 hour then was concentrated in vacuo. The residue was diluted with diethyl ether and cooled to about 0° C., then was filtered through Celite® and the organic layer was concentrated in vacuo. The residue was then diluted with hexanes and filtered then concentrated in vacuo and distilled under vacuum to give 124.3 g of 3-bromomethyl-3-methyl-oxetane as a colorless oil.

2-Benzyloxycarbonylamino-3-hydroxy-butyric acid 3-methyl-oxetan-3-ylmethyl ester To a N,N-dimethylformamide (750 ml) solution 2-benzyloxycarbonylamino-3-hydroxy-butyric acid, cesium salt (123.9 g, 0.322 mol) at about 23° C. was added 3-bromomethyl-3-methyl-oxetane (60 ml, 0.420 mol). The reaction was stirred at about 23° C. for about 18 hours and was then concentrated in vacuo. The residue was diluted with ethyl acetate and extracted with saturated sodium bicarbonate, washed with saturated ammonium chloride and saturated sodium chloride, dried with sodium sulfate and concentrated to give 100 g of the title compound.

2-Hydroxy-1-(4-methyl-2,6,7-trioxa-bicyclo[2.2.2]oct-1-yl)-Propyl]-carbamic acid benzyl ester To a dichloromethane (1.5 L) solution of 2-benzyloxycarbonylamino-3-hydroxy-butyric acid 3-methyl-oxetan-3-ylmethyl 84.76 g, 0.251 mol) at about 0° C. was added boron trifluoride diethyl etherate (2 ml in 50 ml dichloromethane at about 0° C.). The reaction mixture was allowed to warm to about 23° C. and was stirred at that temperature for about 6 hours. The reaction was treated with triethylamine (8 ml) and stirred for about 30 minutes at about 23° C. The reaction mixture was then concentrated in vacuo. The residue was diluted with ethyl acetate and then was extracted with saturated ammonium chloride, washed with saturated sodium chloride, dried with sodium sulfate and concentrated in vacuo. Purification using silica gel chromatography eluting with 1:1 ethyl acetate:hexanes gave 30.45 g of the title compound.

1-Amino-1-(4-methyl-2,6,7-trioxa-bicyclo[2.2.2]oct-1-yl)-propan-2-ol (compound of formula XLI)

A solution of 2-hydroxy-1-(4-methyl-2,6,7-trioxa-bicyclo[2.2.2]oct-1-yl)-propyl]-carbamic acid benzyl ester (38.5 g) in ethyl alcohol (120 ml) was treated with 10% Palladium/C (1.17 g) and subjected to an atmosphere of hydrogen (about 15 psi) for about 35 hours. The reaction mixture was then filtered through Celite® and concentrated in vacuo to give 7.65 g of a compound of formula XLI.

Example of a Preparation of a Compound of Formula XLII, Step 37, Scheme 5 4-Benzyloxy-N-[2-hydroxy-1-(4-methyl-2,6,7-trioxa-bicyclo[2.2.21]oct-1-yl)-propyl]-benzenesulfonamide To a solution of 1-amino-1-(4-methyl-2,6,7-trioxa-bicyclo[2.2.2]oct-1-yl)-propan-2-ol (XLI, 7.65 g, 37.6 mmol) in N,N-dimethylformamide (85 ml) at about 0° C. was added triethylamine (10.6 ml, 114.3 mmol) and 4-benzyloxy-benzenesulfonyl chloride (10.7 g, 37.8 mmol). The reaction was stirred at about 23° C. for about 4 hours prior to the addition of ethyl acetate and water. The mixture was washed with water (3 times), brine (once) and the organic layer was dried with sodium sulfate and concentrated in vacuo to give 13.6 g of a compound of formula XLII.

Example of a Preparation of a Compound of Formula XLV, Step 38, Scheme 5 1-(4-Benzyloxy-benzenesulfonyl)-2-methyl-3-(4-methyl-2,6,7-trioxa-bicyclo[2.2.2]oct-1-yl)-aziridine To a tetrahydrofuran (400 ml) solution of 4-benzyloxy-N-[2-hydroxy-1-(4-methyl-2,6,7-trioxa-bicyclo[2.2.2]oct-1-yl)-propyl]-benzenesulfonamide (compound of formula XLII, 13.62 g, 27.6 mmol) was added triphenylphosphine (12.3 g, 46.9 mmol). The reaction mixture was cooled to about 0° C. and diethylazodicarboxylate (7 ml, 44.5 mmol) was added dropwise. The reaction mixture was stirred for about 18 hours at about 23° C., then was poured onto ethyl acetate and washed with water (twice), brine (once) and the organic layer was dried over sodium sulfate and concentrated in vacuo to give 15 g of a compound of formula XLV containing a small amount of impurities due to the triphenylphosphine and diethylazodicarboxylate.

Example of a Preparation of a Compound of Formula XLIV, Step 39, Scheme 5 1-(4-Benzyloxy-N-[2-(2-hydroxy-ethylamino)-1-(4-methyl-2,6,7-trioxa-bicyclo[2.2.2]oct-1-yl)-propyl]-benzenesulfonamide To a solution of 1-(4-benzyloxy-benzenesulfonyl)-2-methyl-3-(4-methyl-2,6,7-trioxa-bicyclo[2.2.2]oct-1-yl)-aziridine (compound of formula XLV, 9.18 g, 21.3 mmol) in methanol (40 ml) was added ethanolamine (20 ml). The reaction mixture was heated to about 62° C. for about 18 hours then was cooled to about 23° C., was diluted with ethyl acetate, extracted with water, washed with brine and the organic layer was dried with sodium sulfate and concentrated in vacuo to give 10.8 g of a compound of formula XLIV containing a small amount of impurities due to the triphenylphosphine and diethylazodicarboxylate.

Example of a Preparation of a Compound of Formula XLV, Step 40, Scheme 5 1-(4-Benzyloxy-benzenesulfonyl)-3-methyl-2-(4-methyl-2,6,7-trioxa-bicyclo[2.2.2]oct-1-yl)-piperazine 4-Benzyloxy-N-[2-(2-hydroxy-ethylamino)-1-(4-methyl-2,6,7-trioxa-bicyclo[2.2.2]oct-1-yl)-propyl]-benzenesulfonamide (compound of formula XLIV, 10.6 g, 21.5 mmol) was diluted with tetrahydrofuran (400 ml) and cooled to about 0° C. prior to the addition of triphenylphosphine (6.69 g, 25.5 mmol) and diethylazodicarboxylate (4.2 ml, 26.7 mmol). The mixture was allowed to stir at about 0° C. for about 2 hours then was concentrated in vacuo and diluted with ethyl acetate and extracted with water. The organic layer was dried with sodium sulfate and concentrated in vacuo. Silica gel chromatography using ethyl acetate followed by 10% methanol in chloroform containing 0.1% ammonium hydroxide gave 6.8 g of a compound of formula XLV.

Example of a Preparation of a Compound of Formula XLIX, Step 44, Scheme 5 {2-[2-Methyl-4-[4-(2-methyl-benzyloxy)-benzenesulfonyl-3-(4-methyl-2,6,7-trioxa-bicyclo[2.2.2]oct-1-yl)-piperazin-1-yl]-2-oxo-ethyl]-carbamic acid tert-butyl ester To a dichloromethane (12 ml) solution of 1-(4-benzyloxy-benzenesulfonyl)-3-methyl-2-(4-methyl-2,6,7-trioxa-bicyclo[2.2.2]oct-1-yl)-piperazine (XLV, 1.16 g, 2.37 mmol) at about 23° C. was added 1-hydroxybenzotriazole hydrate (481 mg, 3.56 mmol), diisopropylethylamine (1.0 ml, 5.94 mmol), N-t-butoxycarbonylglycine; and 1-(3-dimethylaminopropyl)-3-ethylcarbodiimide hydrochloride (683 mg, 3.56 mmol). The reaction mixture was stirred at about 23° C. for about 16 hours then was diluted with ethyl acetate and saturated aqueous sodium bicarbonate and extracted. The organic layer was dried with sodium sulfate and concentrated in vacuo to give 1.53 g of a compound of formula XLIX.

General Procedure for the Preparation of a Compound of Formula XLV, Step 41, Scheme 5

4-[4-(2-methyl-benzyloxy)-benzenesulfonyl]-2-methyl-3-(4-methyl-2,6,7-trioxa-bicyclo[2.2.2]oct-1-yl)-piperazine-1-carboxylic acid methylamide To a dichloromethane (5 ml) solution of 1-[4-(2-methyl-benzyloxy)-benzenesulfonyl]-3-methyl-2-(4-methyl-2,6,7-trioxa-bicyclo[2.2.2]oct-1-yl)-piperazine (compound of formula XLV, 1.78 g, 3.64 mmol) at about 0° C. was added methyl isocyanate (0.24 ml, 4.0 mmol). The reaction was allowed to stir for about 0.5 hour at about 23° C., was diluted with ethyl acetate and extracted with water. The organic layer was dried with sodium sulfate and then was concentrated to give 1.927 g of a compound of formula XLIV.

General Procedure for the Preparation of a Compound of Formula XLVIII, by Reacting a Compound of the Formula XLVI of Scheme 5 Under the Conditions of Step 44 of Scheme 1

4-(4-Hydroxy-benzenesulfonyl)-2-methyl-3-(4-methyl-2,6,7-trioxa-bicyclo[2.2.2]oct-1-yl)-piperazine-1-carboxylic acid methylamide To an ethanol (15 ml) solution of 4-[4-(2-methyl-benzyloxy)-benzenesulfonyl]-2-methyl-3-(4-methyl-2,6,7-trioxa-bicyclo[2.2.2]oct-1-yl)-piperazine-1-carboxylic acid methylamide (1.9 g, 3.48 mmol) was added 10% palladium hydroxide on carbon (370 mg). The mixture was shaken under about 20 psi hydrogen gas for about 1.5 hours. The resulting mixture was filtered through Celite® and concentrated in vacuo to give 1.55 g of the title compound (compound of formula XLV).

General Procedure for the Preparation of a Compound of Formula XLIV, by Reaction of a Compound of the Formula XLV Under the Conditions of Step 8 of Scheme 1

4-[4-(5-Fluoro-2-methyl-benzyloxy)-benzenesulfonyl]-2-methyl-3-(4-methyl-2,6,7-trioxa-bicyclo[2.2.2]oct-1-yl)-piperazine-1-carboxylic acid methylamide To a N,N-dimethylformamide (1.5 ml) solution of 4-(4-Hydroxy-benzenesulfonyl)-2-methyl-3-(4-methyl-2,6,7-trioxa-bicyclo[2.2.2]oct-1-yl)-piperazine-1-carboxylic acid methylamide (compound of formula XLV, 0.31 g, 0.7 mmol) was added cesium carbonate (0.45 g) and 2-bromomethyl-4-fluoro-1-methyl-benzene (0.214 g, 1.05 mmol). The reaction mixture was stirred at about 45° C. for about 16 hours and then was allowed to cool and was diluted with ethyl acetate and washed with water. The organic layer was dried with sodium sulfate and concentrated in vacuo to give 0.377 g of a compound of formula XLIV.

General Procedure for the Preparation of a Compound of Formula XLVI, Step 42. Scheme 5

1-[4-(5-Fluoro-2-methyl-benzyloxy)-benzenesulfonyl]-3-methyl-4-methylcarbamoyl-piperazine-2-carboxylic acid To a dichloromethane (7 ml) solution of 4-[4-(5-fluoro-2-methyl-benzyloxy)-benzenesulfonyl]-2-methyl-3-(4-methyl-2,6,7-trioxa-bicyclo[2.2.2]oct-1-yl)-piperazine-1-carboxylic acid methylamide (compound of formula XLIV, 376 mg, 0.67 mmol) at about 23° C. was added water (0.14 ml) and trifluoroacetic acid (0.14 ml). The reaction mixture was stirred for about 0.5 hour then was concentrated in vacuo. The residue was diluted with methanol (20 ml) and water (6 ml) and cesium carbonate (45 ml of a 10% solution in water) was added to the mixture. The reaction mixture was heated to about 40° C. for about 24 hours then was cooled to about 23° C., acidified with hydrochloric acid and extracted with ethyl acetate. The organic layer was washed with brine and dried with sodium sulfate and concentrated in vacuo, to give 330 mg of a compound of formula XLVI.

General Procedure for the Preparation of a Compound of Formula I, Wherein X is Nitrogen, $R^8$ is Not Present, and $R^7$ is a Group of the Formula:

Wherein, Y is NH—CH$_3$, $R^1$ is Methyl, $R^2$ is Hydrogen, $R^3$ and $R^4$ are Hydrogen, $R^5$ is Methyl and $R^6$ is Fluoro, Steps 42 and 43 of Scheme 5

4-[4-(5-Fluoro-2-methyl-benzyloxy)-benzenesulfonyl]-2-methyl-4-carboxylic acid methylamide-piperazine-2-carboxylic acid-allyloxyamide To a dichloromethane (3.5 ml) solution of 1-[4-(5-Fluoro-2-methyl-benzyloxy)benzenesulfonyl]-3-methyl-4-methylcarbamoyl-piperazine-2-carboxylic acid (compound of formula XLVI, 320 mg, 0.67 mmol) at about 23° C. was added allylhydroxylamine hydrochloride (110 mg, 1.0 mmol), 1-hydroxybenzotriazole hydrate (137 mg, 1.0 mmol), diisopropylethyl amine (0.30 ml, 1.68 mmol) and 1-(3-dimethylaminopropyl)-3-ethylcarbodiimide hydrochloride (193 mg, 1.0 mmol). The mixture was stirred for about 24 hours at about 23° C. then was diluted with ethyl acetate and dilute aqueous sodium bicarbonate and extracted. The organic layer was dried with sodium sulfate and concentrated in vacuo. Silica gel chromatography gave 290 mg of the title Formula I compound.

Example 5

General Procedure for the Preparation of a Compound of Formula I, Wherein X is Nitrogen, $R^8$ is Not Present, and $R^7$ is a Group of the Formula

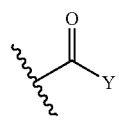

Wherein, Y is CH$_2$—NH$_2$ and $R^1$, $R^2$, $R^3$, $R^4$, $R^5$, $R^6$, Have the Meanings as Defined Above According to Scheme 6

4-[4-(5-Fluoro-2-methyl-benzyloxy)-benzenesulfonyl]-2-methyl-4-carboxylic acid methylamide-piperazine-2-carboxylic acid hydroxyamide To an acetonitrile:water (4:1, 2.75 ml) solution of 4-[4-(5-fluoro-2-methyl-benzyloxy)-benzenesulfonyl]-2-methyl-piperazine-1,3-dicarboxylic acid 3-(allyloxy-amide) 1-methylamide (290 mg, 0.55 mmol) was added triethyl ammonium formate (0.22 ml) and palladium tetrakis triphenylphosphine (63 mg). The reaction mixture was heated to about 85° C. for about 30 minutes then was cooled to about 23° C. and extracted with ethyl acetate and dilute aqueous sodium bicarbonate. The organic layer was dried with sodium sulfate and concentrated in vacuo. Chromatography on silica gel using ethyl acetate then 10% methanol:ethyl acetate gave 149.8 mg of the title Formula I compound.

Example of a Preparation of a Compound of Formula L, Wherein $P^{10}$ is Butyloxycarbonyl, Steps 42 and 43, Scheme 6 (2-{(3-Hydroxycarbamoyl-2-methyl-4-[(2-methyl-benzyloxy)-benzenesulfonyl]-piperazin-1-yl}-2-oxo-ethyl)-carbamic acid tert-butyl ester The title compound was prepared from {2-[2-Methyl-4-[4-(2-methyl-benzyloxy)-benzenesulfonyl]-3-(4-methyl-2,6,7-trioxa-bicyclo[2.2.2]oct-1-yl)-piperazin-1-yl]-2-oxo-ethyl}-carbamic acid tert-butyl ester according to steps 42 and 43 of Scheme 6 (i.e., the same procedure described above for 4-[4-(5-fluoro-2-methyl-benzyloxy)-benzenesulfonyl]-2-methylpiperazine-1,3-dicarboxylic acid 3-hydroxyamide 1-methylamide).

Example of a Preparation of a Compound of Formula I Wherein X is Nitrogen, $R^8$ is Not Present, and $R^7$ is a Group of the Formula Wherein, Y is CH$_2$—NH$_2$ and $R^1$ is Methyl, $R^5$ is Ethyl, and $R^2$, $R^3$, $R^4$, $R^6$ are Hydrogen According to Step 45, Scheme 6

1-[4-(2-methyl-benzyloxy)-benzenesulfonyl]-4-aminoacetyl-3-methyl-piperazine-2-carboxylic acid hydroxyamide, trifluoroacetate salt To a dichloromethane (4.3 ml) solution of (2-{3-Hydroxycarbamoyl-2-methyl-4-[4-(2-methyl-benzyloxy)-benzenesulfonyl]-piperazin-1-yl}-2-oxo-ethyl)-carbamic acid tert-butyl ester (compound of formula

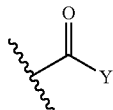

L, 0.25 g, 0.43 mmol) at about 23° C. was added trifluoroacetic acid (0.4 ml). The reaction was stirred for about 10 minutes then was concentrated in vacuo to give 180 mg of the title compound. This compound can be neutralized according to standard methods to give the corresponding Formula I compound as the free amine.

1-[4-(2-Ethyl-benzyloxy)-benzenesulfonyl]-2-methyl-4-aminoacetyl-piperazine-2-carboxylic acid hydroxyamide The title compound was prepared using the procedures described for 4-[4-(5-fluoro-2-methyl-benzyloxy)-benzenesulfonyl]-2-methyl-piperazine-1,3-dicarboxylic acid 3-hydroxyamide 1-methylamide (i.e., reaction of a compound of formula XLV with 1-bromomethyl-2-ethyl-benzene under the conditions of Step 8 of Scheme 1 to obtain a compound of formula XLV with a 1 bromomethyl-2-ethyl-benzyl group. Steps 41–43 of Scheme 5 then provided 4-[4-(2-ethyl-benzyloxy)-benzenesulfonyl]-2-methyl-piperazine-1,3-dicarboxylic acid 3-hydroxyamide-1-methylamide, 149.8 mg (56% yield).

Example 6

Preparation of a Compound of Formula I Wherein X is Nitrogen; $R^8$ is Not Present; $R^7$ is Hydrogen; $R^3$ and $R^4$ are Taken Together to Form a Carbonyl Group; and $R^1$, $R^2$, $R^5$, and $R^6$ Have the Meanings as Defined Above According to General Scheme 7

Example of a Preparation of a Compound of Formula LI, Step 46, Scheme 7 N-[2-Amino-1-(4-methyl-2,6,7-trioxa-bicyclo[2.2.2]oct-1-yl)-propyl]-4-benzyloxy-benzenesulfonamide A solution of 1-(4-benzyloxy-benzenesulfonyl)-2-methyl-3-(4-methyl-2,6,7-trioxa-bicyclo[2.2.2]oct-1-yl)-aziridine (compound of formula XLV, 3.0 g, 7.0 mmol) prepared as outlined in Scheme 5, in methanol (15 ml, saturated with ammonia gas at about 0° C.) was heated to about 50° C. for about 24 hours. The mixture was concentrated in vacuo to afford 2.8 g of N-[2-Amino-1-(4-methyl-2,6,7-trioxa-bicyclo[2.2.2]oct-1-yl)-propyl]-4-benzyloxy-benzenesulfonamide (compound of formula LI) as a colorless solid.

Example of a Preparation of a Compound of Formula LII, Step 47, Scheme 7 [2-(4-Benzyloxy-benzenesulfonylamino)-1-methyl-2-(4-methyl-2,6,7-trioxa-bicyclo[2.2.2]oct-1-yl)-ethyl]-carbamic acid benzyl ester A solution of N-[2-amino-1-(4-methyl-2,6,7-trioxa-bicyclo[2.2.2]oct-1-yl)-propyl]-4-benzyloxy-benzenesulfonamide (compound of formula LI, 2.5 g, 5.6 mmol), triethyl amine (1.01 ml, 0.73 g, 7.22 mmol) in 31 ml of 2:1 (v/v) 1,4-dioxane-water was treated with benzyl chloroformate (1.20 ml, 1.43 g, 8.40 mmol) at about 0° C. After stirring for about 3 hours at about 0° C., the mixture was diluted with ethyl acetate, washed twice with water, once with brine, dried over sodium sulfate, filtered and concentrated in vacuo. The residue was purified by silica gel chromatography eluting with 2:1 hexane-ethyl acetate, affording 2.0 g of [2-(4-benzyloxy-benzenesulfonylamino)-1-methyl-2-(4-methyl-2,6,7-trioxa-bicyclo[2.2.2]oct-1-yl)-ethyl]-carbamic acid benzyl ester (compound of formula LII) as a colorless syrup.

Example of a Preparation of a Compound of Formula LIII, Step 48, Scheme 7 {(4-Benzyloxy-benzenesulfonyl)-[2-benzyloxycarbonylamino-1-(4-methyl-2,6,7-trioxa-bicyclo[2.2.2]oct-1-yl)-propyl]-amino}-acetic acid methyl ester A solution of [2-(4-benzyloxy-benzenesulfonylamino)-1-methyl-2-(4-methyl-2,6,7-trioxa-bicyclo[2.2.2]oct-1-yl)-ethyl]-carbamic acid benzyl ester (compound of formula LII, 1.2 g, 2.0 mmol) in 2 ml of dimethylformamide was treated with cesium carbonate (1.12 g, 3.4 mmol) and methyl bromoacetate (0.2 ml, 0.32 g, 2.1 mmol). After stirring for about 2 hours, the mixture was diluted with ethyl acetate, washed 5 times with water, and the organic phase was dried over sodium sulfate, filtered and concentrated, affording 1.3 g of {(4-benzyloxy-benzenesulfonyl)-[2-benzyloxycarbonylamino-1-(4-methyl-2,6,7-trioxa-bicyclo[2.2.2]oct-1-yl)-propyl]-amino}-acetic acid methyl ester (compound of formula LIII) as a colorless syrup.

Example of a Preparation of a Compound of Formula LIV, Wherein X is Nitrogen; $R^8$ is Not Present; $R^7$ is Hydrogen, $R^3$ and $R^4$ are Taken Together to Form a Carbonyl Group; and $R^1$ is Hydrogen, $R^2$ is Methyl, $R^5$ is Hydroxy, and $R^6$ is Hydrogen According to Step 49, Scheme 7 4-(4-Hydroxy-benzenesulfonyl)-6-methyl-5-(4-methyl-2,6,7-trioxa-bicyclo[2.2.2]oct-1-yl)-piperazin-2-one A solution of {(4-benzyloxy-benzenesulfonyl)-[2-benzyloxycarbonylamino-1-(4-methyl-2,6,7-trioxa-bicyclo[2.2.2]oct-1-yl)-propyl]-amino}-acetic acid methyl ester (compound of formula LIII, 1.3 g, 2.0 mmol) in 75 ml of ethanol was treated with triethylamine (0.28 ml, 0.20 g, 2.0 mmol) and 0.2 g of 10% palladium on carbon. After stirring for about 2 hours under 1 atmosphere of hydrogen, the mixture was filtered through a pad of Celite® and concentrated in vacuo. The residue was dissolved in 10 ml of toluene, diluted with 3 ml of methanol and was refluxed for about 1.5 hours. Concentration of the mixture in vacuo afforded 0.6 g of 4-(4-hydroxy-benzenesulfonyl)-6-methyl-5-(4-methyl-2,6,7-trioxa-bicyclo[2.2.2]oct-1-yl)-piperazin-2-one (compound of formula LIV). A compound of the formula LI can be converted to a compound of the formula LIII by the method of Step 42 that, in turn, can be converted to a compound of Formula I according to the procedure of Step 43.

What is claimed is:

1. A compound represented by formula I:

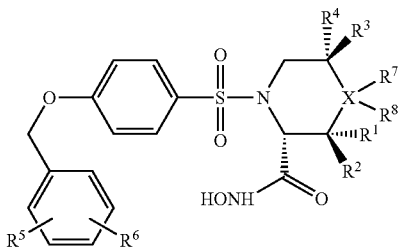

or a pharmaceutically acceptable salt thereof, wherein
X is nitrogen;
R¹ and R² are independently selected from the group consisting of hydrogen, hydroxy, and methyl, wherein at least one of R¹ and R² is methyl;
R³ and R⁴ are independently selected from the group consisting of hydrogen, hydroxy, and methyl, or R³ and R⁴ may be taken together to form a carbonyl group; and
R⁵ and R⁶ are independent substituents in the ortho, meta, or para positions and are independently selected from the group consisting of hydrogen, halogen, cyano, methyl, and ethyl;
R⁸ is not present;
R⁷ is hydrogen or a group of the formula:

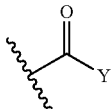

wherein, Y is —CH₂—NH₂ or —NH—CH₃; and
when R⁷ is H, then R³ and R⁴ are taken together to form a carbonyl group.

2. A compound, or a pharmaceutically acceptable salt thereof, selected from the group consisting of:

(2R,3S) 1-[4-(2-methyl-benzyloxy)-benzenesulfonyl]-4-aminoacetyl-3-methyl-piperazine-2-carboxylic acid hydroxyamide;

(2R,3S) 1-[4-(4-fluoro-2-methyl-benzyloxy)-benzenesulfonyl]-3-methyl-5-oxo-piperazine-2-carboxylic acid hydroxyamide;

(2R,3S) 4-[4-(2-ethyl-benzyloxy)-benzenesulfonyl]-3-methyl-4-carboxylic acid methylamide-piperazine-2-carboxylic acid hydroxyamide;

(2R,3S) 4-[4-(5-fluoro-2-methyl-benzyloxy)-benzenesulfonyl]-3-methyl-4-carboxylic acid methylamide-piperazine-2-carboxylic acid hydroxyamide;

(2R,3S) 1-[4-(2-methyl-5-fluoro-benzyloxy)-benzenesulfonyl]-3-methyl-5-oxo-piperazine-2-carboxylic acid hydroxyamide; and (2R,3S) 4-[4-(2,4-difluoro-benzyloxy)-benzenesulfonyl]-3-methyl-4-carboxylic acid methylamide-piperazine-2-carboxylic acid hydroxyamide.

3. A pharmaceutical composition comprising:

a pharmaceutically acceptable carrier; and a therapeutically effective amount of a compound, or a pharmaceutically acceptable salt thereof, selected from the group consisting of:

(2R,3S) 1-[4-(2-methyl-benzyloxy)-benzenesulfonyl]-4-aminoacetyl-3-methyl-piperazine-2-carboxylic acid hydroxyamide;

(2R,3S) 1-[4-(4-fluoro-2-methyl-benzyloxy)-benzenesulfonyl]-3-methyl-5-oxo-piperazine-2-carboxylic acid hydroxyamide;

(2R,3S) 4-[4-(2-ethyl-benzyloxy)-benzenesulfonyl]-3-methyl-4-carboxylic acid methylamide-piperazine-2-carboxylic acid hydroxyamide;

(2R,3S) 4-[4-(5-fluoro-2-methyl-benzyloxy)-benzenesulfonyl]-3-methyl-4-carboxylic acid methylamide-piperazine-2-carboxylic acid hydroxyamide;

(2R,3S) 1-[4-(2-methyl-5-fluoro-benzyloxy)-benzenesulfonyl]-3-methyl-5-oxo-piperazine-2-carboxylic acid hydroxyamide; and (2R,3S) 4-[4-(2,4-difluoro-benzyloxy)-benzenesulfonyl]-3-methyl-4-carboxylic acid methylamide-piperazine-2-carboxylic acid hydroxyamide.

* * * * *